US006464720B2

(12) United States Patent
Boatman et al.

(10) Patent No.: US 6,464,720 B2
(45) Date of Patent: Oct. 15, 2002

(54) RADIALLY EXPANDABLE STENT

(75) Inventors: Scott E. Boatman, Bloomington, IN (US); Kimberly D. Brummett, Bloomfield, IN (US); Thomas A. Osborne, Bloomington, IN (US)

(73) Assignee: Cook Incorporated, Bloomington, IN (US)

( * ) Notice: Subject to any disclaimer, the term of this patent is extended or adjusted under 35 U.S.C. 154(b) by 0 days.

(21) Appl. No.: 09/822,066

(22) Filed: Mar. 30, 2001

(65) Prior Publication Data

US 2001/0027339 A1 Oct. 4, 2001

Related U.S. Application Data

(62) Division of application No. 09/160,122, filed on Sep. 24, 1998, now Pat. No. 6,231,598

(60) Provisional application No. 60/059,898, filed on Sep. 24, 1997, and provisional application No. 60/082,164, filed on Apr. 17, 1998.

(51) Int. Cl.[7] .................................................. A61F 2/06

(52) U.S. Cl. .................................... 623/1.15; 623/1.34

(58) Field of Search .............................. 623/1.34, 1.15; 600/3

(56) References Cited

U.S. PATENT DOCUMENTS

| | | | | |
|---|---|---|---|---|
| 5,104,404 A | | 4/1992 | Wolff | |
| 5,632,771 A | | 5/1997 | Boatman et al. | |
| 5,725,549 A | | 3/1998 | Lam | |
| 5,741,327 A | | 4/1998 | Frantzen | |
| 5,824,042 A | | 10/1998 | Lombardi et al. | |
| 5,922,020 A | * | 7/1999 | Klein et al. | 623/1.34 |
| 5,993,481 A | | 11/1999 | Marcade et al. | |
| 6,334,871 B1 | * | 1/2002 | Dor et al. | 623/1.34 |
| 6,355,057 B1 | * | 3/2002 | DeMarais et al. | 623/1.15 |

FOREIGN PATENT DOCUMENTS

| | | |
|---|---|---|
| EP | 0679372 | 11/1995 |
| WO | 9733534 | 9/1997 |

* cited by examiner

*Primary Examiner*—David H. Willse
*Assistant Examiner*—Suzette J. Jackson
(74) *Attorney, Agent, or Firm*—Richard J. Godlewski

(57) ABSTRACT

A radially expandable stent (10) made from a cannula or sheet of biocompatible material that includes at least one longitudinal segment (14) comprised of a series of laterally interconnected closed cells (13). Each closed cell of a longitudinal segment is defined laterally by a pair of longitudinal struts (15, 16) that are interconnected at each end by a circumferentially adjustable member (19, 20). When the stent is expanded using a balloon (47), the opposing circumferentially adjustable members deform to allow circumferential expansion of the longitudinal segment, while the length of the segment, as defined by the longitudinal struts, is maintained. Self-expanding versions of the stent utilize a nickel-titanium alloy. Adjacent longitudinal segments are joined by flexible interconnection segments (21) that permit the stent to bend laterally. The flexible interconnection segment is comprised of curvilinear struts (22, 23) that form a series of serpentine bends (81) that distribute lateral bending forces. In a preferred embodiment, a short strut interconnects longitudinal segments and an adjacent interconnection segment. Each interconnection strut attaches to the longitudinal segment within a region (27) at the end (17) of a longitudinal strut (15) dividing two adjacent closed cells.

20 Claims, 42 Drawing Sheets

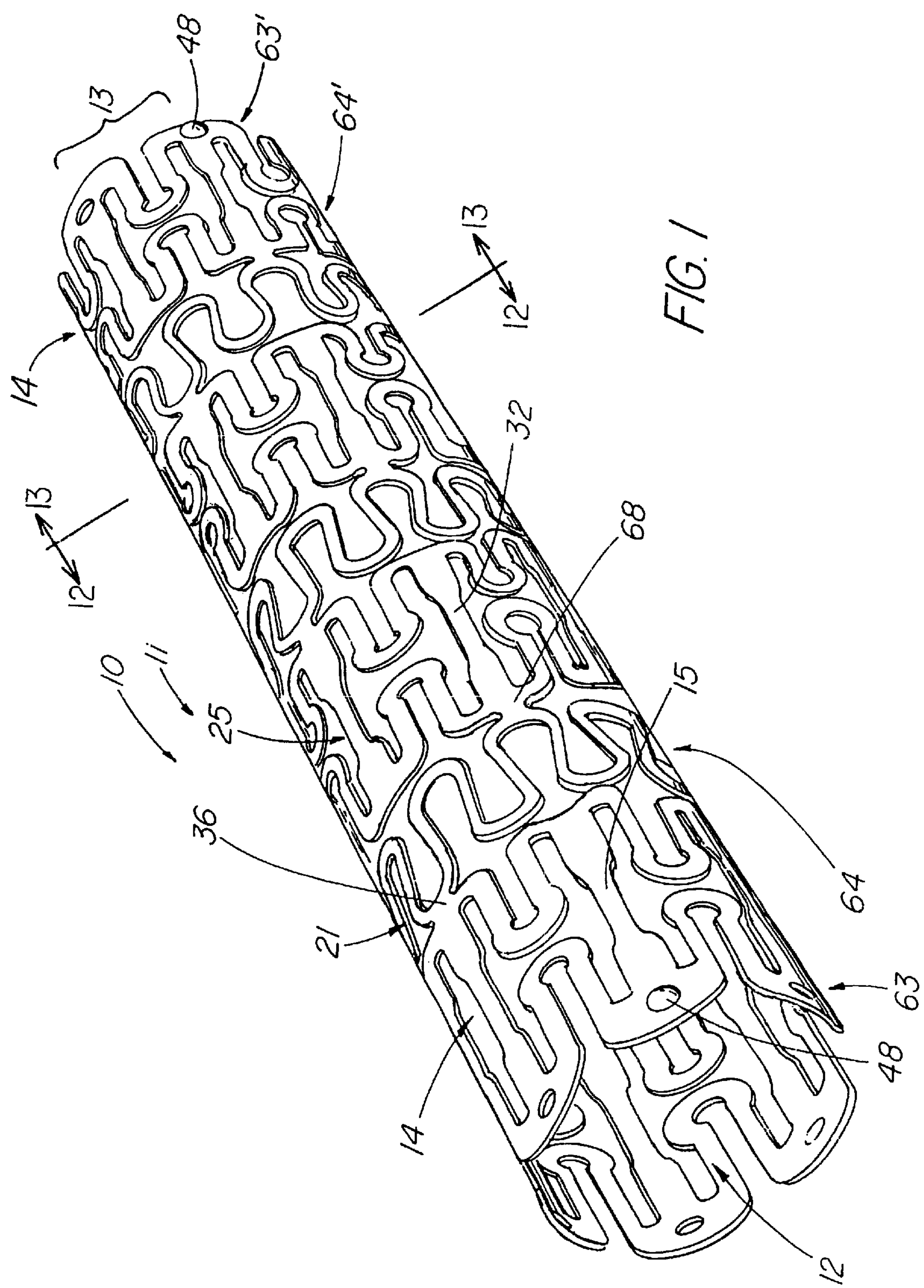
FIG. 1

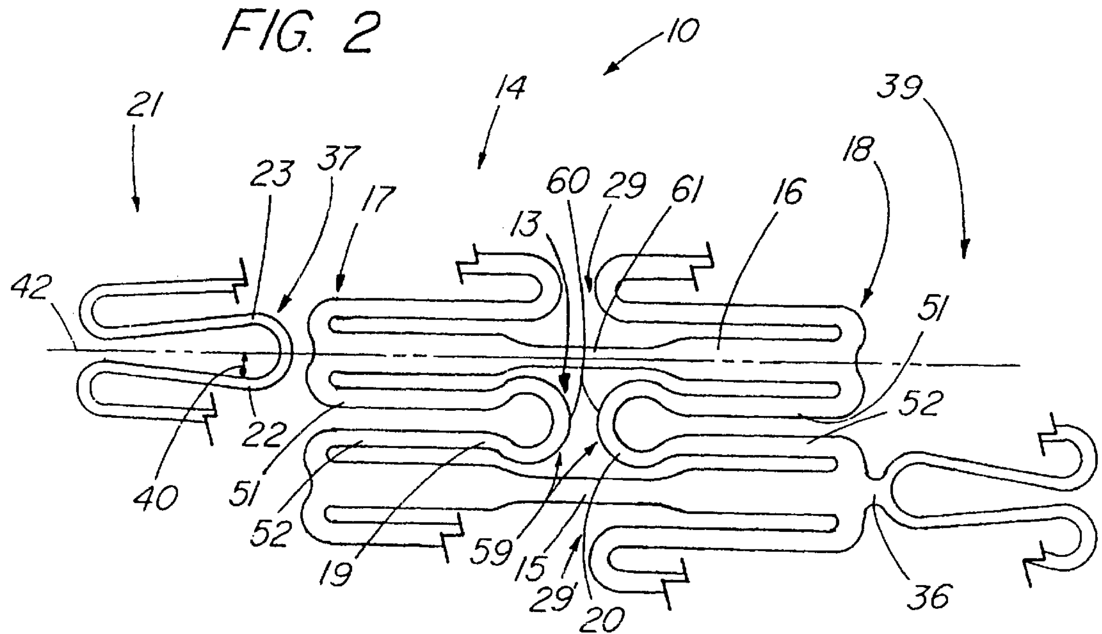
FIG. 2
10
14
39
21
23
37
17
18
60
29
61
16
13
42
51
52
22
40
51
52
19
59
15
29'
20
36
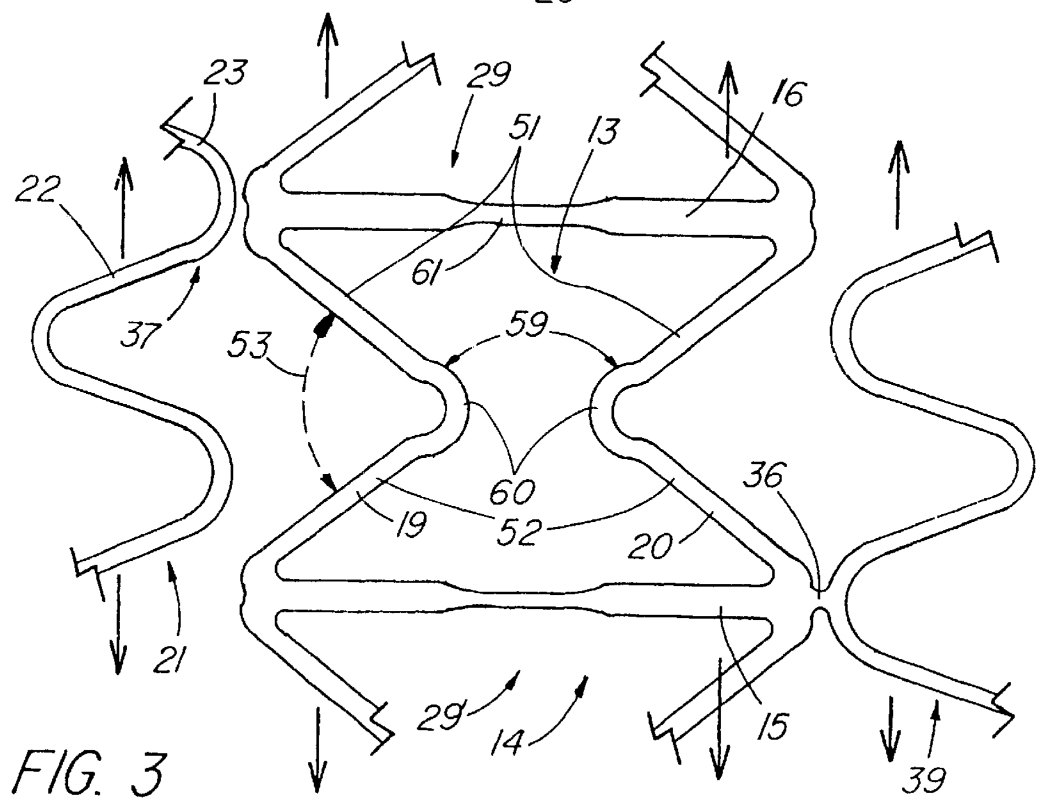
23
29
16
51
13
22
61
37
53
59
60
19
52
20
36
21
29
14
15
39
FIG. 3

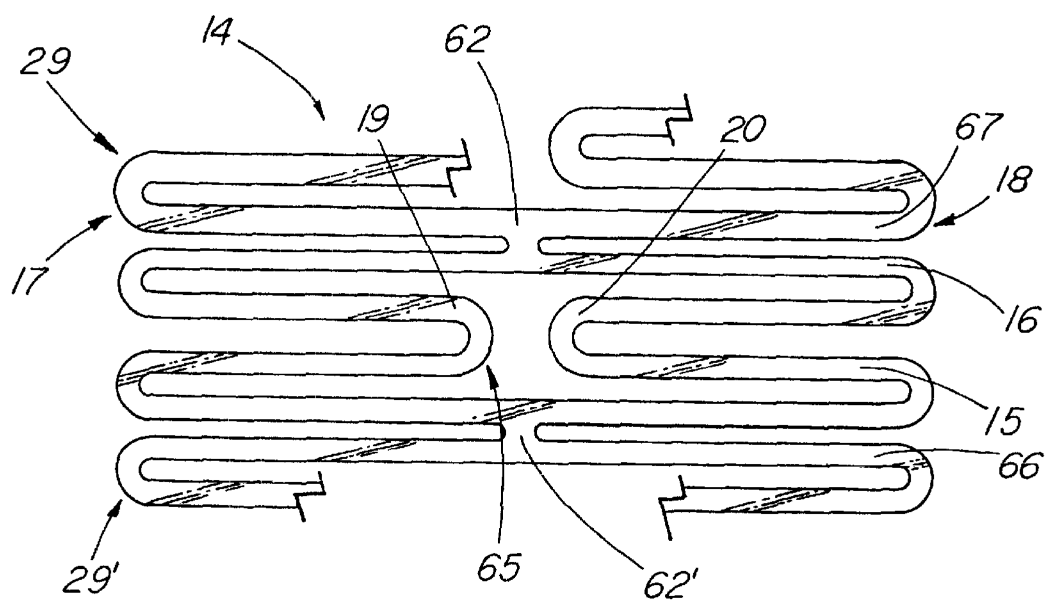
FIG. 4

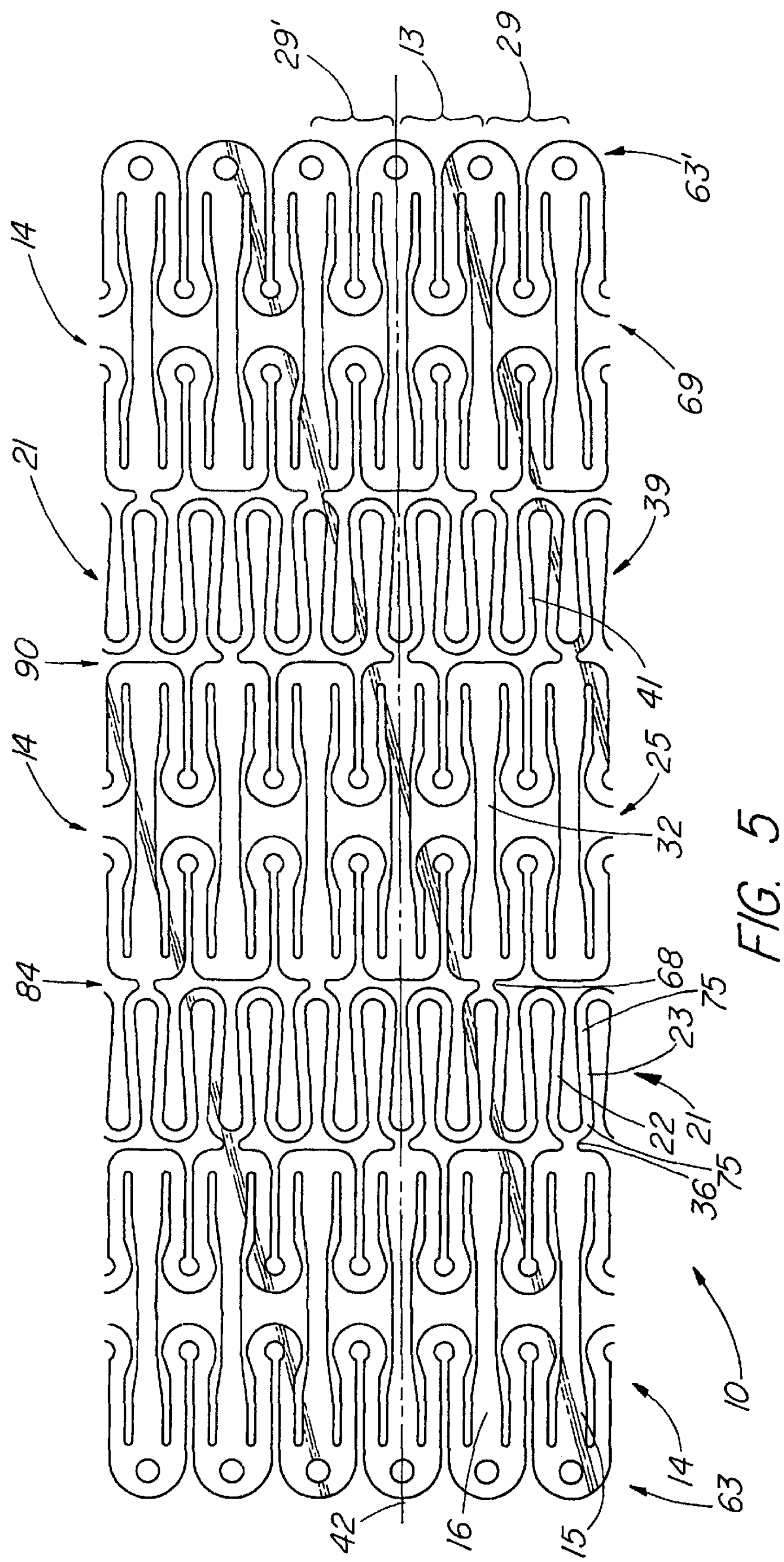
FIG. 5

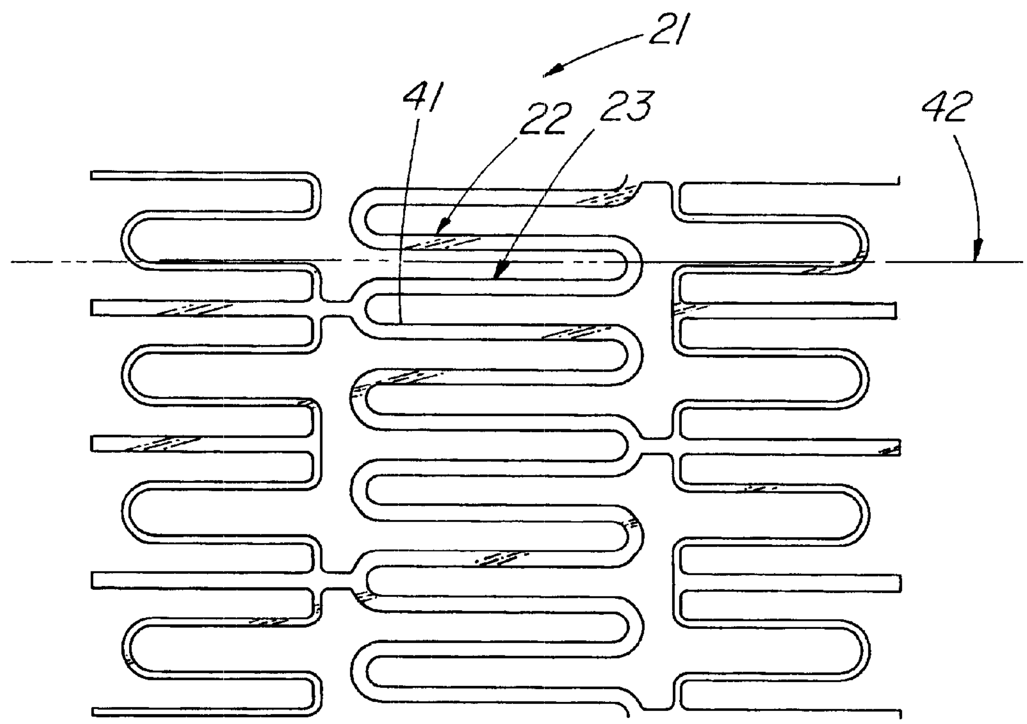
FIG. 6
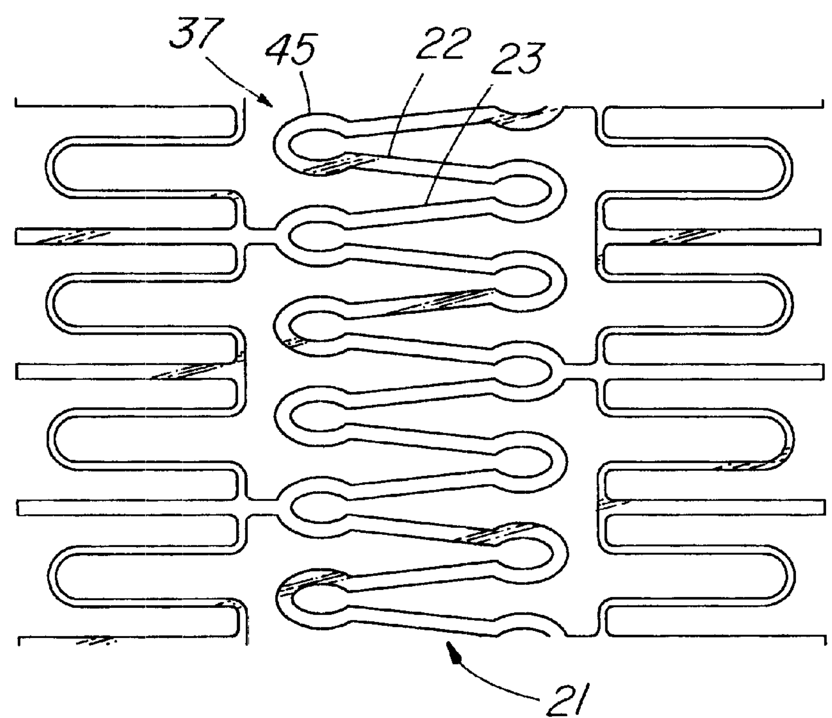
FIG. 7

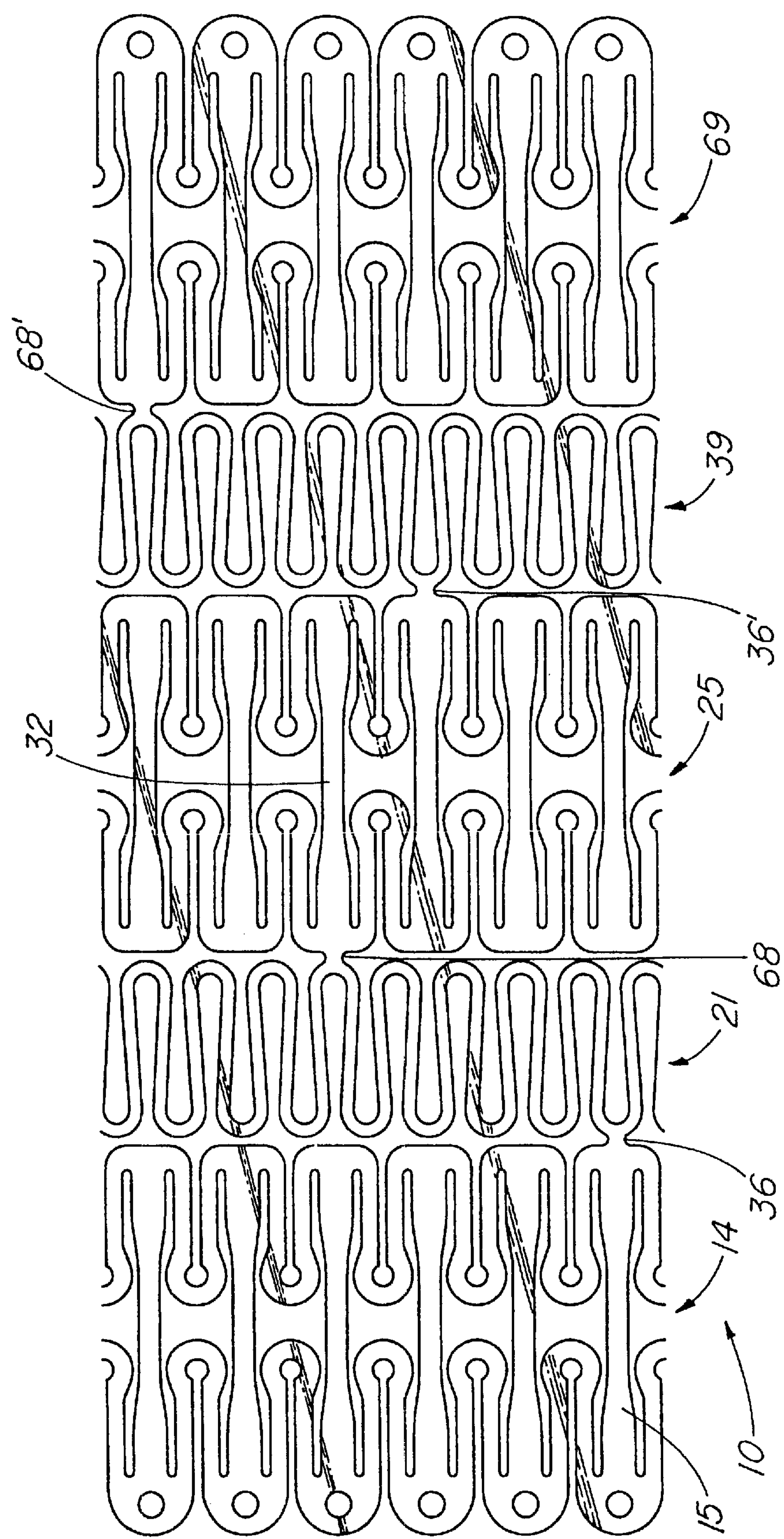
69
68'
39
36'
25
32
68
21
36
14
10
15
FIG. 8

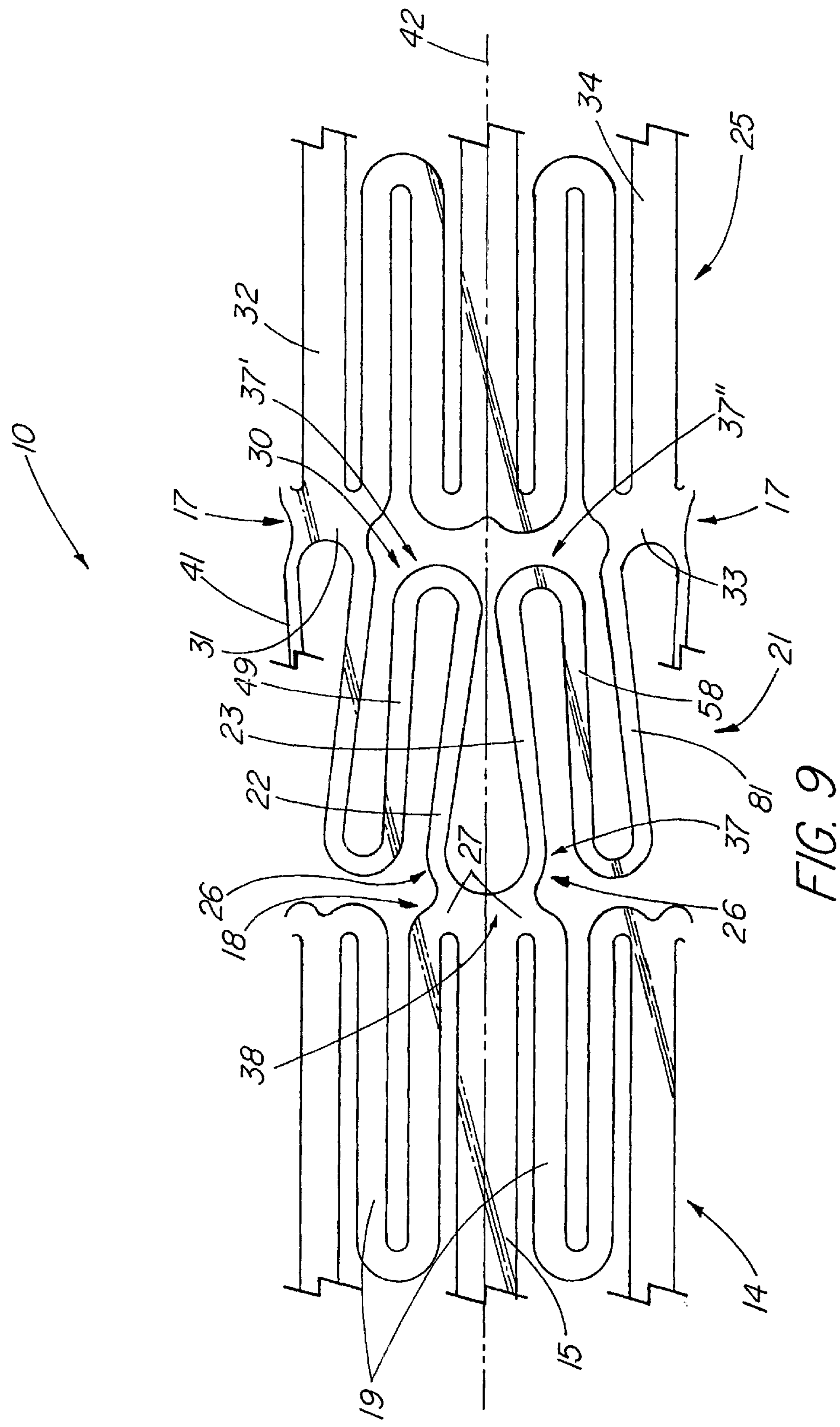
FIG. 9

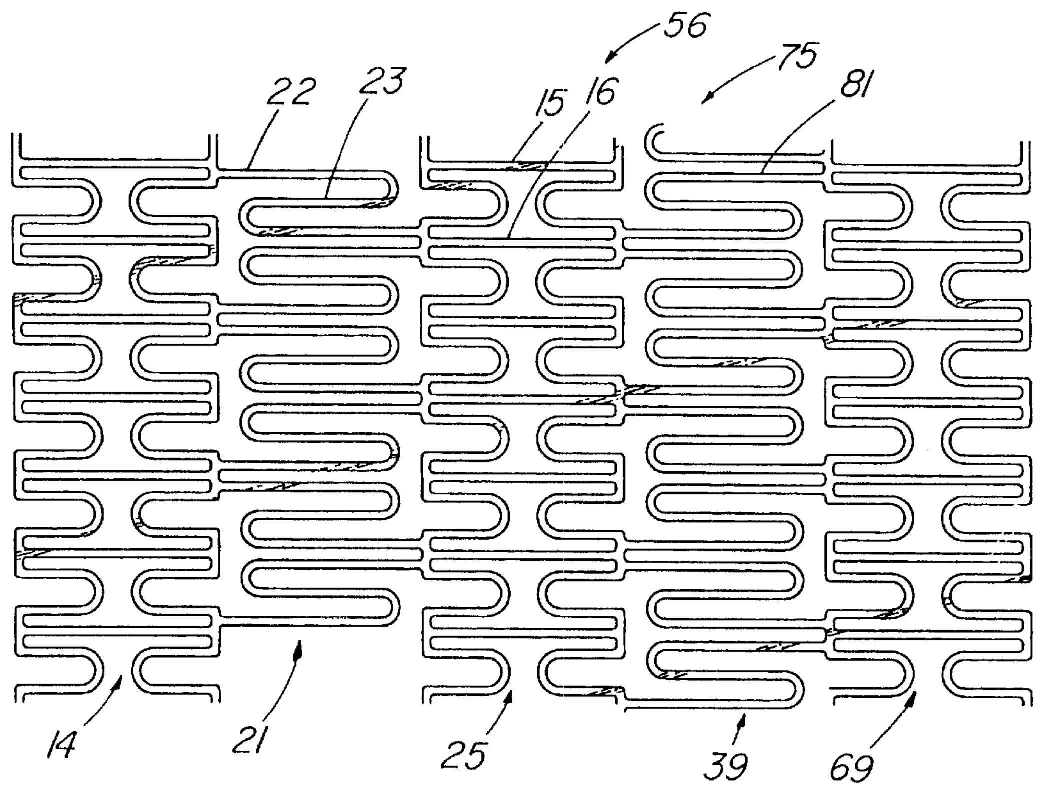
FIG. 10
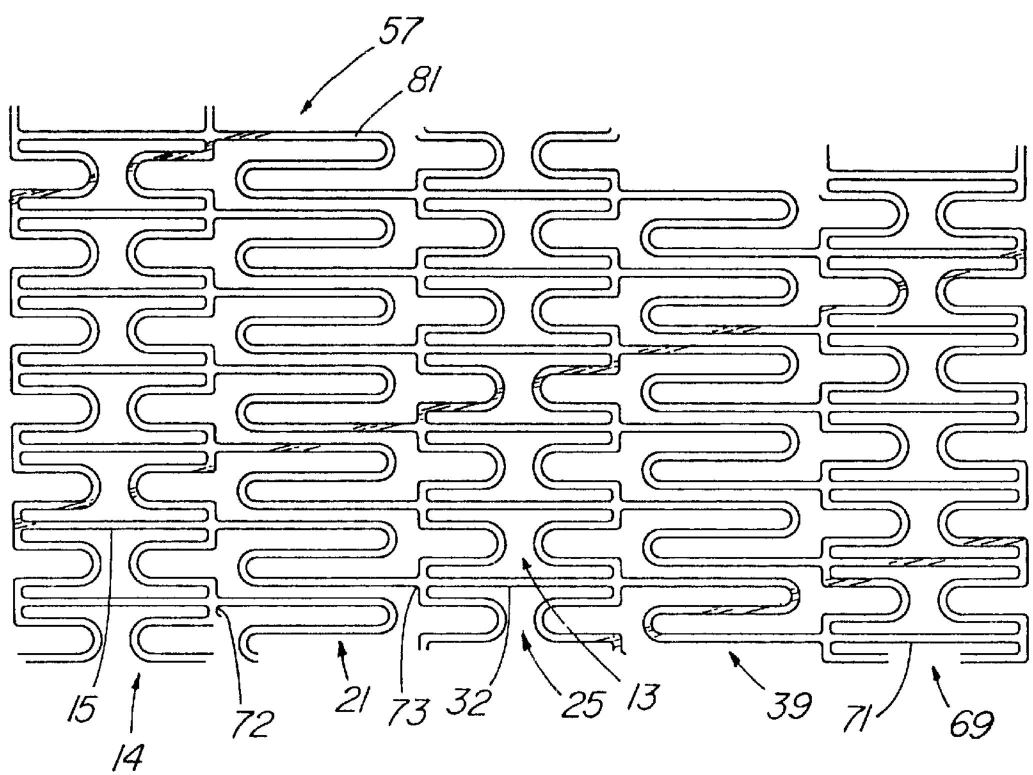
FIG. 11

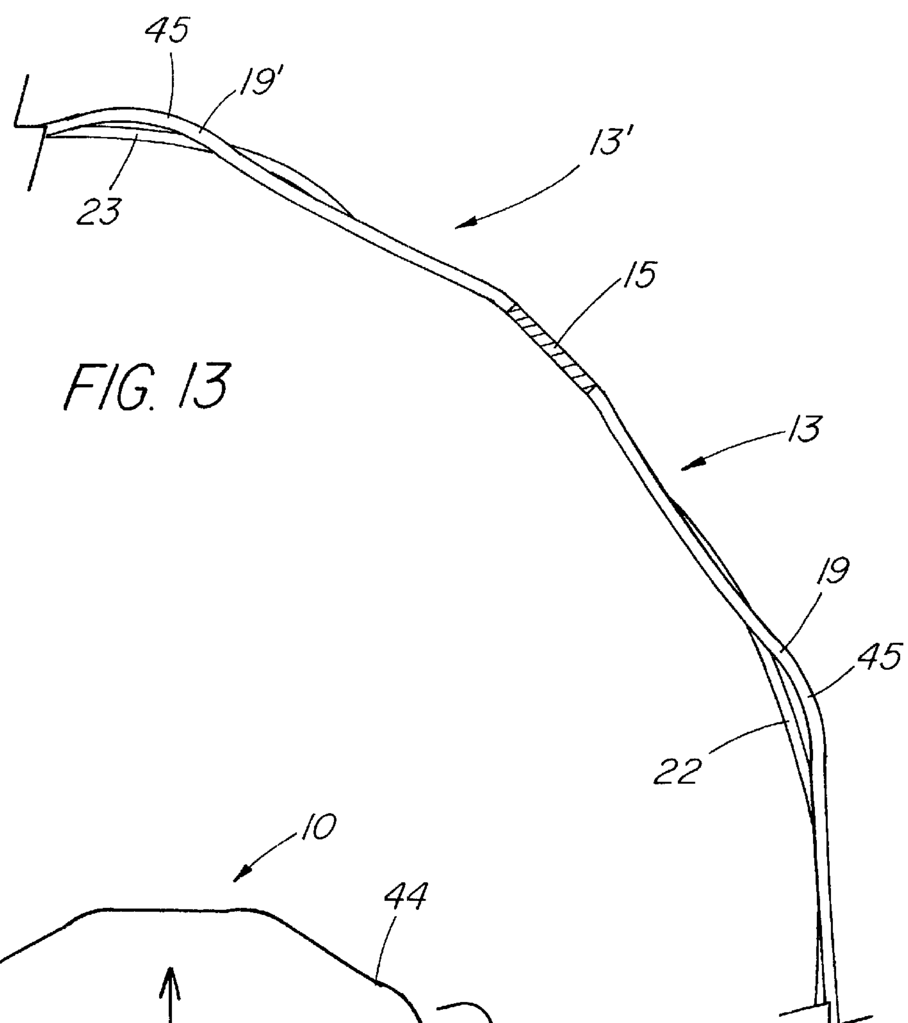
FIG. 13
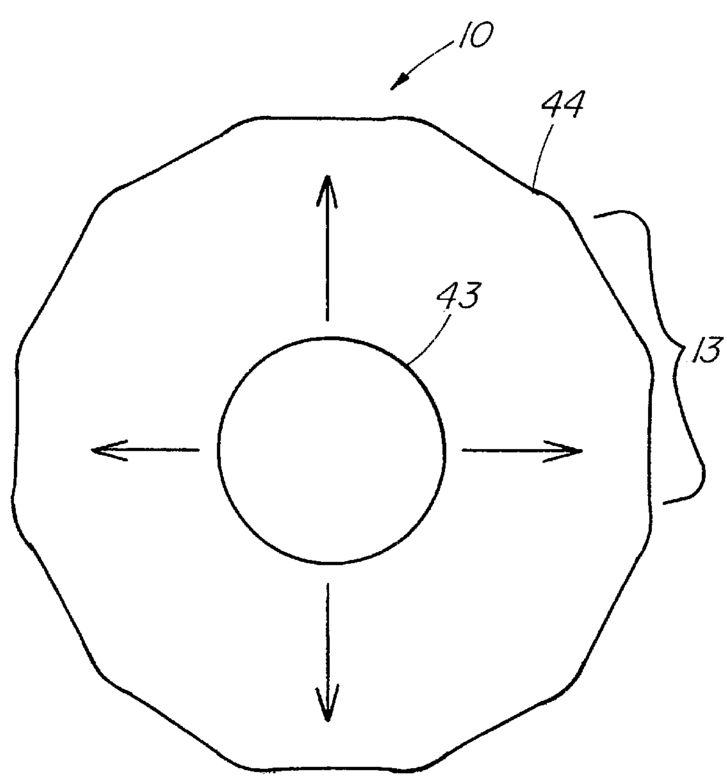
FIG. 12

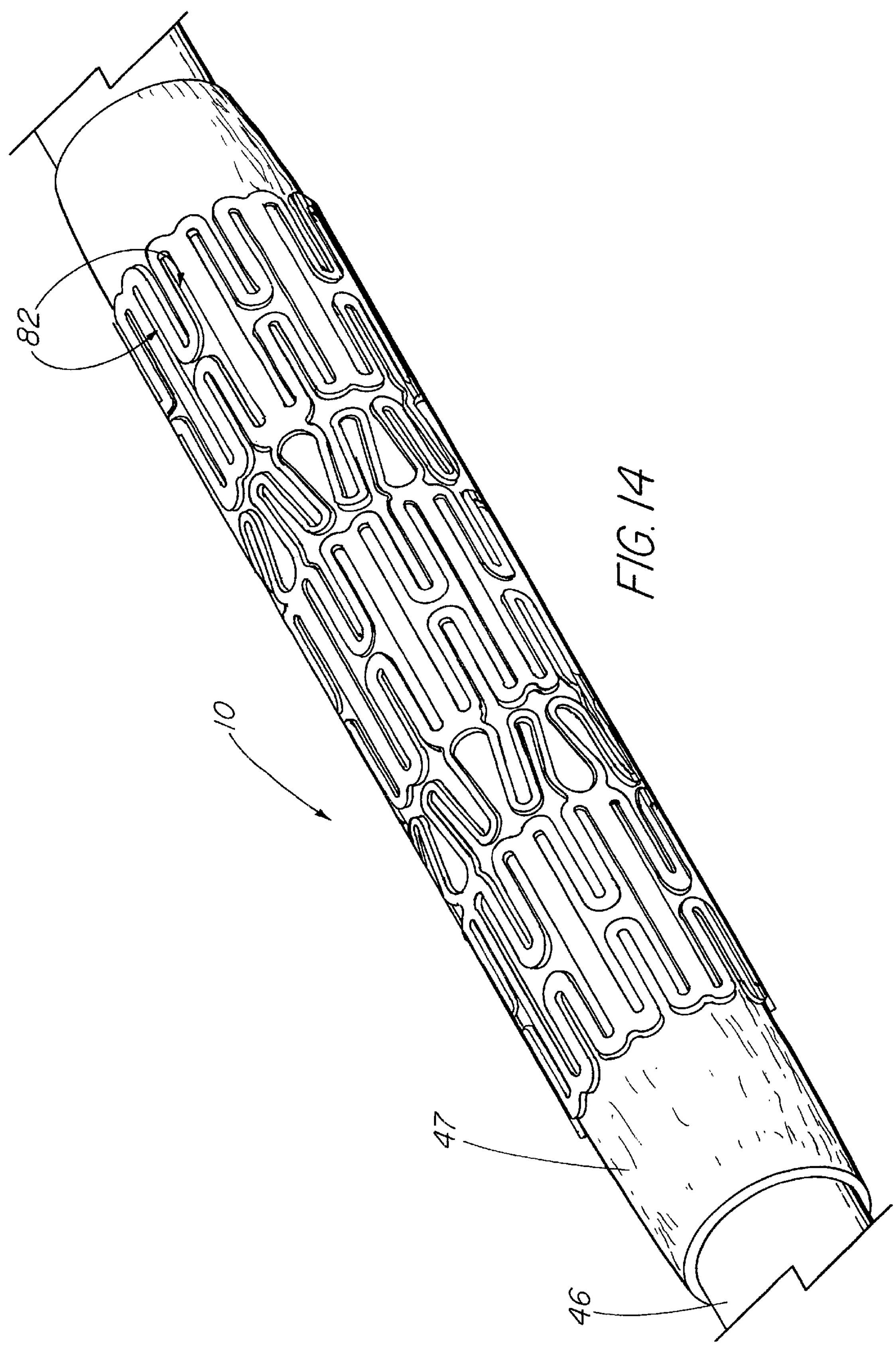
FIG. 14

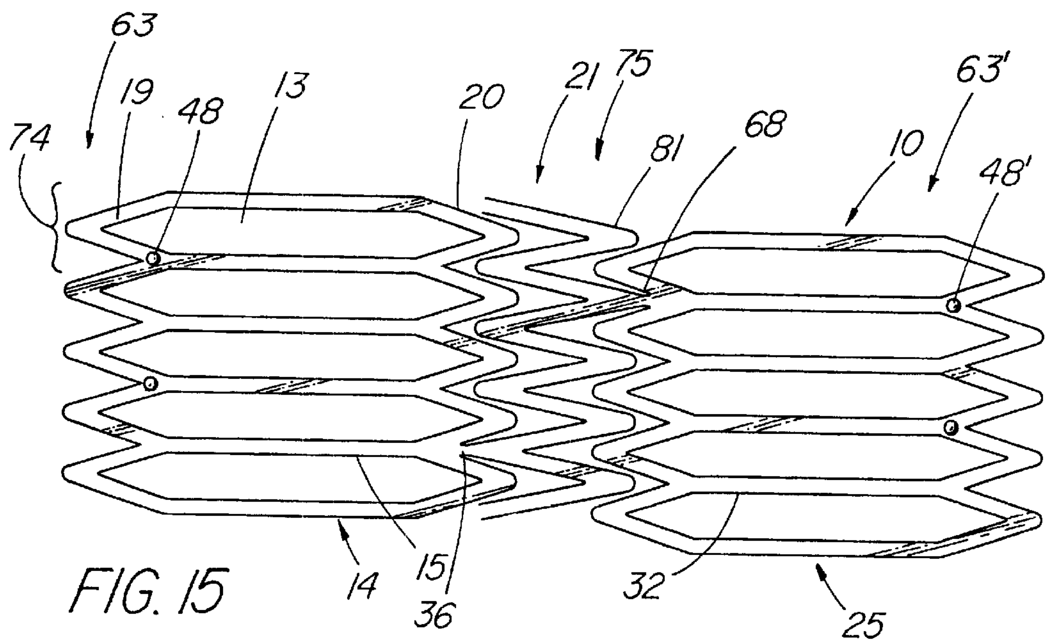
FIG. 15
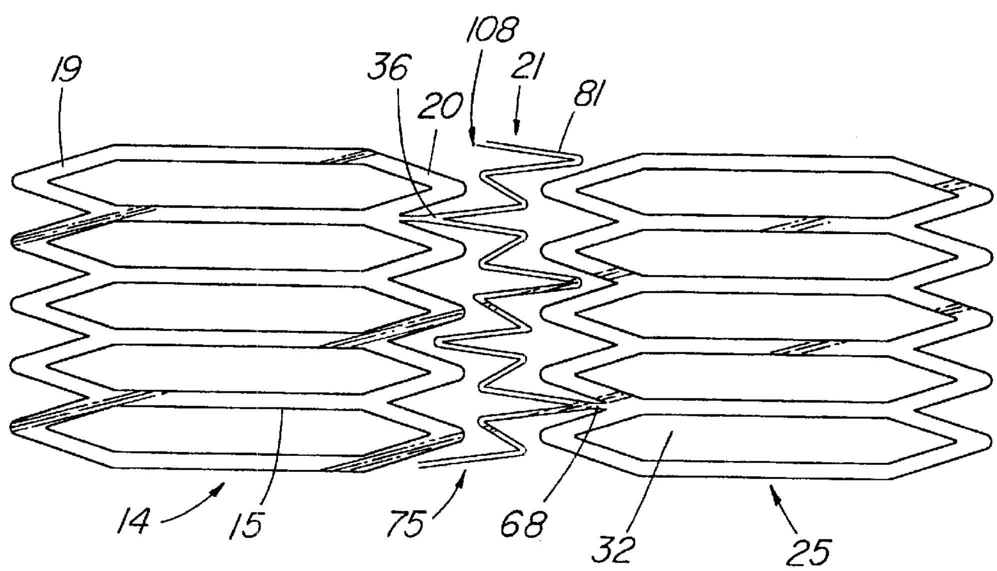
FIG. 16

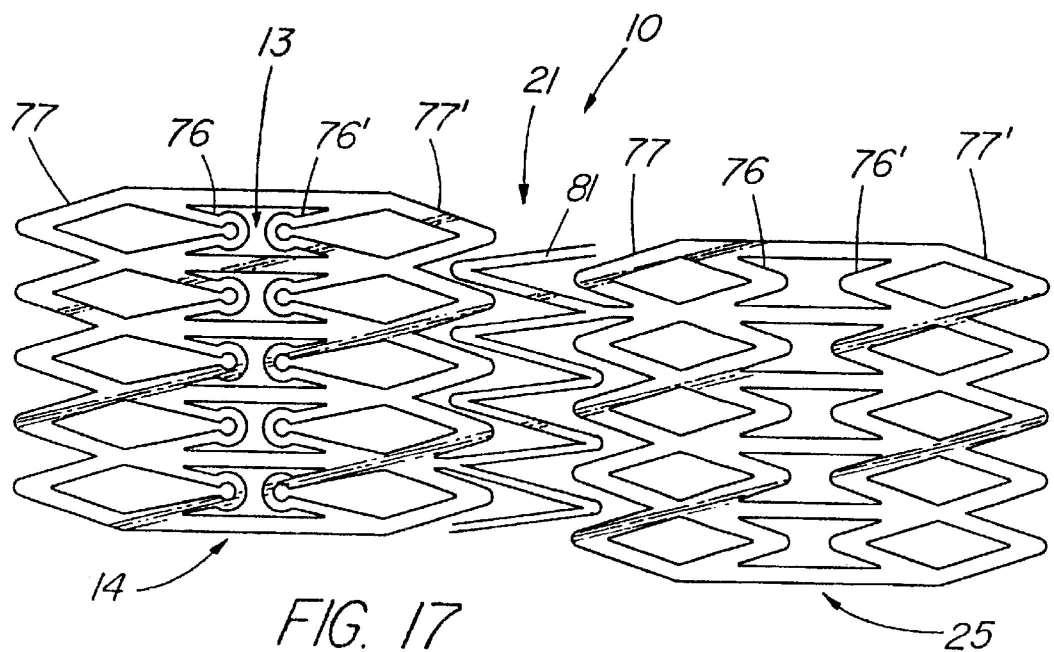
FIG. 17
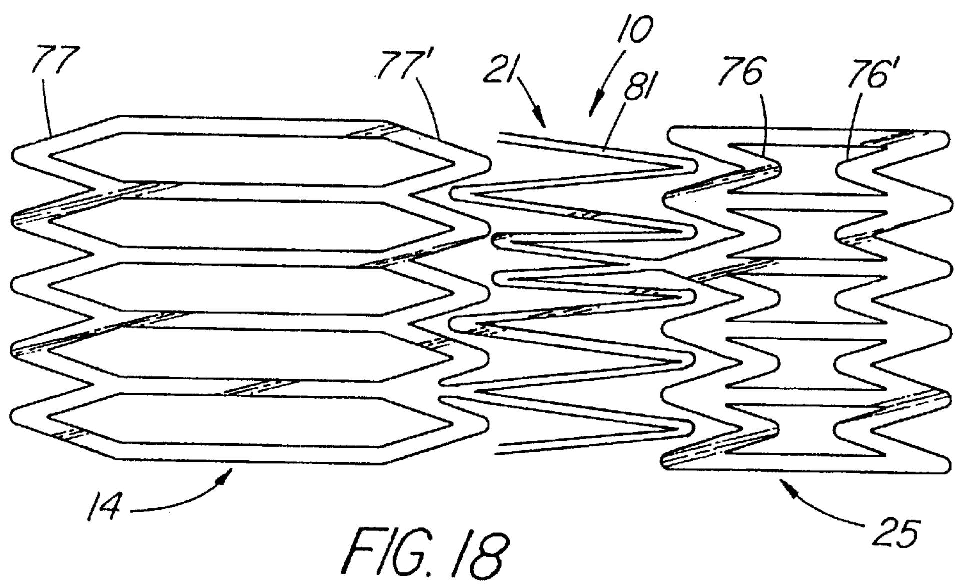
FIG. 18

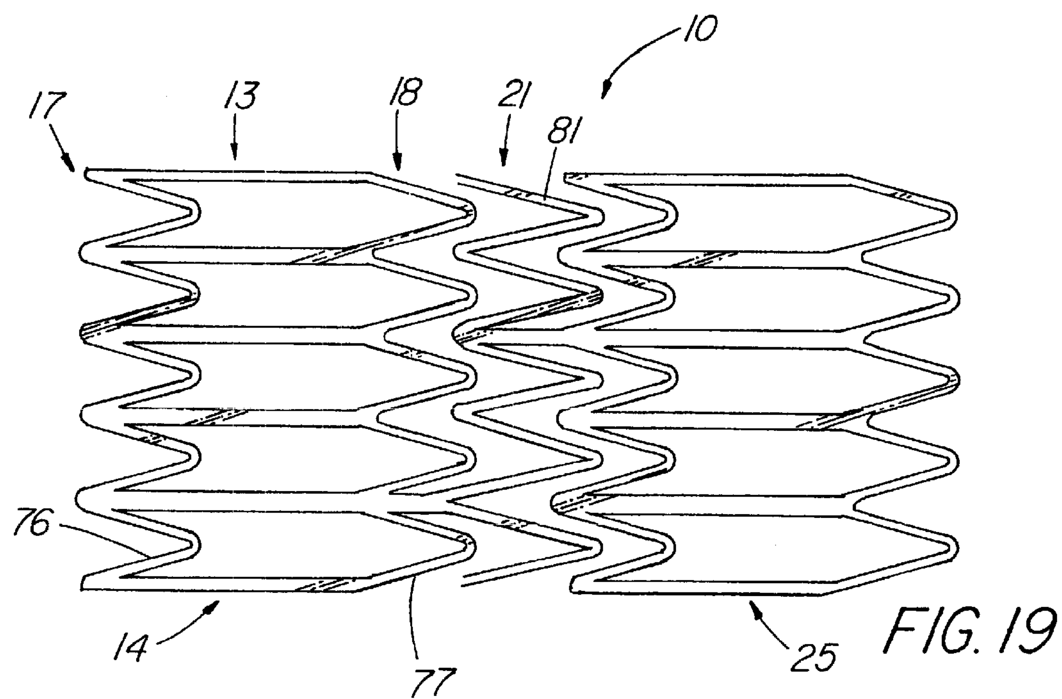
FIG. 19
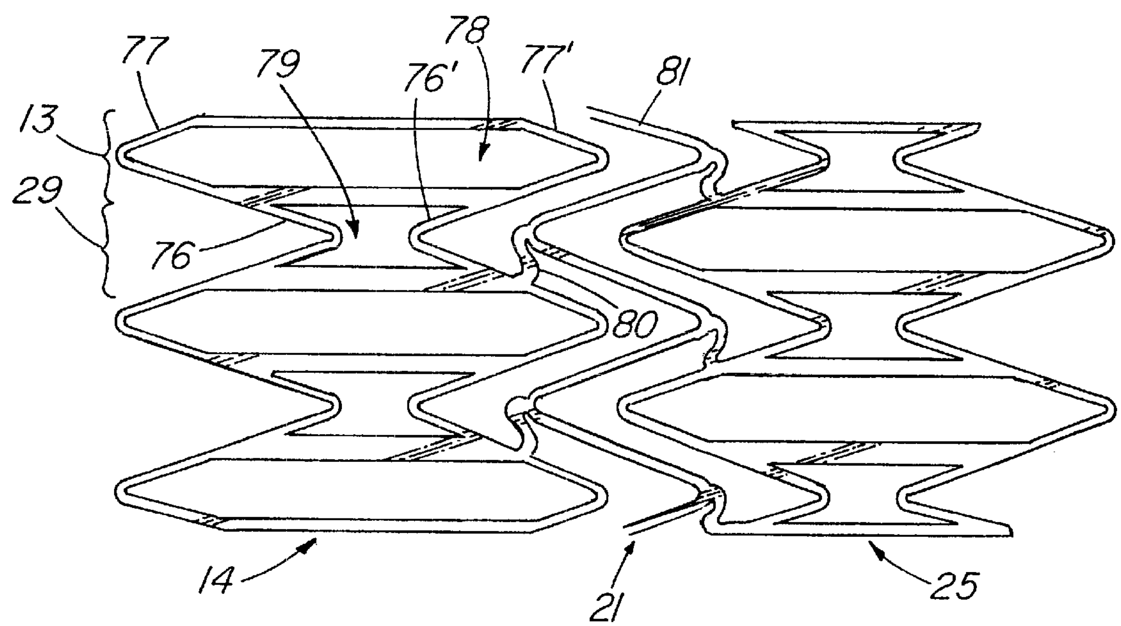
FIG. 20

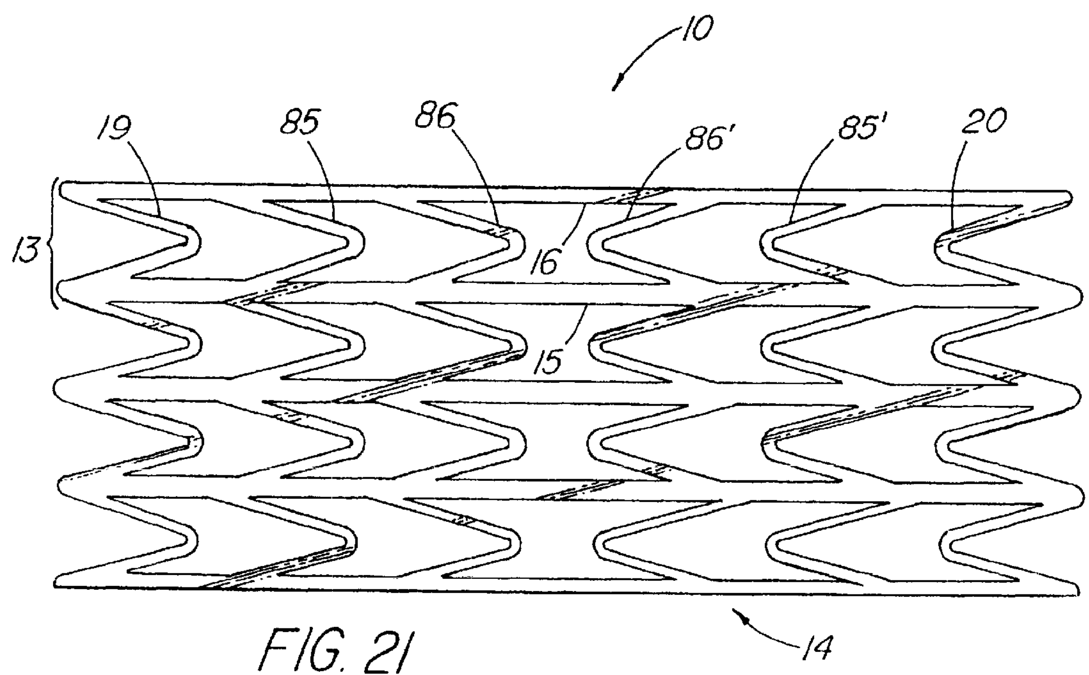
FIG. 21
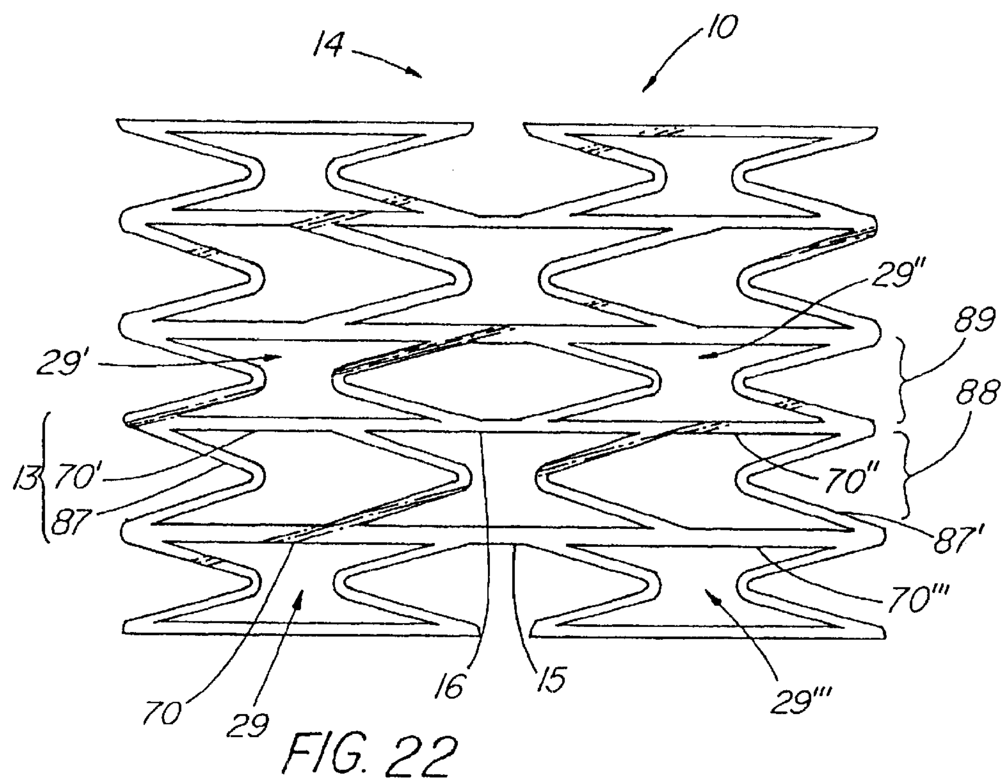
FIG. 22

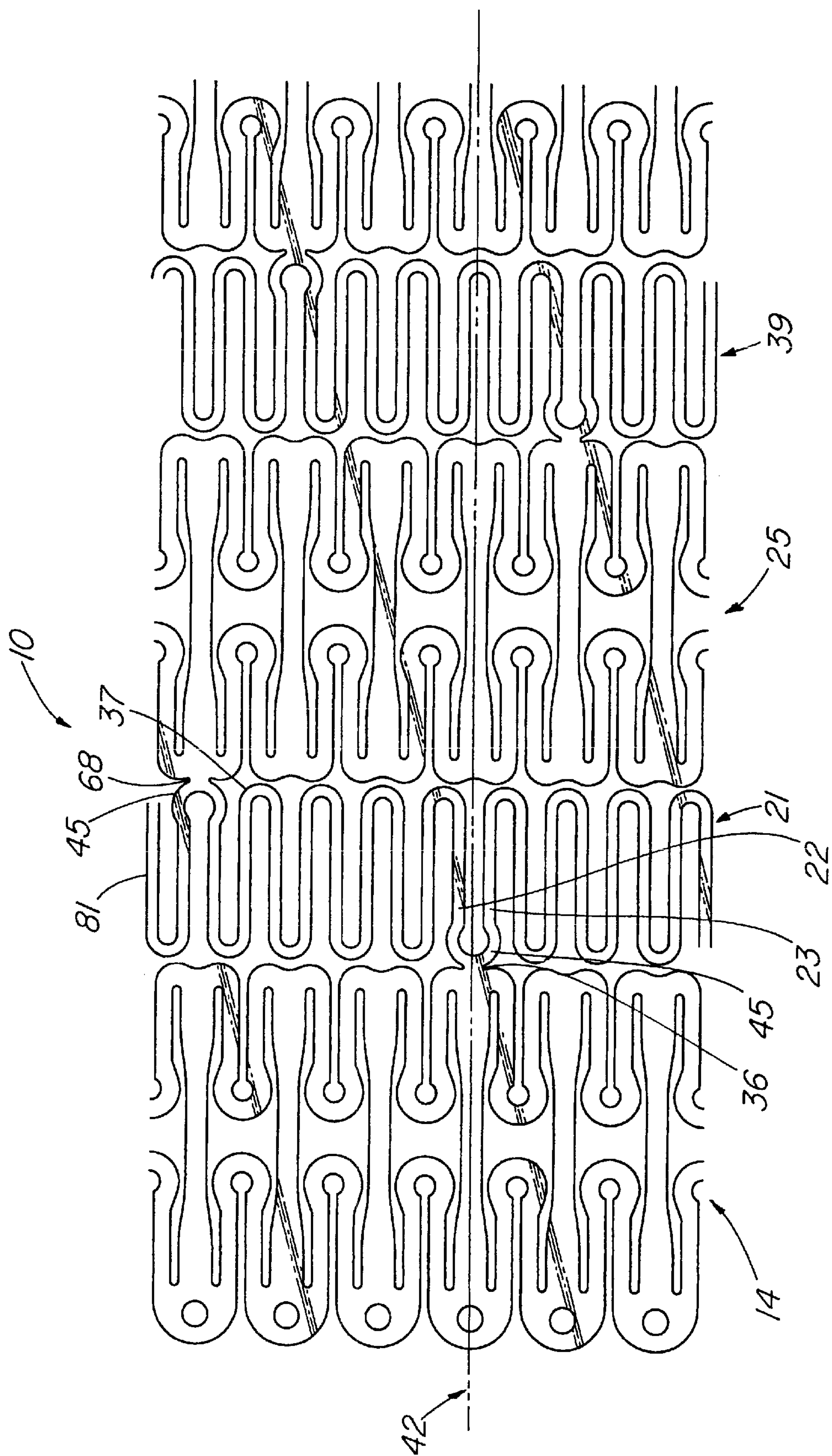
FIG. 23

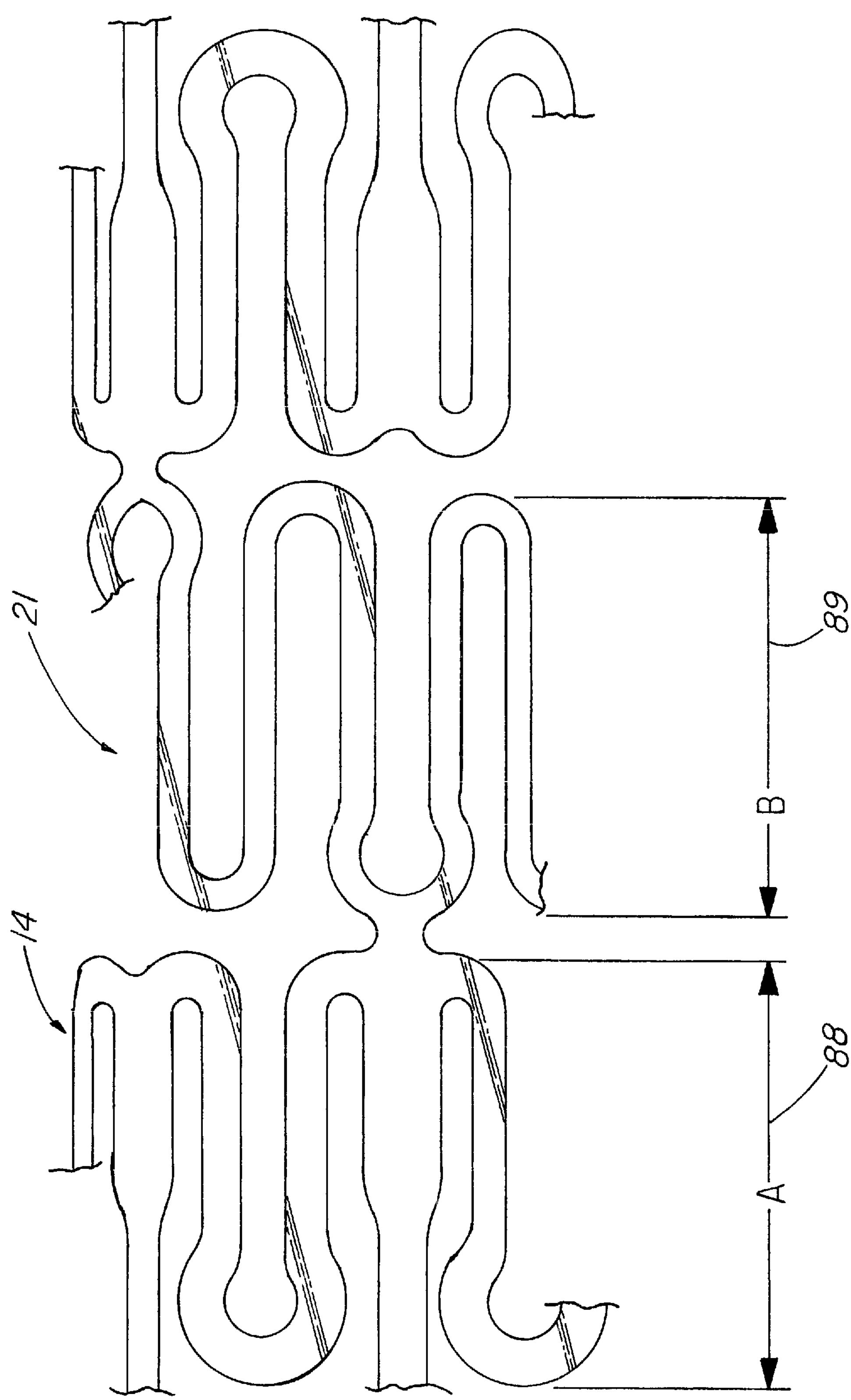
FIG. 24

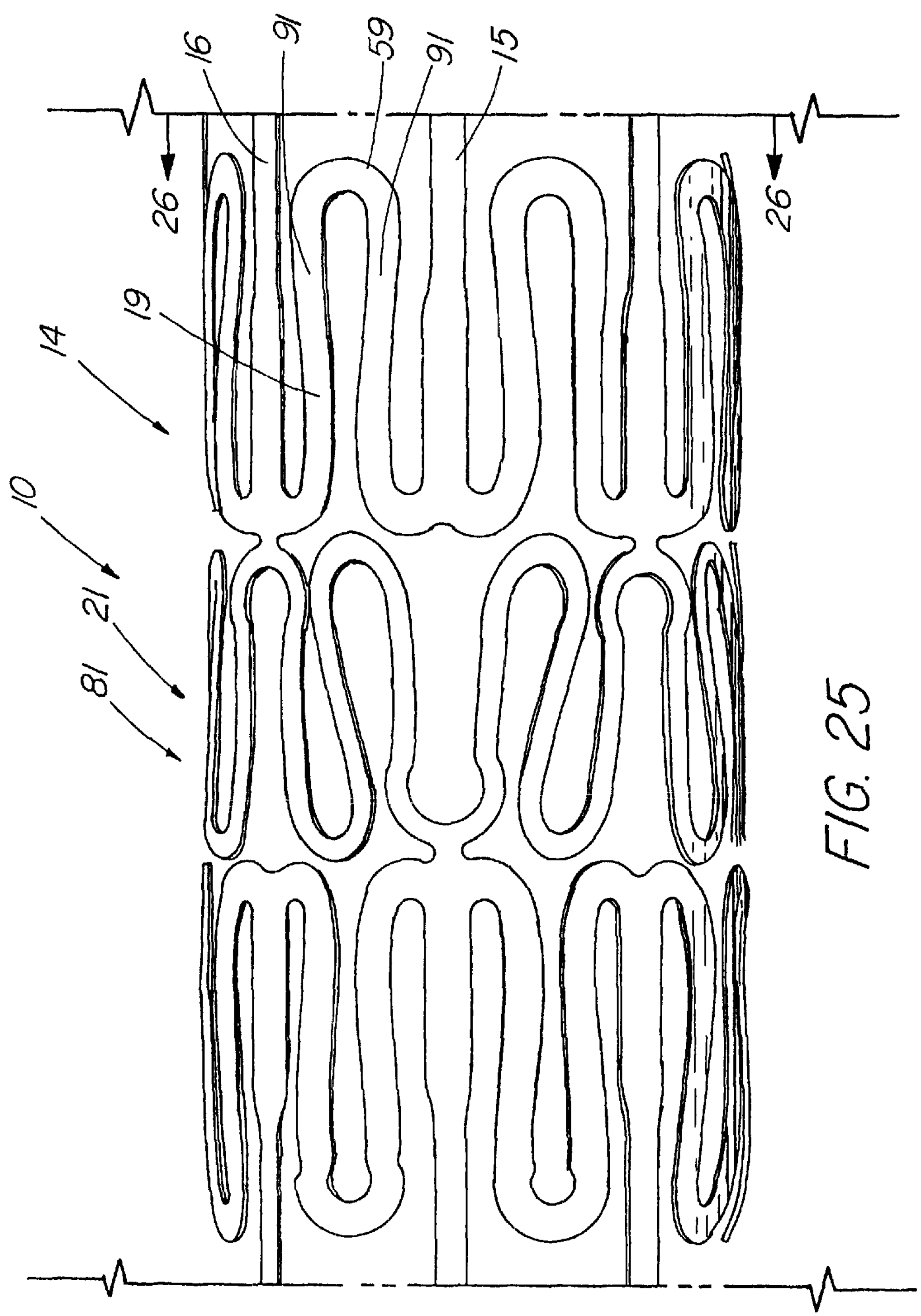
FIG. 25

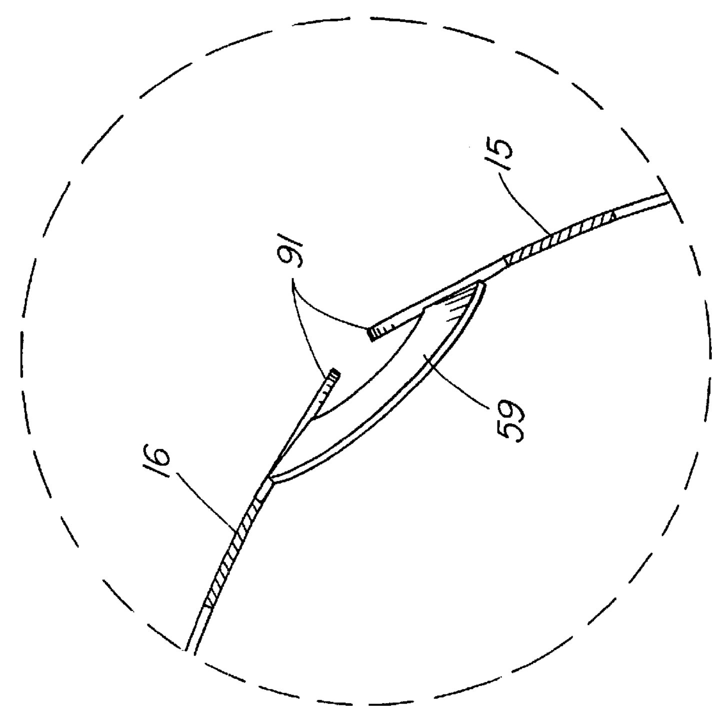
FIG. 27
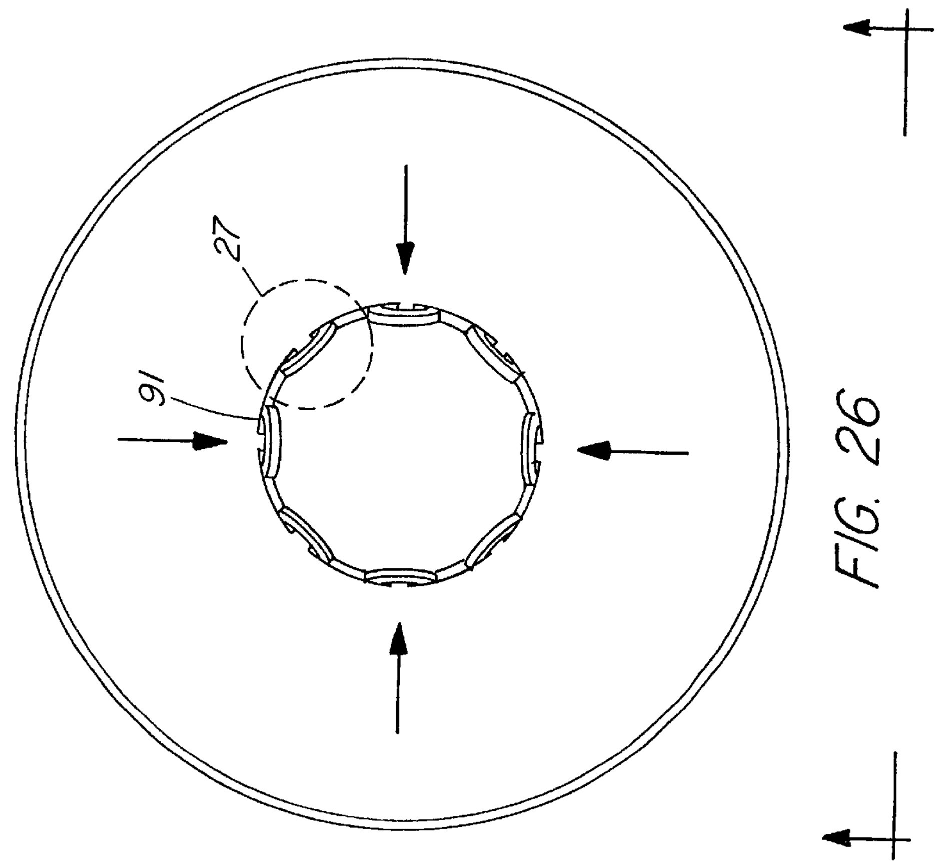
FIG. 26

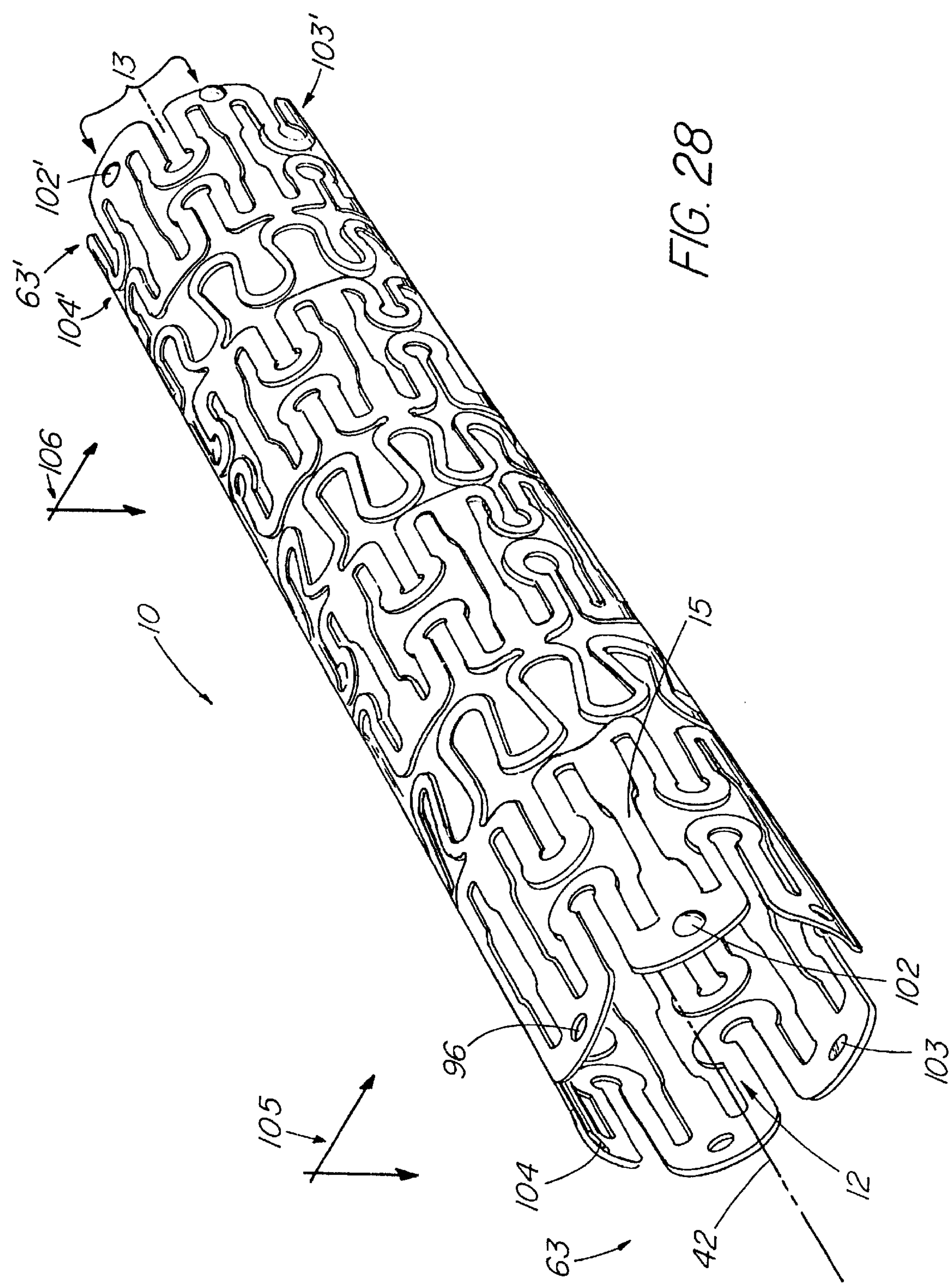
FIG. 28

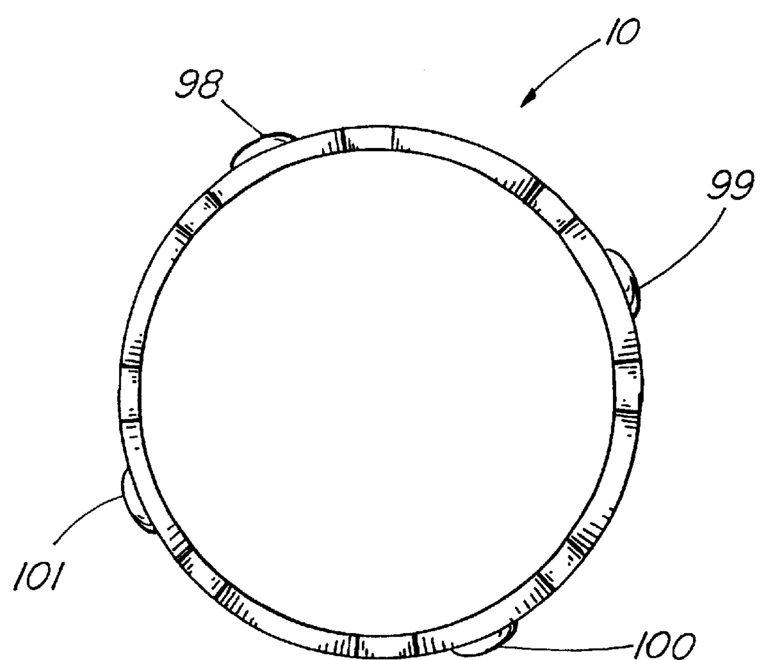
FIG. 29
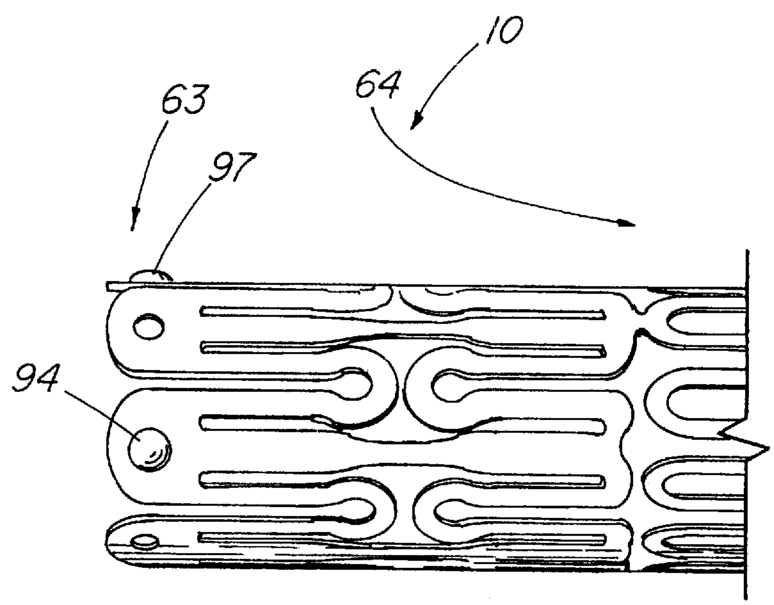
FIG. 30

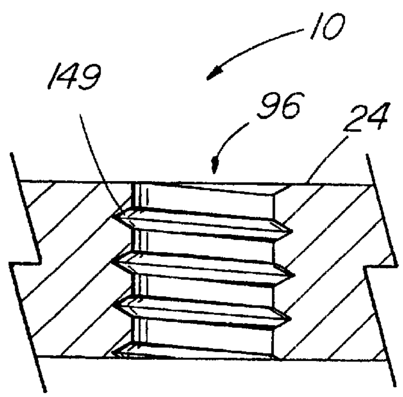
FIG. 31
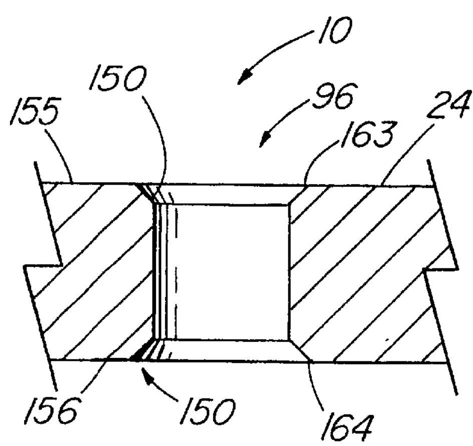
FIG. 32
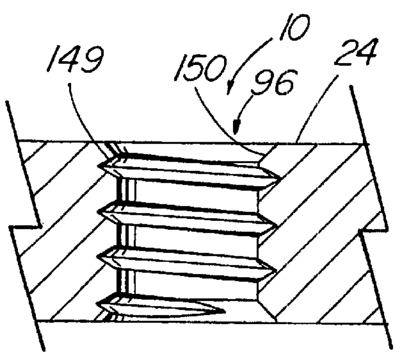
FIG. 33
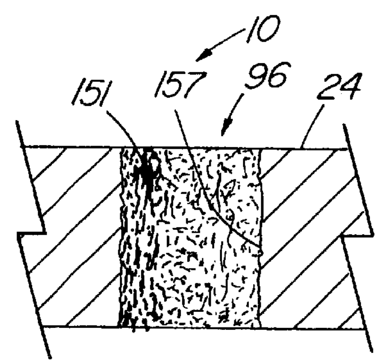
FIG. 34
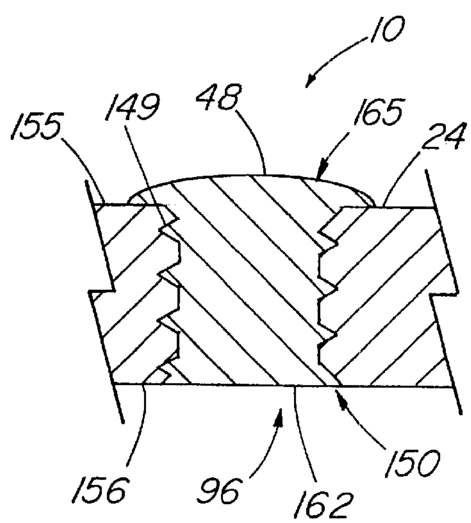
FIG. 35

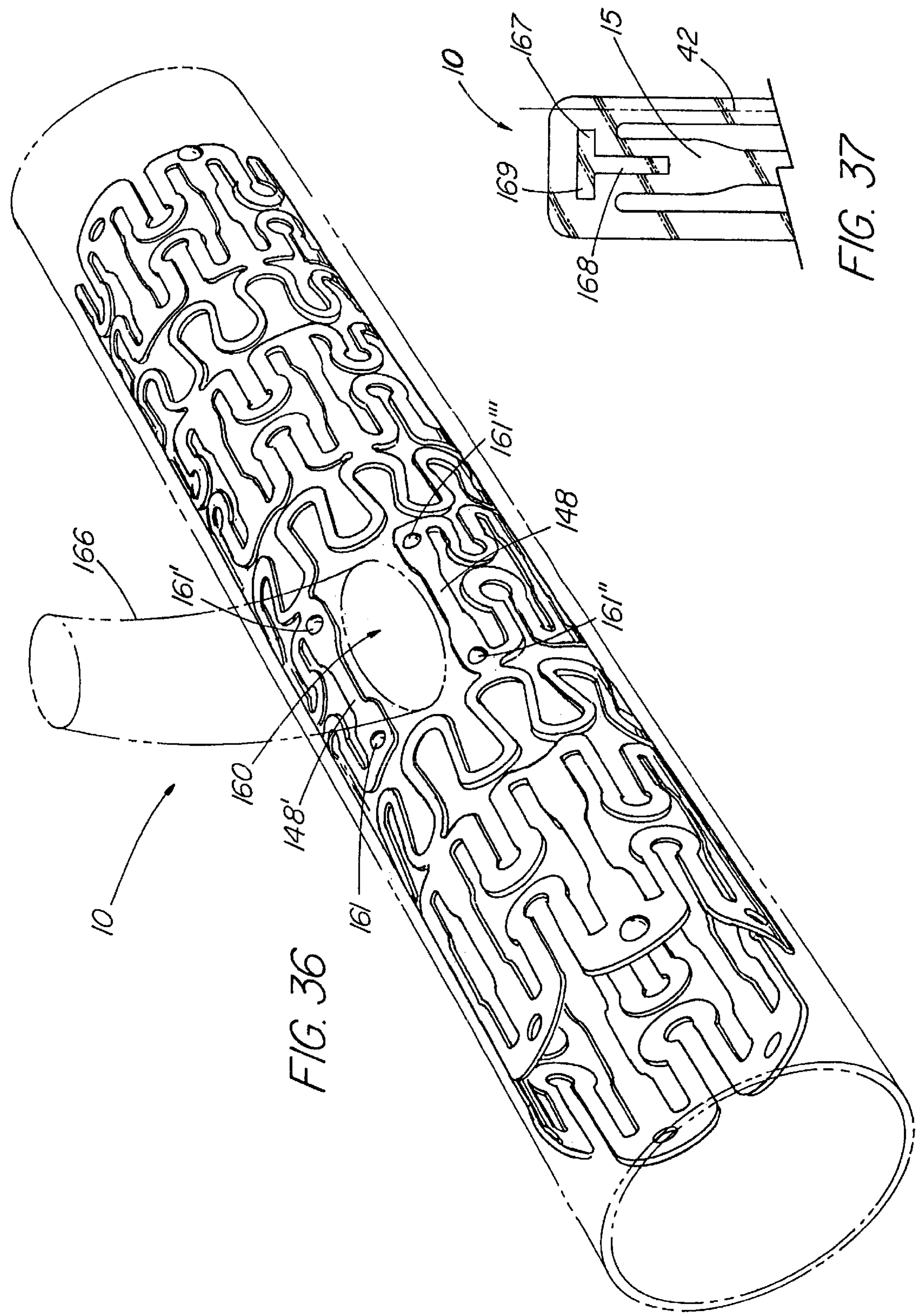
FIG. 36
FIG. 37

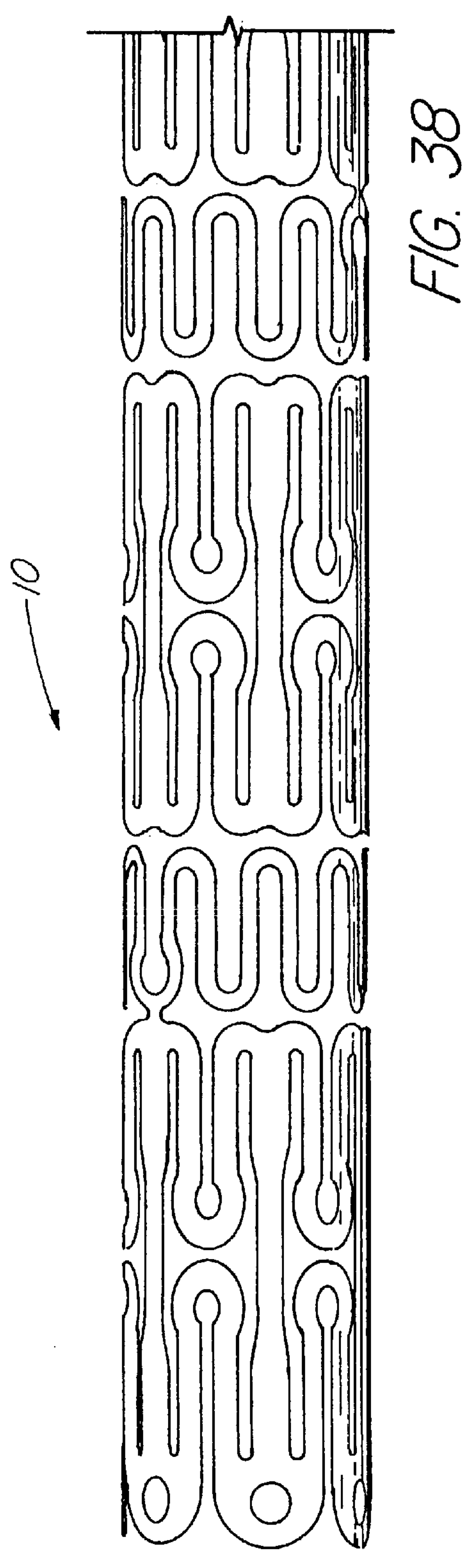
FIG. 38
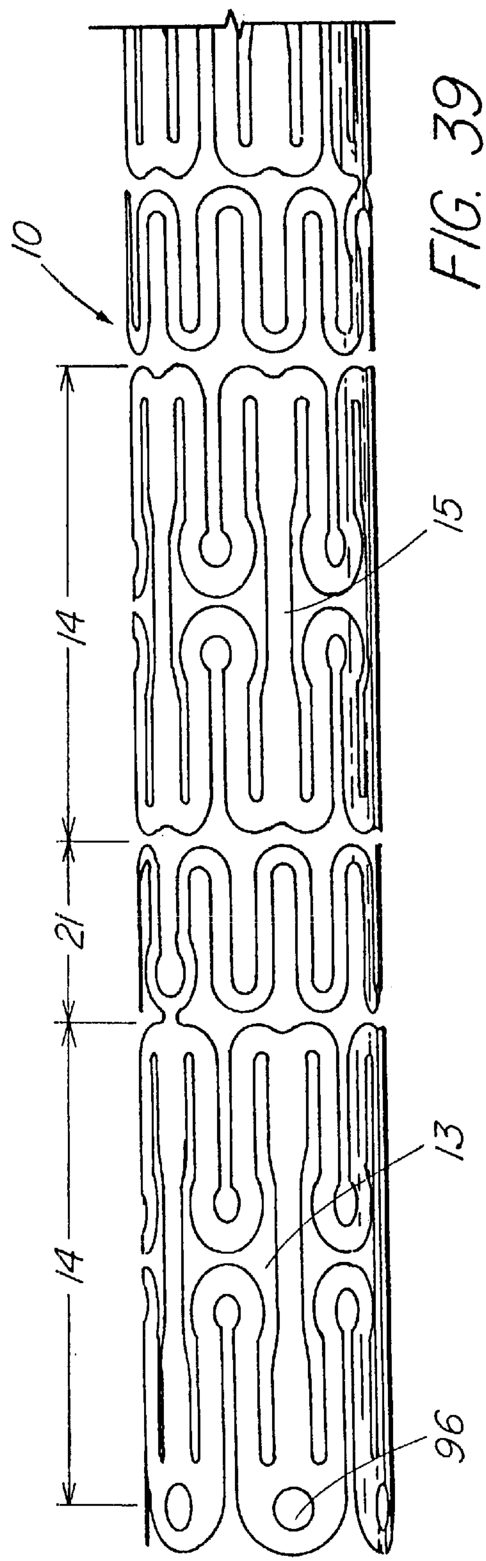
FIG. 39

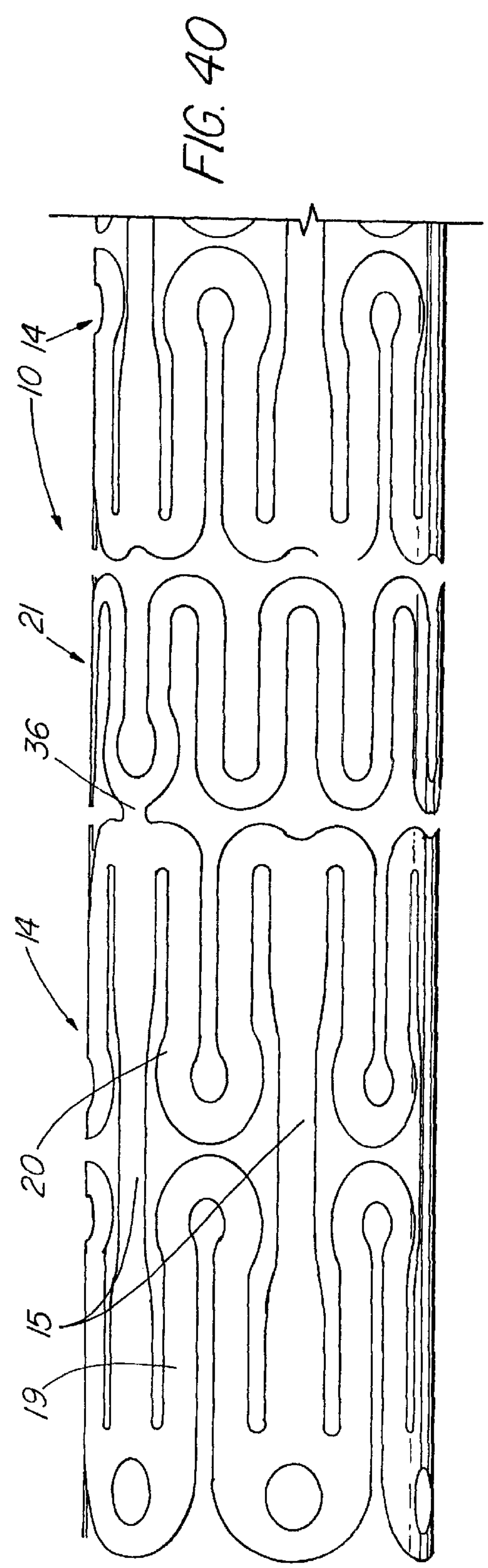
FIG. 40
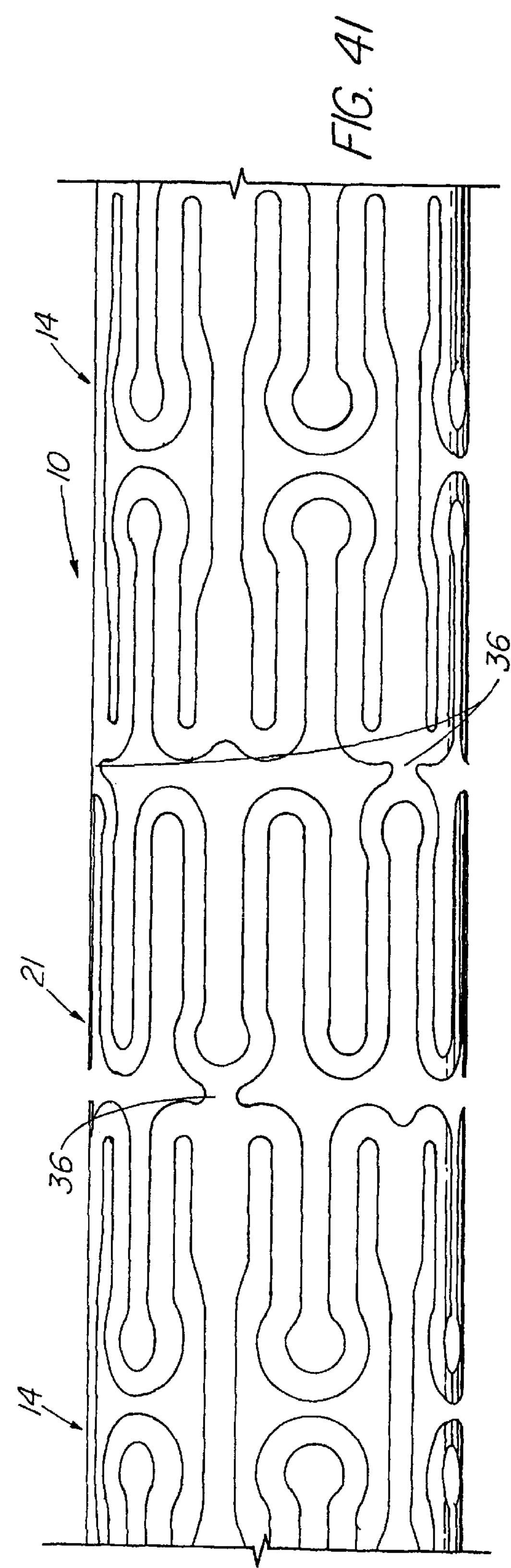
FIG. 41

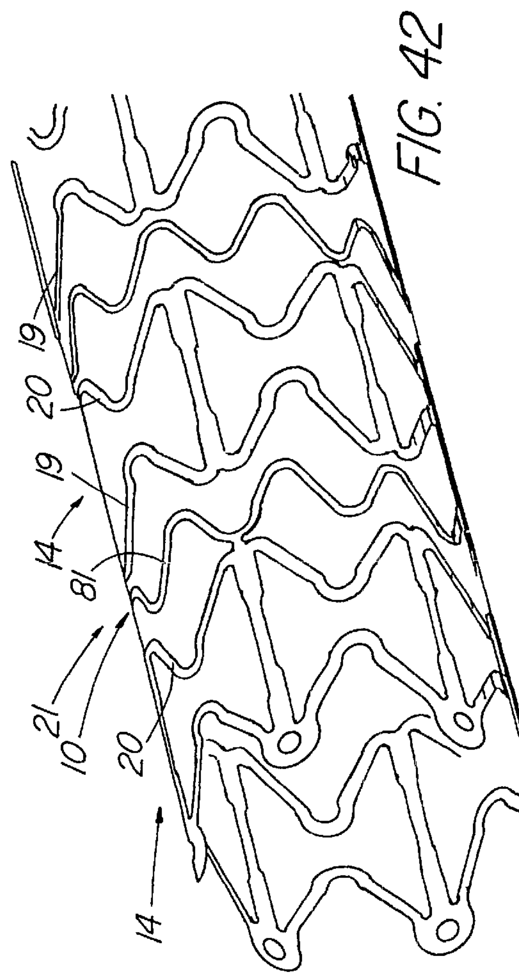
FIG. 42
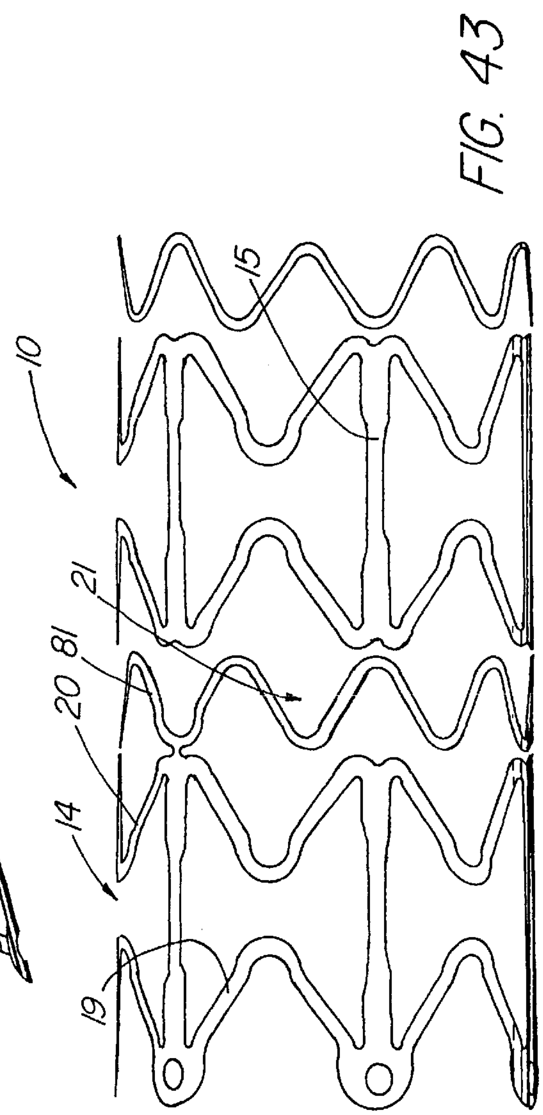
FIG. 43

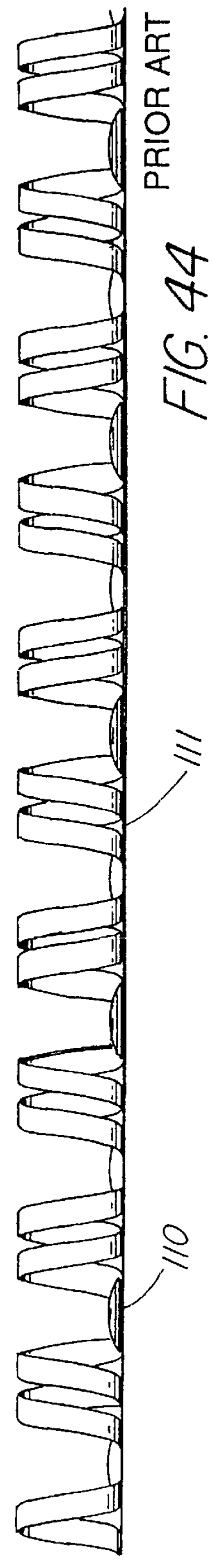
FIG. 44
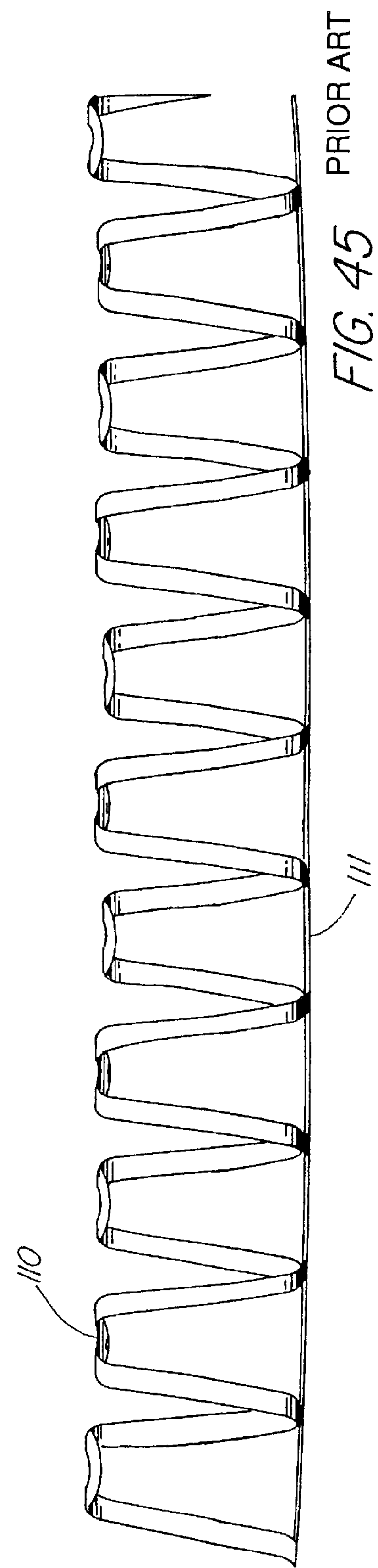
FIG. 45

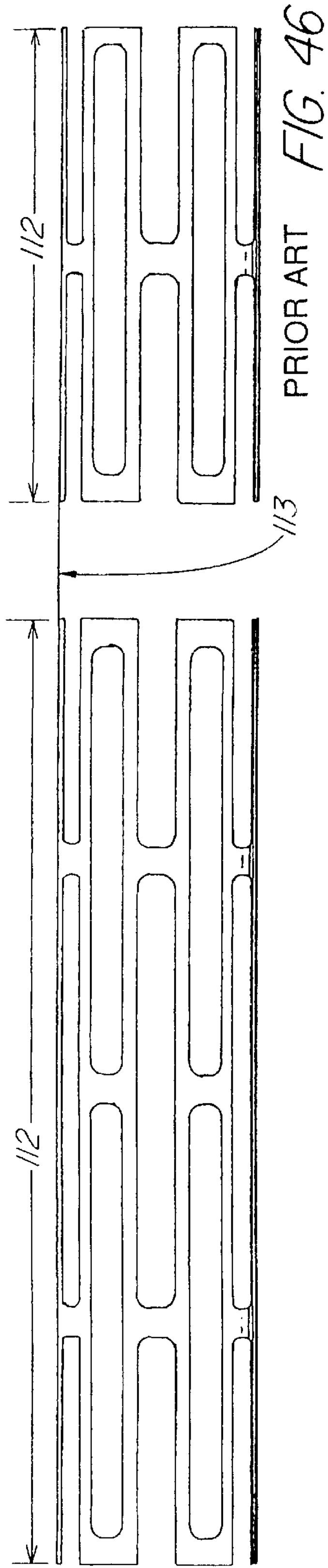
FIG. 46 PRIOR ART
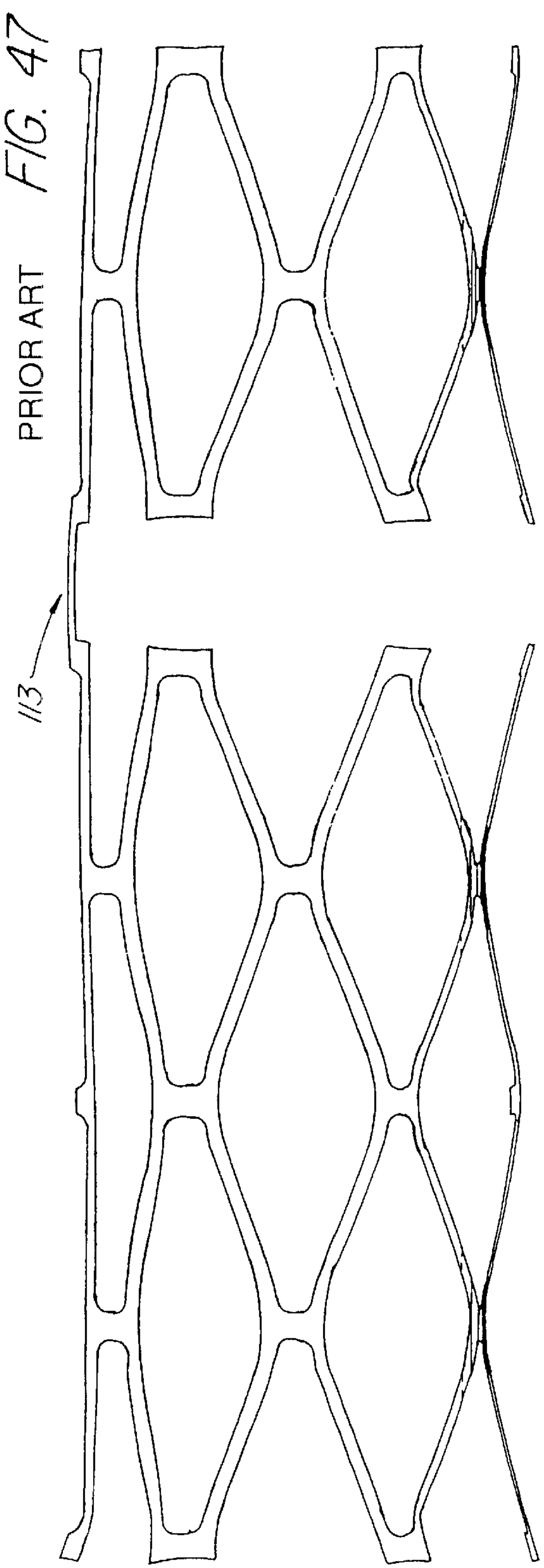
FIG. 47 PRIOR ART

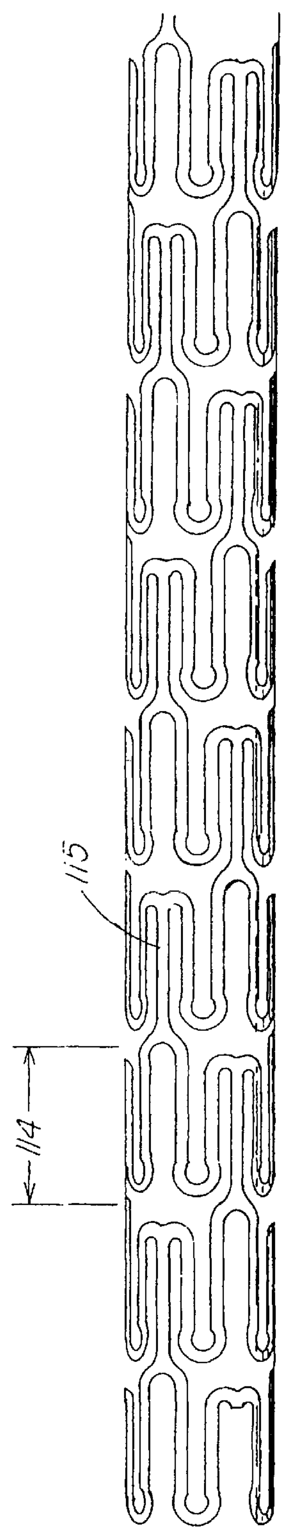
PRIOR ART FIG. 48
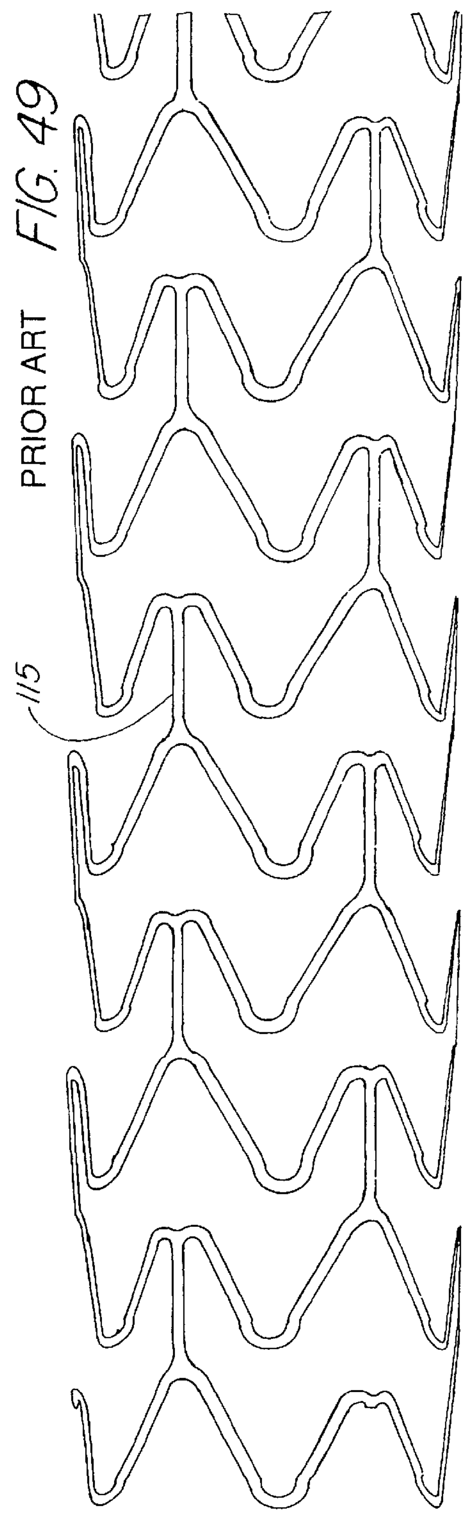
PRIOR ART FIG. 49

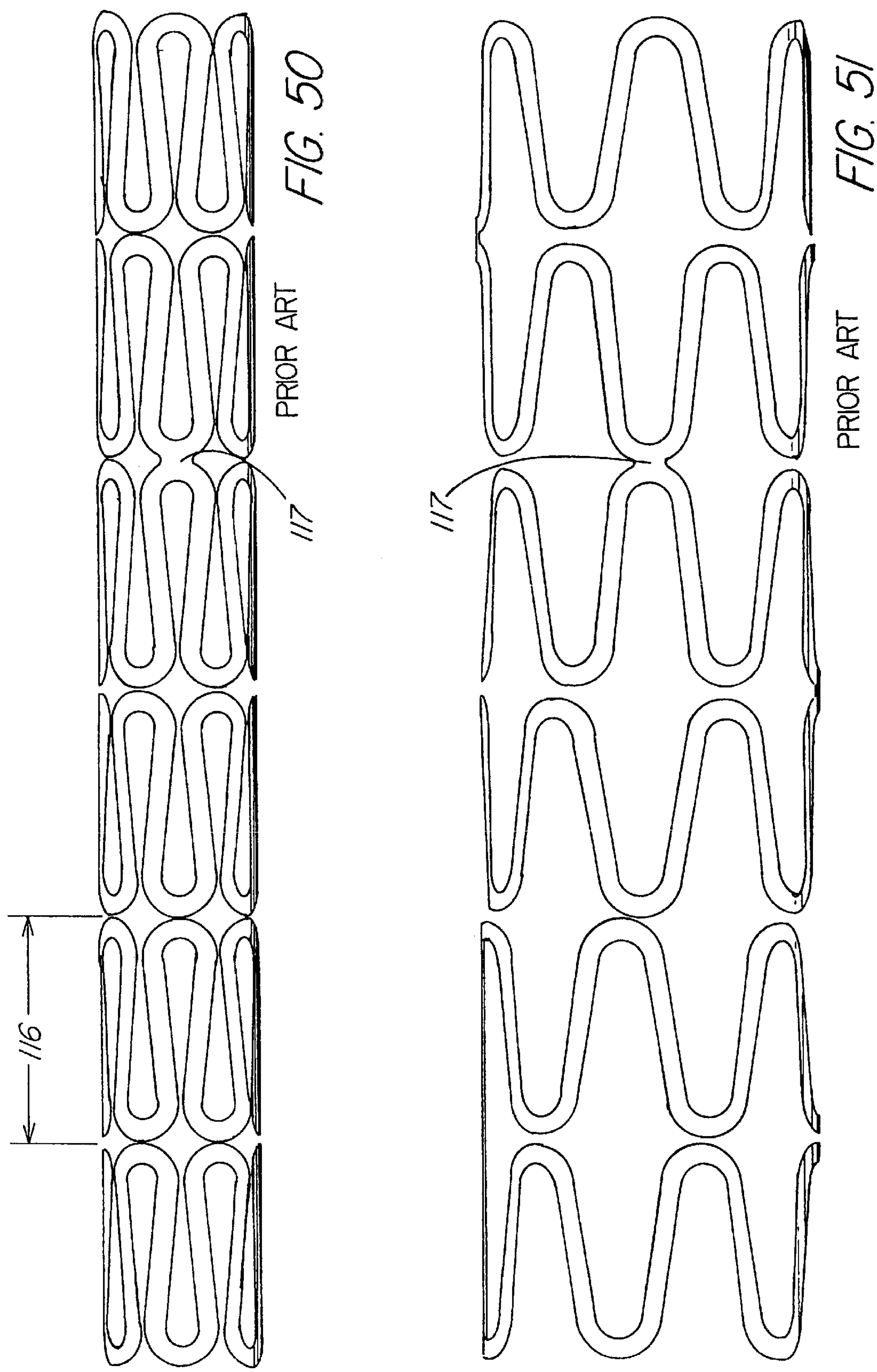
FIG. 50
PRIOR ART
117
116
FIG. 51
PRIOR ART
117

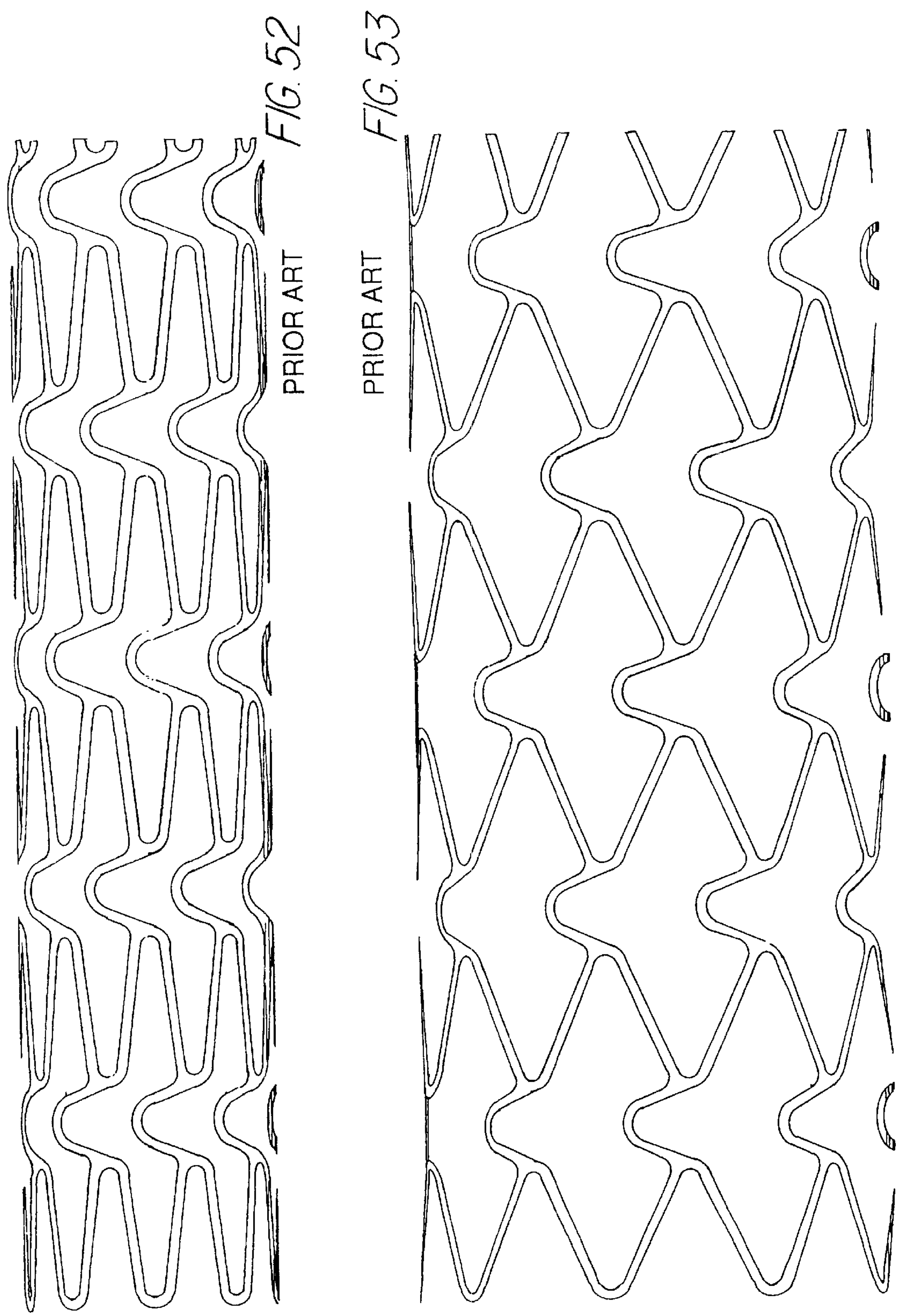
FIG. 52
PRIOR ART
FIG. 53
PRIOR ART

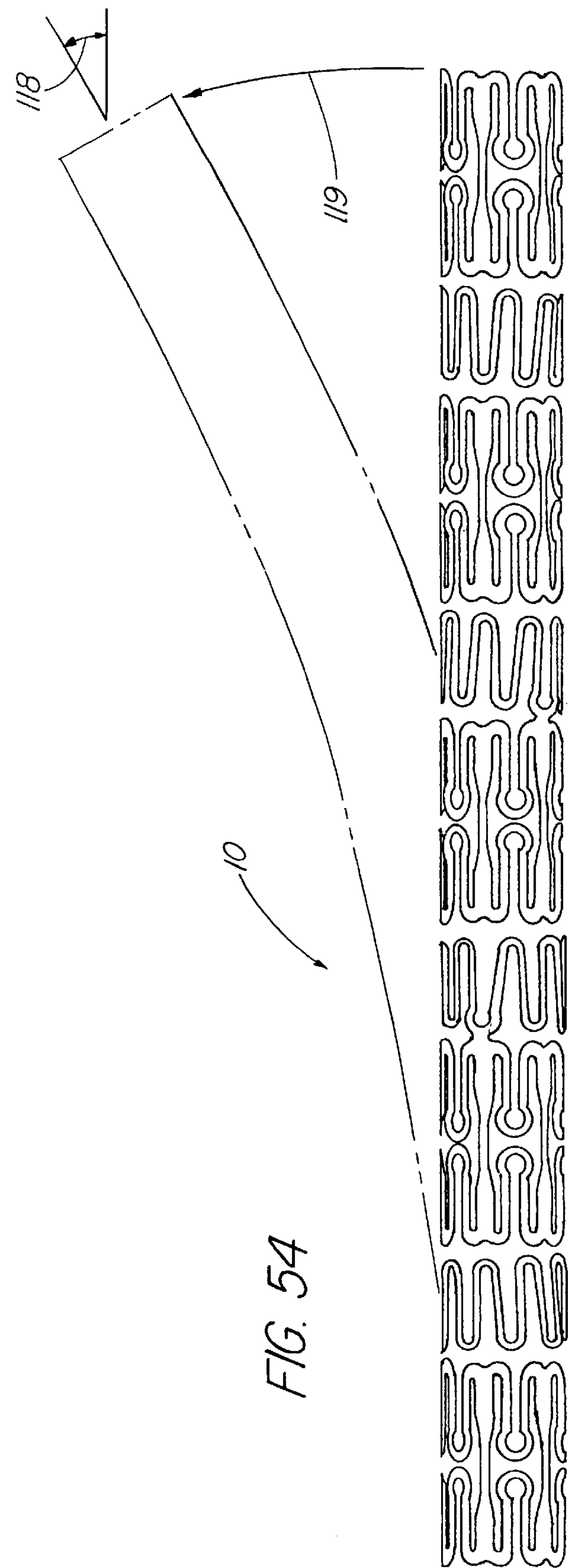
FIG. 54

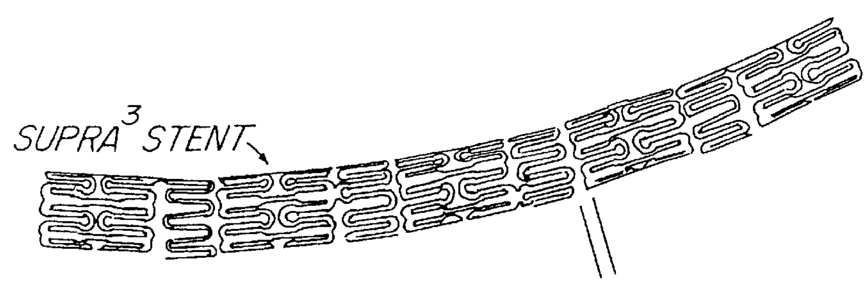
FIG. 55
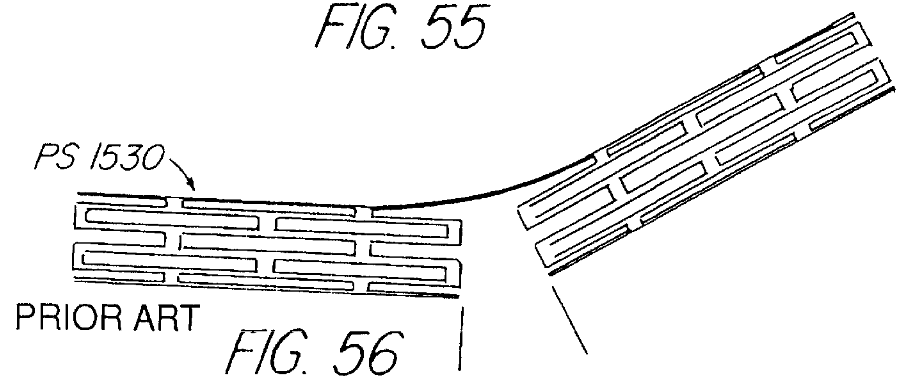
FIG. 56
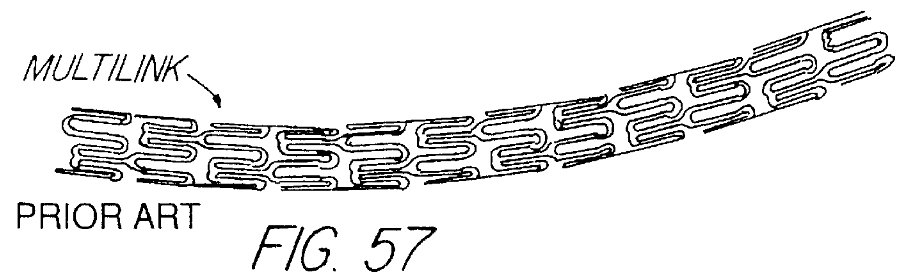
FIG. 57
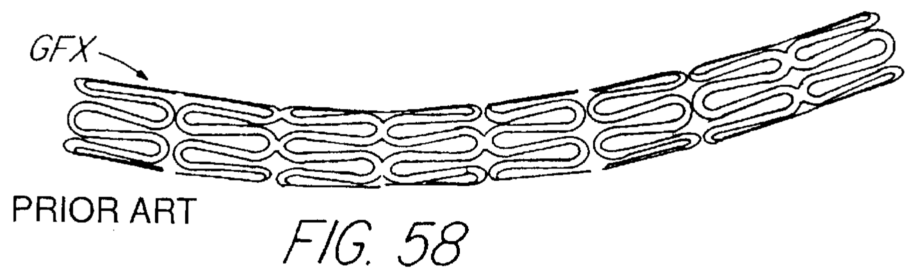
FIG. 58
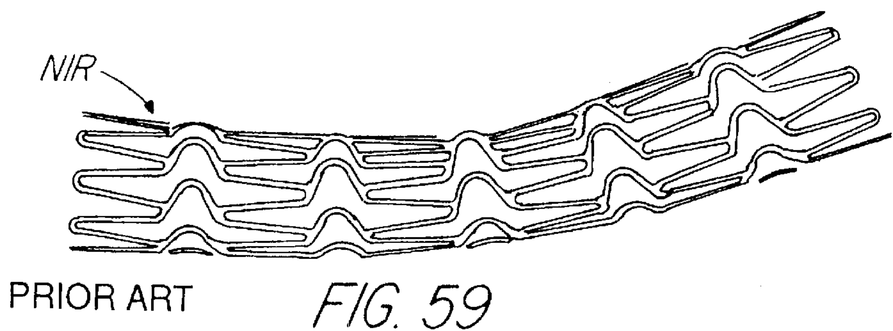
FIG. 59

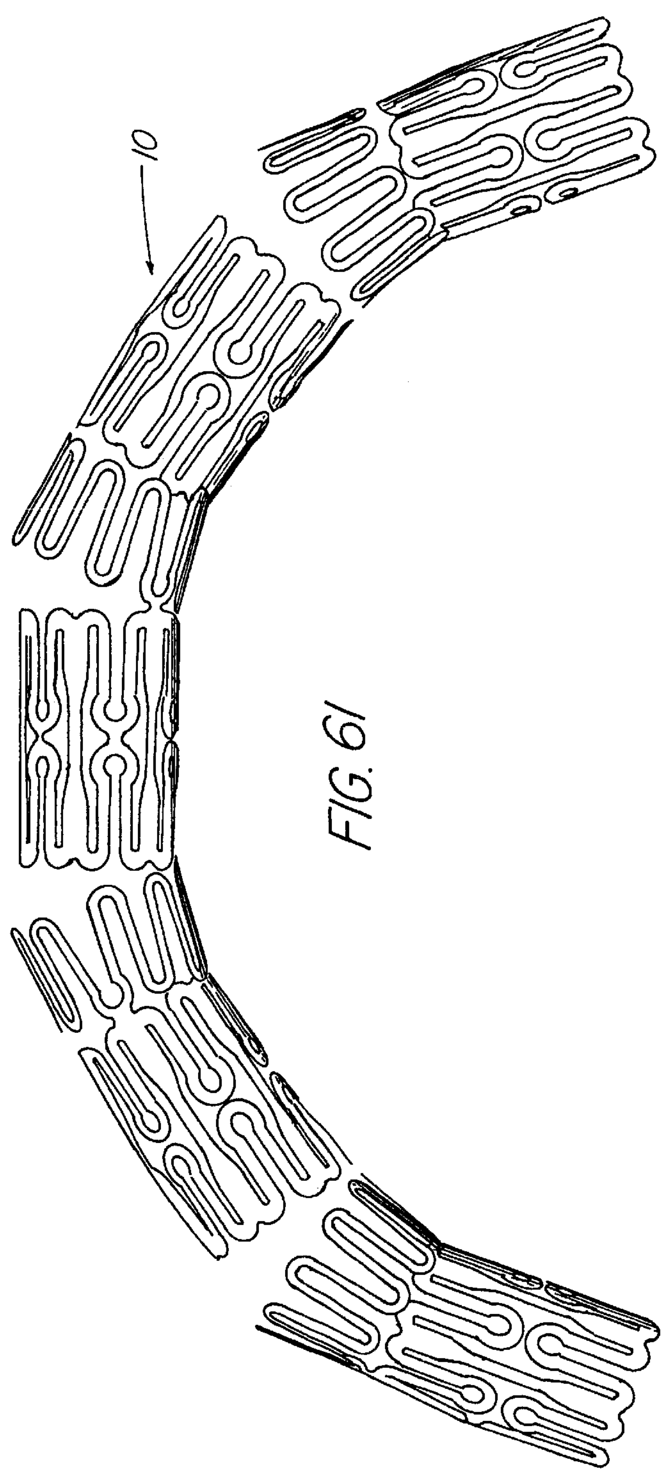
FIG. 61
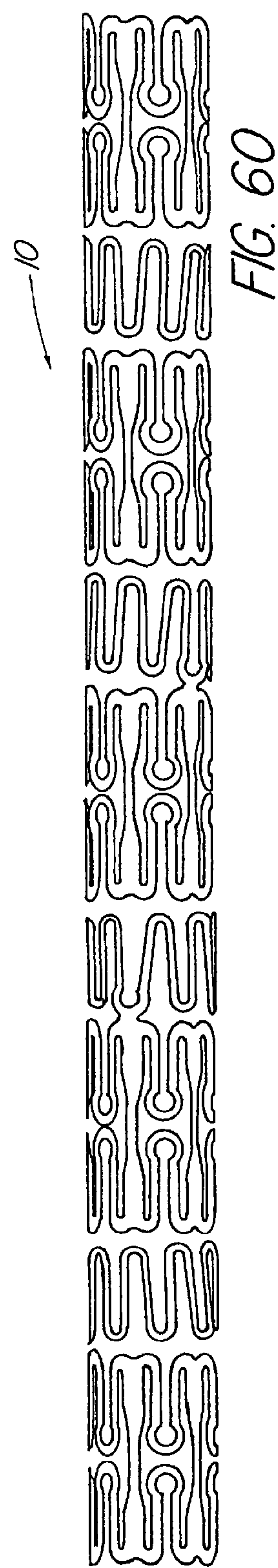
FIG. 60

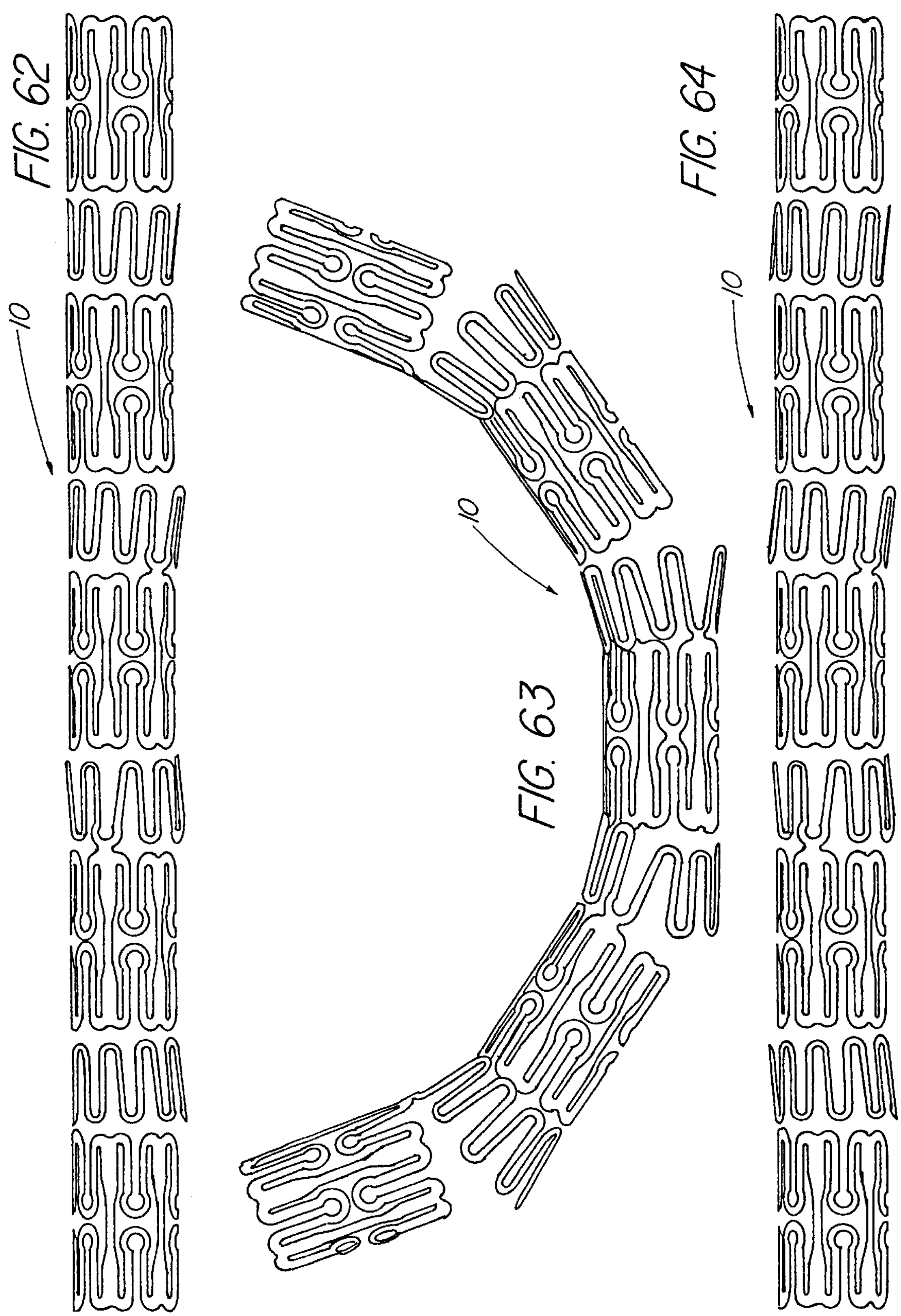
FIG. 62
10
FIG. 63
10
FIG. 64
10

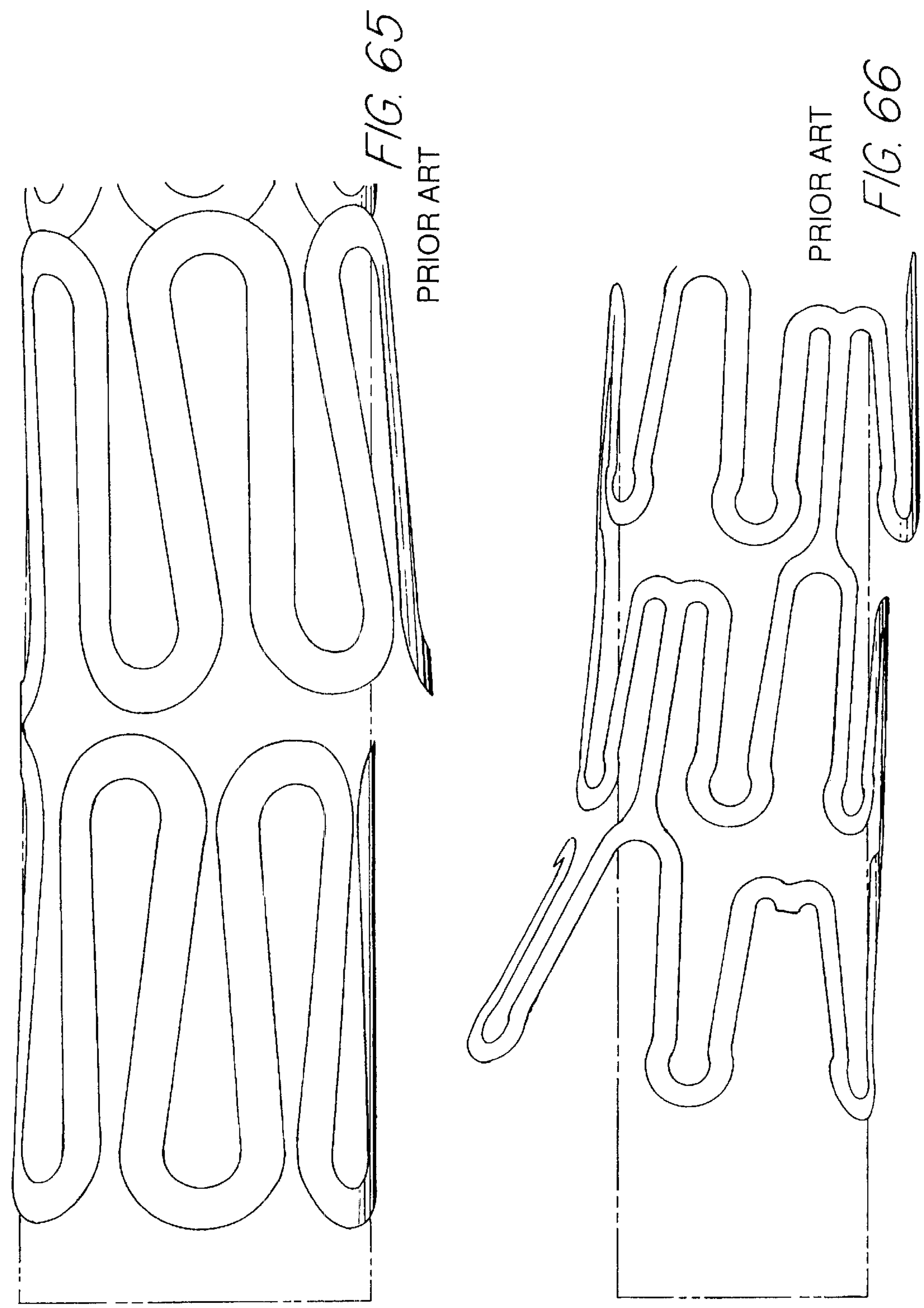
FIG. 65
PRIOR ART
FIG. 66
PRIOR ART

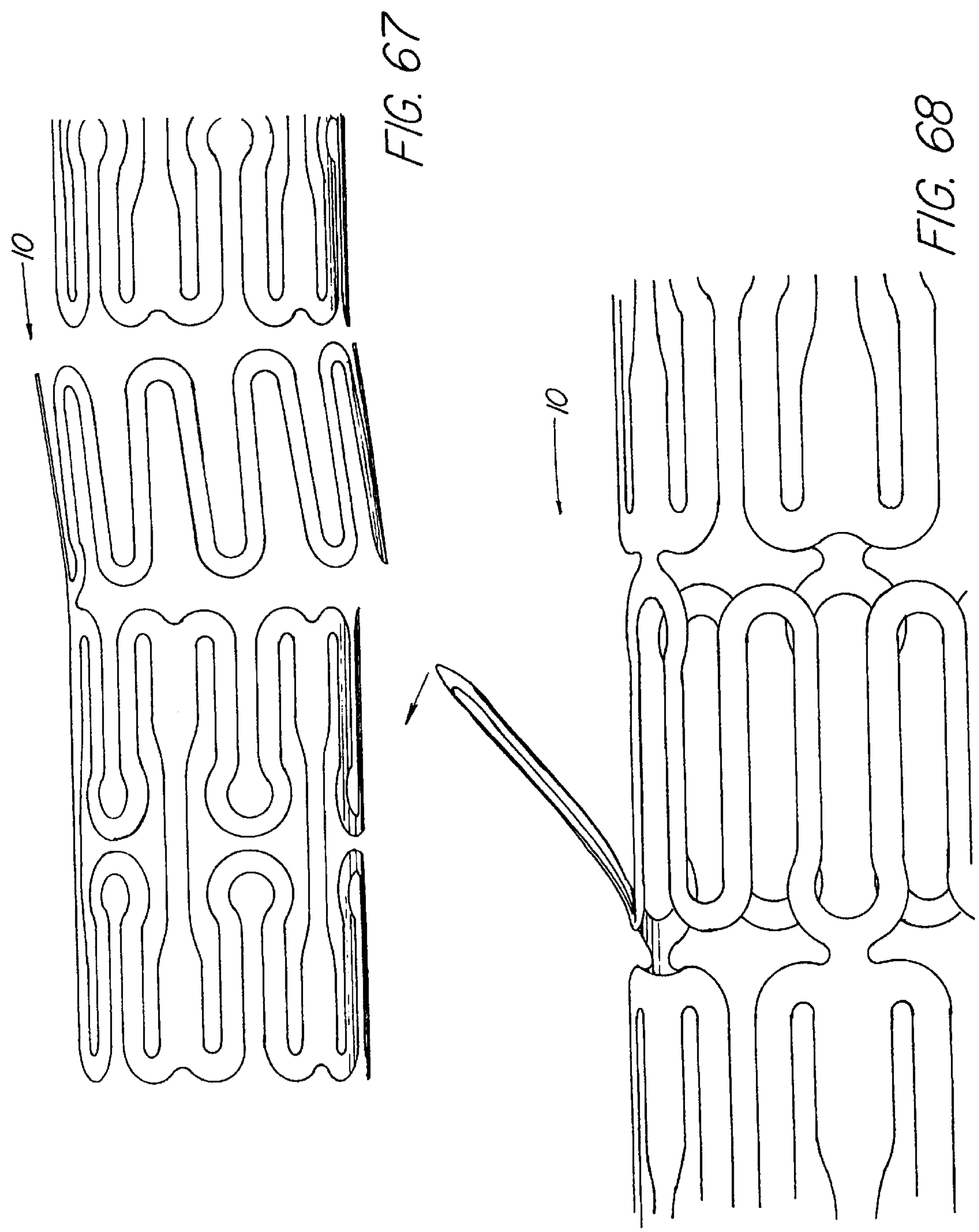
10
FIG. 67
10
FIG. 68

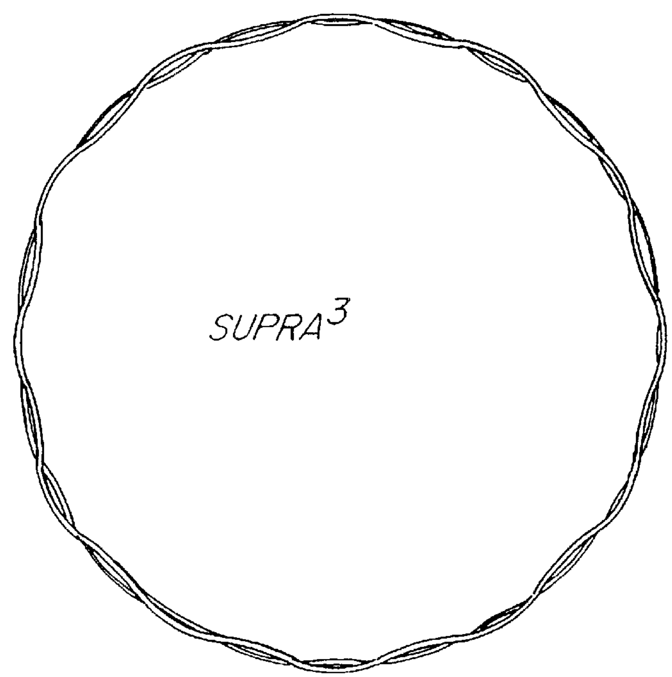
FIG. 69
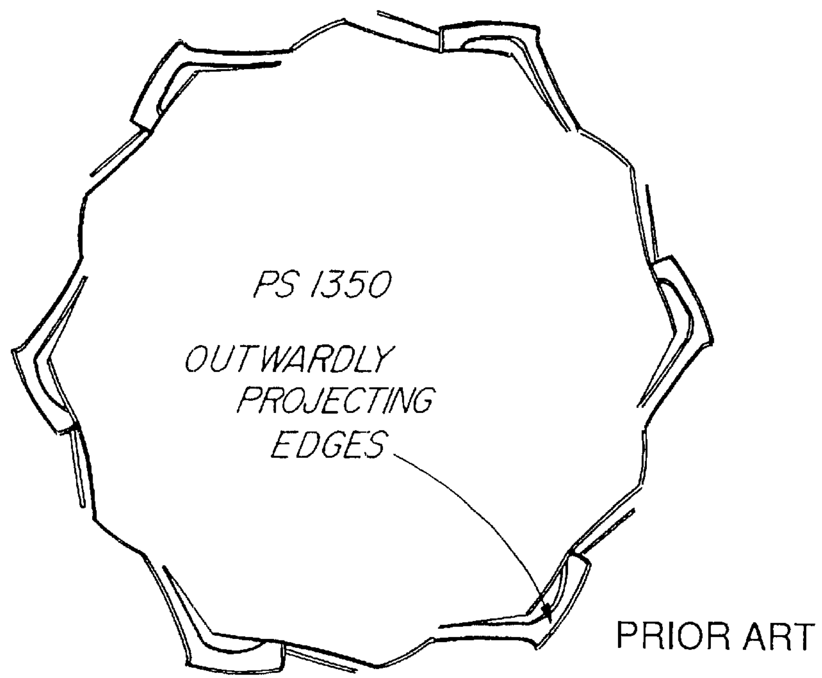
FIG. 70

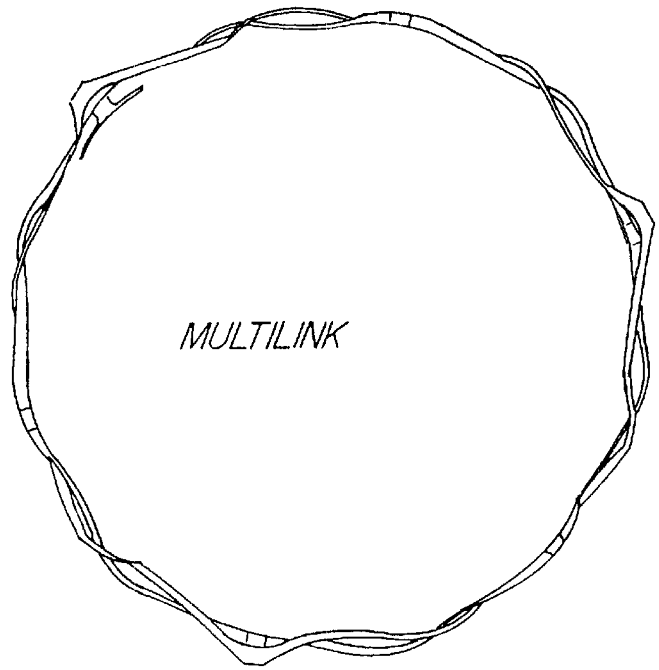
FIG. 71 PRIOR ART
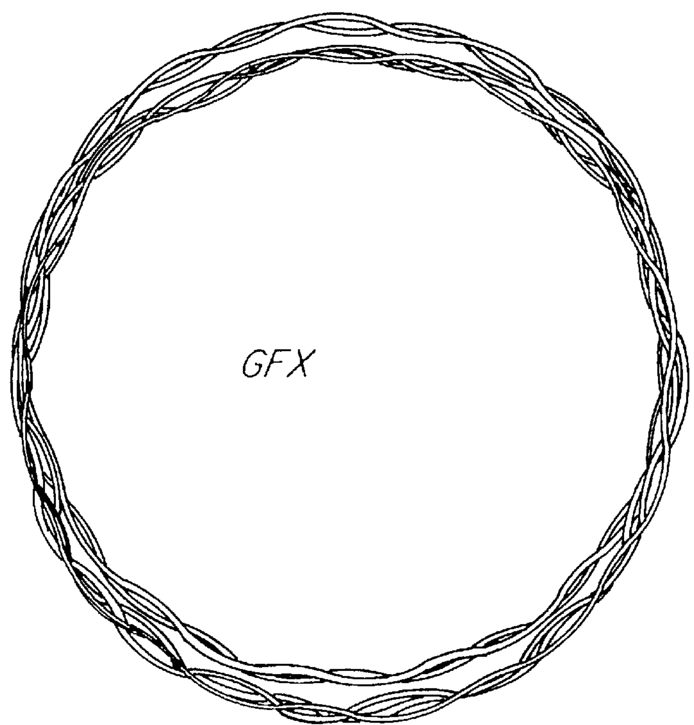
FIG. 72 PRIOR ART

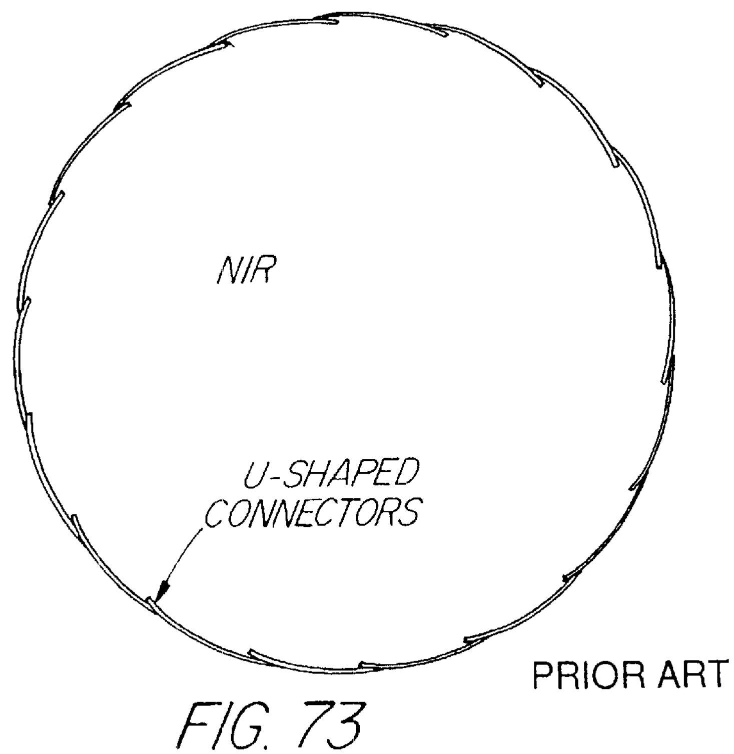
FIG. 73
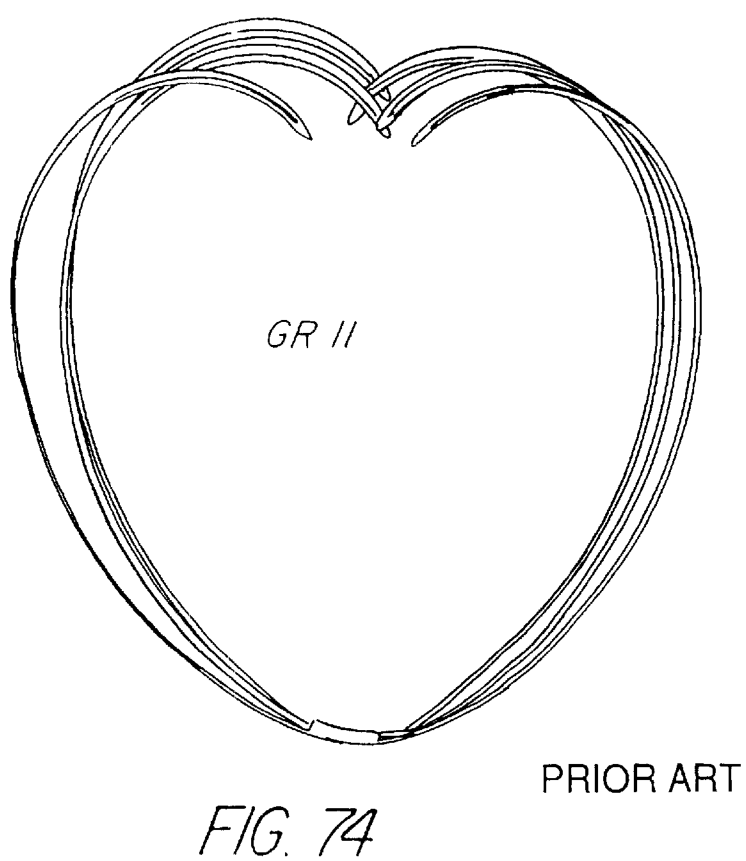
FIG. 74

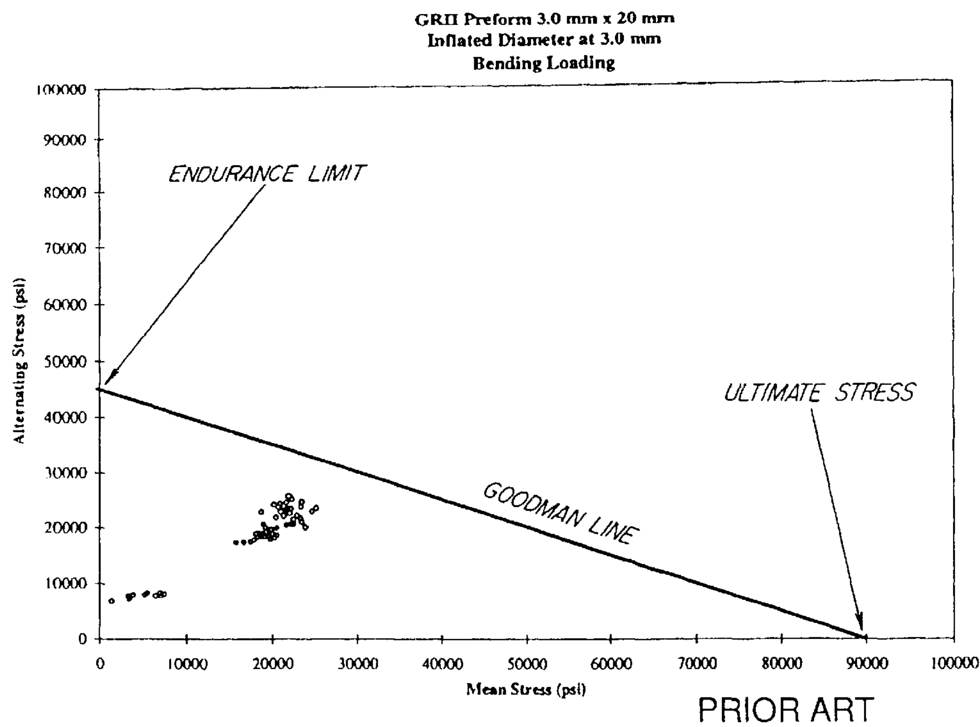
PRIOR ART
FIG. 75
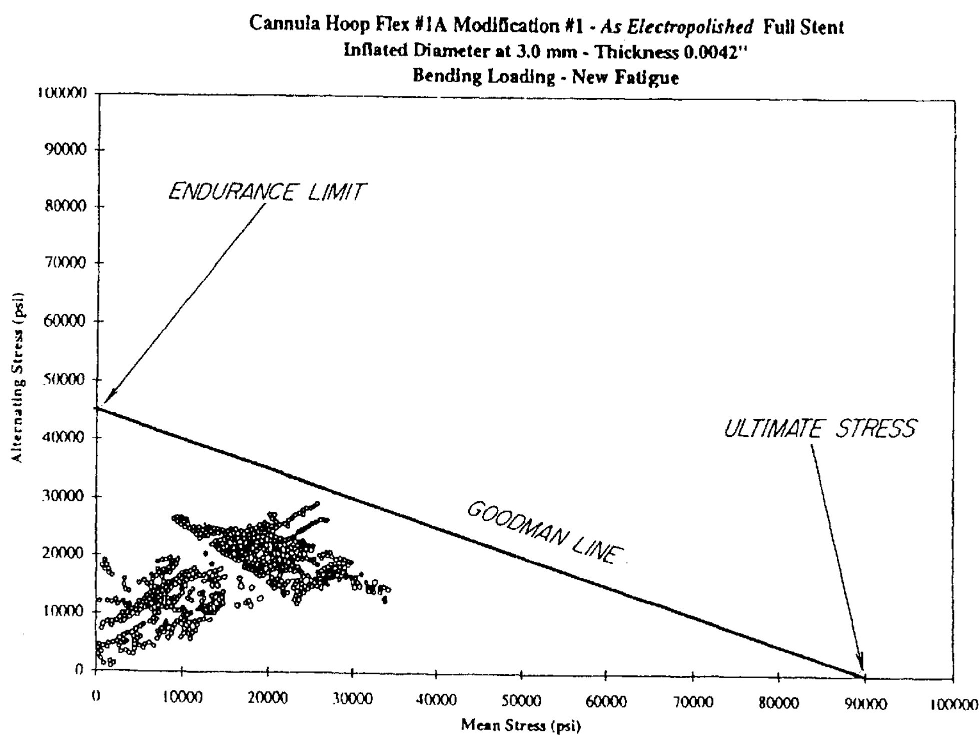
FIG. 76

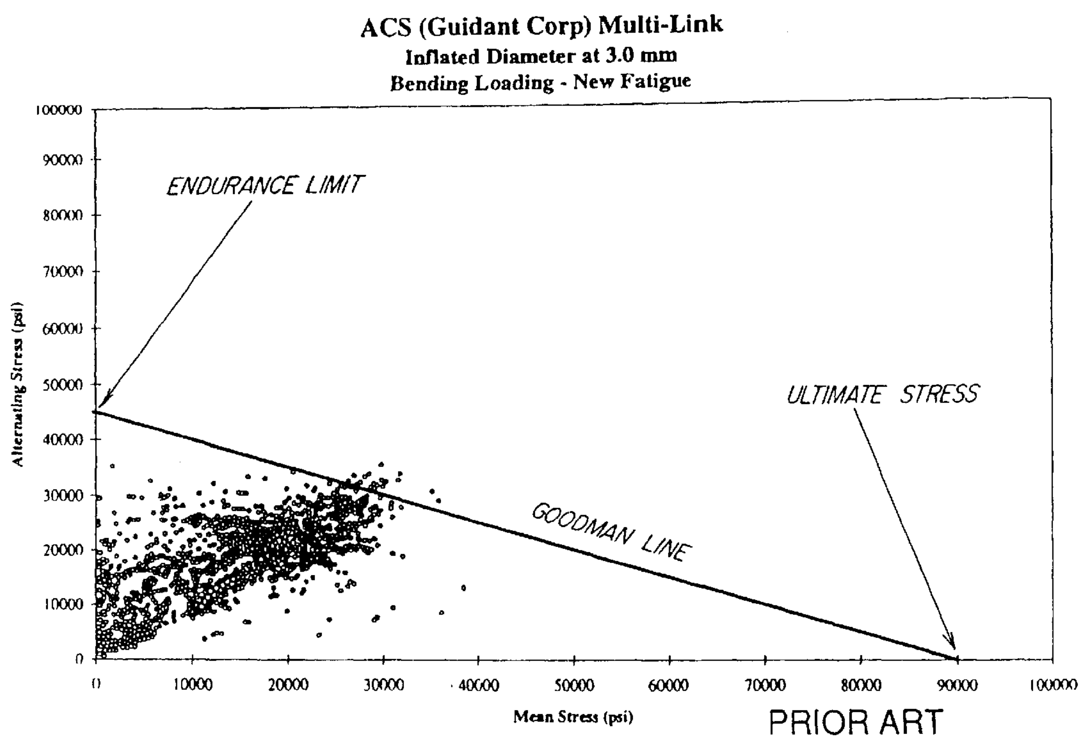
PRIOR ART
FIG. 77
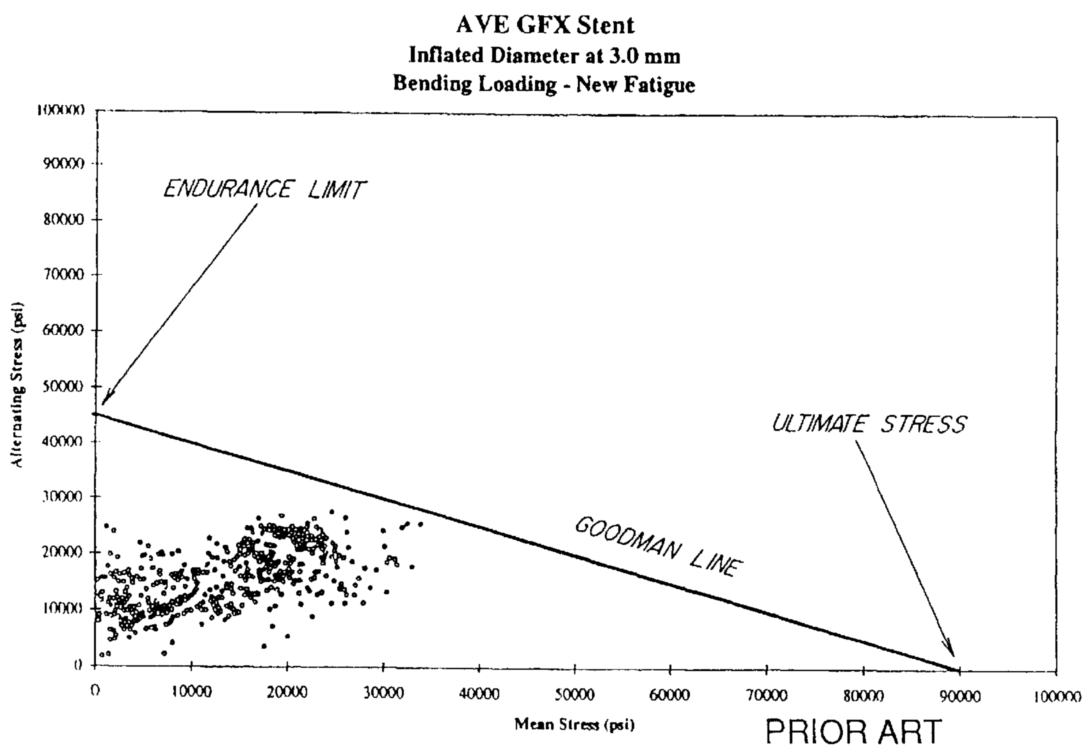
PRIOR ART
FIG. 78

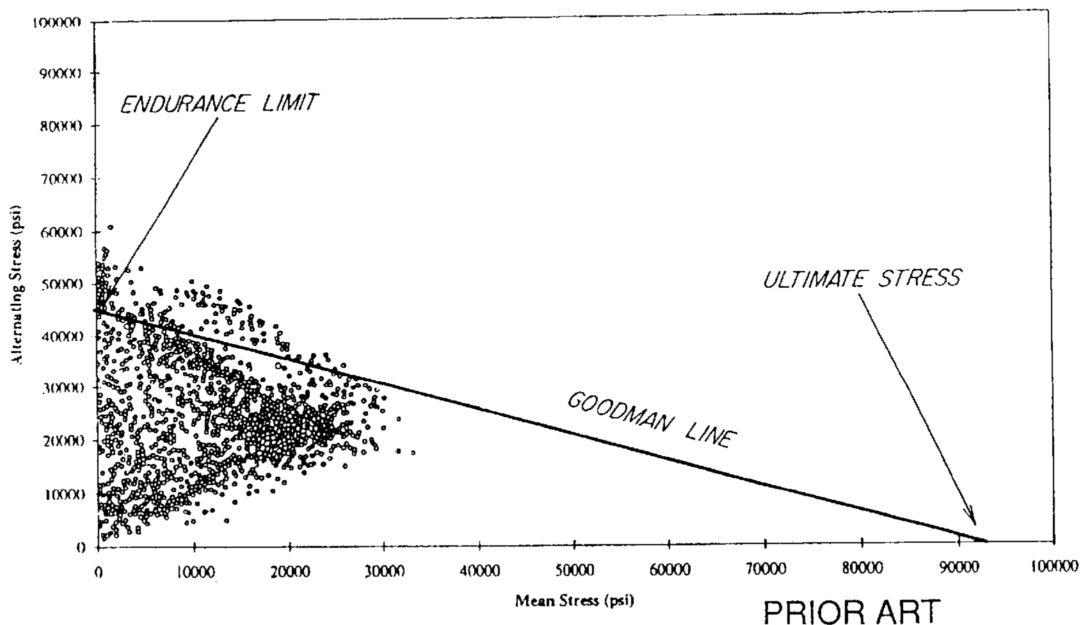
PRIOR ART
FIG. 79
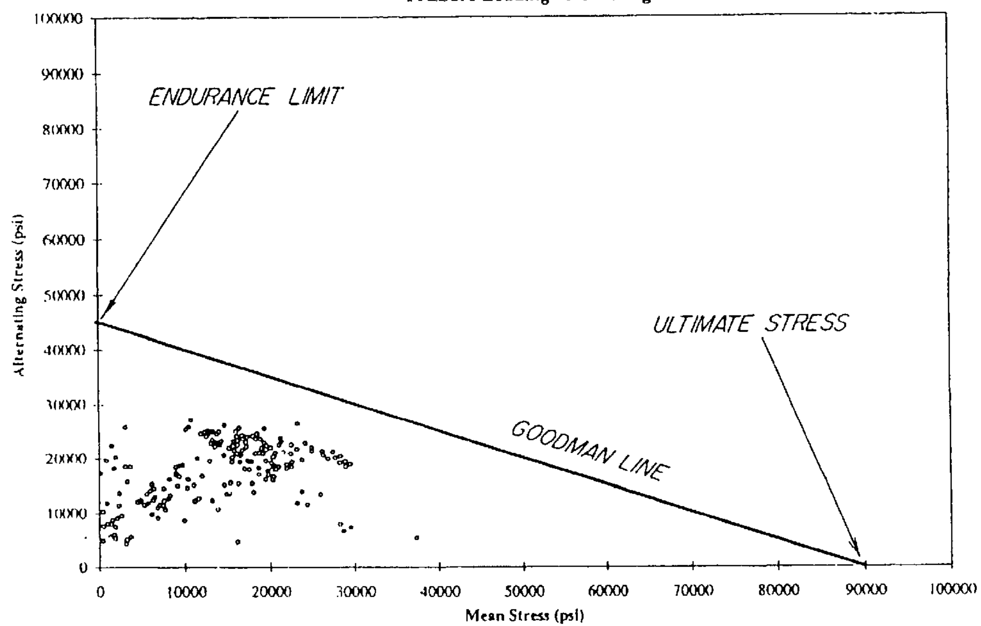
FIG. 80

RADIALLY EXPANDABLE STENT

CROSS-REFERENCE TO RELATED APPLICATIONS

This is a Divisional of U.S. patent application Ser. No. 09/160,122 filed Sep. 24, 1998, now U.S. Pat. No. 6,231, 598, which, in turn, claims priority of provisional applications Ser. No. 60/059,898, filed Sep. 24,1997, and Ser. No. 60/082,164, filed Apr. 17, 1998.

TECHNICAL FIELD

This invention relates generally to medical devices and, in particular, to a radially expandable stent.

BACKGROUND OF THE INVENTION

Vascular stents are deployed at a narrowed site in a blood vessel of a patient for widening the vessel lumen and circumferentially supporting the vessel wall. Vascular stents desirably have a small cross-sectional diameter and/or profile for introducing the stent into the affected vessel lumen.

One type of a vascular stent is made with a piece of wire that is bent into a number of turns. Although suitable for its intended use, a problem with these bent wire stents is that stress points are formed at each wire bend or turn. As a result, the wire stent is structurally compromised at a For example, a wire stent is typically positioned in a blood vessel over an inflatable balloon. The balloon expands first at opposite ends, where the balloon is not in contact with the wire stent. As a result, the wire stent is longitudinally shortened between the inflated balloon ends. With continued inflation, the middle of the balloon expands, thereby unevenly expanding the wire bends of the longitudinally shortened wire stent.

Another type of a vascular stent is made with a wire mesh that is rolled into a generally tubular shape. A problem with this stent is that the overlapping wires forming the mesh increase the stent profile, thereby reducing the effective lumen of the blood vessel. The growth of endothelial tissue layers over the wire mesh further reduces the effective blood vessel lumen. Another problem with this approach is that ion migration also occurs at the wire-to-wire contact points.

Yet another type of a vascular stent is made with a flat metal sheet with a number of openings formed in rows therein. The flat metal sheet stent also includes rows of fingers or projections positioned on one edge of the stent along the axis thereof. When expanded, a row of the fingers or projections is positioned through a row of openings on the opposite edge of the stent for locking the expanded configuration of the stent. A problem with the use of the flat metal sheet stent is that the overlapping edges of the stent increase the stent profile. Again, the stent profile and endothelial growth reduce the effective blood vessel lumen. Another problem with the use of the flat metal sheet stent is that the fingers or projections along one edge of the stent make metal to metal contact with the opposite edge of the stent. As a result, the metal edges of the stent rub during movement caused by blood flow, pulsation, and muscle movement. Yet another problem with the use of the flat metal sheet stent is that the fingers or projections extend radially outward and into the vessel wall. As a result, the intimal layer of the vessel wall can be scraped, punctured, or otherwise injured. Injury and trauma to the intimal layer of the vessel wall result in hyperplasia and cell proliferation, which in turn effect stenosis or further narrowing of the vessel at the stent site.

Still yet another type of a vascular stent is made with a piece of metal cannula with a number of openings formed in the circumference thereof. A problem with the use of a metal cannula stent is that the stent is rigid and inflexible. As a result, the stent is difficult, if not impossible, to introduce through the tortuous vessels of the vascular system for deployment at a narrowed site. Furthermore, the stent is too rigid to conform with the curvature of a blood vessel when deployed at an occlusion site. Another problem with the use of a metal cannula stent is that the stent longitudinally shrinks during radial expansion. As a result, the position of the metal cannula stent shifts, and the stent supports a shorter portion of the blood vessel wall than required.

Previous attempts to overcome flexibility problems associated with cannula stent designs have included the addition of a flexible or articulation region between the relatively rigid segments. In comparison, these flexible regions or articulations provide little radial strength. There have been clinical concerns regarding the tendency of some cannula stent designs to plastically deform at the articulations during lateral bending rather than elastically returning to the original shape. Another concern is non-uniform radial expansion of the stent during balloon inflation. A commonly observed problem with such designs is that the flexible segments do not deform outwardly in the same manner and to the same degree as the segments of higher radial strength. As a result, the stent material of the interconnection regions extends or "hangs" into the lumen of the stent (as defined by the more rigid sections). Particularly in a vascular stent, local blood flow turbulence can occur at these points that can contribute to thrombus formation.

Still another phenomenon that is especially a problem in expandable cannula type stents is the tendency of thin bars or struts to twist during expansion. Even minor manufacturing defects can create weakened bending points that contribute to this problem. A design that increases longitudinal and radial strength and stability, has fewer articulations, and evenly distributes bending stresses is less prone to twisting and non-uniform expansion. Distribution of bending stresses is also an important factor in determining a stent's susceptibility to fatigue. Articulations designed to provide flexibility between tubular non-flexible sections are typically subject to stresses during deformation that can lead to breakage. The likelihood of breakage can increase when the articulation points are welded rather than being part of the cannula wall.

For coronary applications, the ideal stent would be thin-walled, of unitary construction to eliminate welds, and have high radial strength with good endoluminal coverage to prevent restenosis. In addition, the stent would have a low profile on the balloon to reach small vessels, yet would have a good expansion ratio with low recoil following delivery to prevent migration or becoming undersized for the diameter of the lesion. An ideal coronary stent would be able to follow tortuous vessels during introduction while maintaining its shape without plastically deforming. Another desirable property is the ability of the stent to remain crimped upon the balloon so that slippage does not occur and, as a result, eliminates the need for endcaps or another means to hold the stent on the balloon. Although high radial strength is needed, the ideal coronary stent must be able to be elastically flexible over millions of bending cycles to accommodate changes in the vessel due to systole and diastole. The ideal stent should deploy uniformly at the target site without twisting, migrating, or taking on an accordion or scalloped appearance, should retain its original axial length during deployment, and should be visible under radiographic imaging as an aid in placement. While most available stents can adequately meet a limited number of these objectives, design compromises have restricted the utility and efficacy of these stents for certain clinical applications.

SUMMARY OF THE INVENTION

The foregoing problems are solved and a technical advance is achieved in an illustrative radially expandable stent that exhibits advantageously high, expanded radial stiffness for vessel wall support and an advantageously low, lateral bending stiffness for good trackability and introduction through tortuous vessels. The stent includes an elongated member with a passage extending longitudinally therein that is radially expandable with, for example, a balloon catheter. Alternatively, the elongated member can be self-expanding and can be comprised of, for example, a nickel-titanium alloy material, which advantageously has a supraelastic property. The elongated member includes a first longitudinal segment including a plurality of cells. Selected of the cells each includes a first and a second longitudinal strut for maintaining the longitudinal integrity of the stent before, during, and after expansion of the stent. In this configuration, the first longitudinal segment has an expanded radial stiffness greater than $1.6\times10^{-2}$ lbs (force) per millimeter (length). In another aspect, when the selected cells include a closed cell structure, the expanded radial stiffness need be just greater than $4.87\times10^{-3}$ lbs (force) per millimeter (length). In still another aspect, the expanded radial stiffness is greater then $3.47\times10^{-2}$ lbs (force) per millimeter (length).

The elongated member also has an interconnection segment connected to the first longitudinal segment and has a expanded radial stiffness less than that of the first longitudinal segment. The interconnection segment provides advantageously lateral flexibility to the stent. When the selected cells include longitudinal struts, the longitudinal segment and interconnection segment have a combined lateral bending stiffness less than $6.0\times10^{-6}$ in-lb (force) per degree per millimeter (length). When the selected cells are of a closed scissor-jack configuration, the combined lateral bending stiffness need only be less than $5.3\times10^{-5}$ in-lb (force) per degree per millimeter (length). In still another aspect, the elastic bending stiffness is less than $3.3\times10^{-6}$ in-lb (force) per degree per millimeter (length).

In one advantageous configuration, the interconnection segment includes a plurality of interconnected curvilinear struts that form an approximately serpentine pattern. In another advantageous configuration, the interconnection segment includes a plurality of interconnected linear struts that form a zig-zag or sawtooth pattern.

One or more connecting struts or members are utilized to interconnect the longitudinal and interconnection segments. The lateral flexibility of the interconnection segment minimizes, if not eliminates, the stress at the connecting strut or member and provides the stent with a high degree of expanded radial stiffness and significant lateral flexibility which can be used for long periods of time in a pulsatile environment without causing fatigue and fracture of the stent. The length of the stent can be selected as desired by including a plurality of the longitudinal segments of which adjacent ones are interconnected by an interconnection segment.

To enhance the radiographic visibility of the stent, at least one end of the stent includes a radiopaque marker of, for example, gold. To further enhance the radiopaque visibility of the stent, a plurality of radiopaque markers are positioned at an end of the stent to indicate the orientation of the stent. This plurality advantageously provides the physician with the spacial orientation of the stent when being introduced through the vascular system.

In another aspect of the radially expandable stent, the longitudinal and interconnection segments are interconnected and structured such that the longitudinal segment has a higher expanded radial stiffness. In this case, the combined lateral bending stiffness is less than $3.33\times10^{-6}$ in-lb (force) per degree per millimeter (length). The expanded radial stiffness of the longitudinal segment can then be greater than $3.47\times10^{-2}$ lbs (force) per millimeter (length).

In another embodiment of the radially expandable stent, the first longitudinal segment includes a plurality of interconnected cells. Selected of these cells each includes a first and a second longitudinal strut that are interconnected by at least one pair of circumferentially adjustable members. The circumferentially adjustable members advantageously permit the circumferential expansion of the longitudinal segment with minimal change in the axial length of the longitudinal struts when the longitudinal segment is radially expanded. As a result, the longitudinal struts remain substantially parallel with the longitudinal axis of the stent. In one aspect, adjacent cells of the selected cells share a common first and second longitudinal strut with respectively laterally adjacent cells. In another aspect, the circumferentially adjustable members are “U”- or “V”-shaped to provide a scissor-jack configuration, which provides the stent with its high expanded radial stiffness.

The foregoing problems are also solved and a technical advance is achieved in an illustrative radially expandable stent having a longitudinal segment including, for example, a plurality of laterally interconnected closed cells that are formed from, or into, a tubular structure or cannula that has an advantageously high expanded radial stiffness and that changes length minimally, if at all, when expanded radially. The stent also has an interconnection segment that is connected to the longitudinal segment and provides the stent with advantageous lateral flexibility and a low elastic bending stiffness. Each cell has first and second parallel longitudinal bars or struts that are interconnected at each end by a circumferentially adjustable member. In an illustrative example, the opposing circumferentially adjustable members are inclined toward the center of the cell’s aperture. A series of the basic cells are laterally interconnected to form a tubular structure. When the tubular structure is radially expanded, such as by an inflatable balloon, the longitudinal struts remain substantially longitudinal to each other and circumferentially aligned while the circumferentially adjustable members open or unfold as their attachment points move apart, resulting in an increase in cell width. The action of the circumferentially adjustable members, much like that of a scissor jack, accounts for the increase in stent diameter. Because the longitudinal struts retain their alignment, the longitudinal segment maintains a stable axial length during expansion. The stent can also be self-expanding. One such self-expanding stent can comprise a nickel-titanium alloy material having, for example, a supraelastic property.

Radiopaque markers can be advantageously positioned at one or both ends of the pattern to aid the physician in positioning the stent under fluoroscopic imaging. In the illustrative embodiment of the invention, gold markers are placed in the apertures at the ends of each longitudinal strut; however, not all apertures need be filled.

In the preferred illustrative embodiment of the invention, the circumferentially adjacent closed cells are interconnected such that they share the longitudinal struts of adjacent segments. In an alternative embodiment each closed cell contains longitudinal struts that are not shared with adjacent segments, but rather are connected to the adjacent longitudinal strut by at least one short strut.

Within the illustrative example of the invention are included interconnection segments positioned between adjacent longitudinal segments. The interconnection segments advantageously permit lateral flexibility in what otherwise would be a substantially rigid stent and is advantageous for use in a site subject to great flexural forces such as the coronary arteries. In the illustrative example, the interconnection segment is comprised of a continuous series of serpentine bends that connect to the adjacent longitudinal segment via at least one short interconnection strut. In addition to permitting the stent to flex and thus be placed in a more tortuous-shaped lumen, a primary requirement of the bends of interconnection segment is that they do not interfere with the expansion of the longitudinal segments. The number, shape, thickness, and point of attachment of these serpentine bends can be varied depending on the qualities desired in the stent. The stent in the illustrative example for peripheral use has three points of attachment at between a longitudinal segment and adjacent interconnection segment such that every third serpentine bend is attached to a longitudinal segment, one third of the bends are attached to the opposite longitudinal segment, and the remaining third are unattached on both sides. In another illustrated embodiment for coronary use, there is a single point of attachment between a longitudinal segment and an interconnection segment that is 180° opposed to the single attachment point on the same interconnection segment. This pair of attachment points are rotated in subsequent interconnection segments to increase stent flexibility.

In another embodiment of the stent, the interconnection segment is broadly attached to the longitudinal segment rather than by a series of struts, giving the appearance that the adjacent segments have been joined by a series of "S"- or "Z"-shaped struts. The configuration or pattern of curvilinear struts that comprise the interconnection region in the illustrative example is repeated throughout such that the longitudinal struts of each internal closed cell is narrowly or broadly connected to a bend of the interconnection segment at one end with the other end of the longitudinal strut free of attachment.

The interconnection segment configuration found in the illustrative example can be mirrored in the adjacent interconnection region such that every other internal longitudinal strut is connected at both ends, while the alternating longitudinal struts are unattached on both ends.

The serpentine bends of the interconnection segment can be varied to permit different expansion and flexural properties. For example, the bending regions or fillets can be "keyhole" shaped like the bends of the circumferentially adjustable struts wherein the struts flair outward around the apex of the bend. This modification reduces bending stress and allows for slightly more expansion capability. The struts between the bends can be parallel to each other and in alignment with the longitudinal axis of the stent, or they can be inclined with respect to the stent's longitudinal axis, either alternately as in the illustrated preferred embodiment, or identically inclined. Alternating inclination of these struts can partially or completely offset any shortening that takes place as the stent is expanded to the nominal diameter. While there is no net change in the length of the longitudinal segments, the unfolding of the curvilinear struts of the configuration of the illustrative example, causes the interconnection segment to shorten, thereby affecting the overall length of the stent. This change in length can be partially offset when the opposing curvilinear struts are angled toward each other in a manner such that as the stent is expanded initially, the opening of the bend forces the stent to lengthen slightly. As the stent continues to expand, the angle of the bends are opened further, which serves to draw the longitudinal segments back together and shorten the stent. The "delay" that angling the curvilinear struts affords before the stent begins to longitudinally contract, reduces the total contraction that would otherwise occur if the struts were longitudinally aligned. By choosing the proper curvilinear strut design, it is possible to produce a stent with virtually no net change of length at the nominal or final diameter.

A further advantage of angling the struts of the interconnection segment is that the stent can become more flexible in the unexpanded state. This provides improved trackability while the stent is mounted on the balloon catheter and maneuvered through the vessel to the target site. Another concern is that struts aligned with the longitudinal axis of the catheter would be more likely to flip out of plane during bending of the balloon catheter and pose a risk of damage to the vessel.

The pattern of curvilinear struts of the interconnection segment can be oriented such that each broadly attaches to the longitudinal segment in the same manner, i.e., there is not a general serpentine waveform pattern as in the illustrative example. One advantage of this type of design is that the curvilinear struts do not deform as the stent is expanded, and, as a result, no change in the length of the stent occurs. As in the case of the pattern found in the illustrative example, the direction or orientation of the struts can be reversed in an adjacent interconnection segment.

A balloon catheter is used to radially expand the stent to engage the vessel wall surface and to maintain the vessel lumen in an open condition. The expanded stent advantageously has a minimal thickness for endothelial tissue to form thereover. As a result, the vessel lumen is advantageously maintained with the largest diameter possible.

BRIEF DESCRIPTION OF THE DRAWING

FIG. 1 depicts a pictorial view of a preferred illustrative embodiment of the radially expandable stent of the present invention;

FIG. 2 depicts an enlarged side view of a closed cell of the stent of FIG. 1 in an unexpanded state;

FIG. 3 depicts an enlarged, side view of the closed cell of FIG. 2 in an expanded state;

FIG. 4 depicts an enlarged, side view of an alternate embodiment of the closed cell of FIG. 2;

FIG. 5 depicts a top view of the stent of FIG. 1 as cut longitudinally and unrolled into a single plane;

FIG. 6 depicts an enlarged, side view of an alternate embodiment of the stent of FIG. 1 in which the curvilinear struts are parallel to each other;

FIG. 7 depicts an enlarged, side view of an alternate embodiment of the stent of FIG. 1 in which the fillets of the serpentine bends are enlarged;

FIG. 8 depicts an unrolled view of another preferred embodiment of the present invention having a single attachment point between longitudinal and interconnection segments;

FIG. 9 depicts an enlarged, partially sectioned view of another embodiment of the interconnection segment of the stent of FIG. 1;

FIGS. 10–11 depict partially sectioned and unrolled views of alternative embodiments of the stent of FIG. 1;

FIG. 12 depicts a cross-sectional end view of both an unexpanded and an expanded longitudinal segment of the stent of FIG. 1, taken along the line 12—12;

FIG. 13 depicts an enlarged partial cross-sectional end view of the stent of FIG. 1 taken along the line 13—13;

FIG. 14 depicts the unexpanded stent of FIG. 9 loaded on an angioplasty balloon;

FIGS. 15–16 depict enlarged, side views of an alternative embodiment of the stent of FIG. 1, whereby the circumferentially adjustable members project outward from the cell;

FIG. 17 depicts an enlarged, side view of an alternative embodiment of the stent of FIG. 1 with each cell having both inwardly and outwardly projecting circumferentially adjustable members;

FIG. 18 depicts an enlarged, side view of an alternative embodiment of the stent of FIG. 1, whereby segments with outwardly-projecting circumferentially adjustable members are alternated with those having inwardly-projecting members;

FIG. 19 depicts an enlarged, side view of an alternative stent embodiment of the present invention in which the closed cells are chevron shaped;

FIG. 20 depicts an enlarged, side view of an alternative stent embodiment of the present invention in which closed cells having inwardly-projecting circumferentially adjustable members alternate with closed cells having outwardly-projecting members;

FIG. 21 depicts an enlarged, side view of an alternative stent embodiment of the present invention in which a longitudinal segment is elongated and has multiple pairs of circumferentially adjustable members;

FIG. 22 depicts an enlarged, side view of an alternate stent embodiment of the present invention, whereby the interconnected closed cells within a longitudinal segment are longitudinally offset from each other;

FIG. 23 depicts an unrolled side view of another preferred embodiment of the present invention with a single attachment point between longitudinal and interconnection segments;

FIG. 24 depicts an enlarged side view of the stent of FIG. 23;

FIG. 25 depicts a partial, enlarged side view of a self-expanding embodiment of the present invention in the constrained state;

FIG. 26 depicts a cross-sectional end view of both an unconstrained and constrained longitudinal segment of the stent of FIG. 25, taken along the line 26—26;

FIG. 27 depicts an enlarged partial cross-sectional end view of the stent of FIG. 26 taken along the line 26—26;

FIG. 28 depicts a pictorial view of the present invention with a preferred distribution of radiopaque markers;

FIG. 29 depicts a cross-sectional end view of an eight-cell stent embodiment having four radiopaque markers;

FIG. 30 depicts an enlarged side view of a preferred stent embodiment having multiple radiopaque markers;

FIGS. 31–34 depict enlarged cross-sectional views of various embodiments of stent eyelets adapted for securing a radiopaque marker;

FIG. 35 depicts an enlarged cross-sectional view of a radiopaque marker within the eyelet of FIG. 31;

FIG. 36 depicts an alternative stent embodiment with radiopaque markers to indicate the position of an opening in the pattern;

FIG. 37 depicts an alternative embodiment of a radiopaque marker;

FIGS. 38–41 depict side views of the unexpanded stent embodiment of FIG. 1;

FIG. 42 depicts a perspective view of the expanded stent of FIGS. 1 and 38;

FIG. 43 depicts a side view of the expanded stent of FIGS. 1 and 38;

FIGS. 44–53 depict side views of unexpanded and expanded Prior Art stents;

FIG. 54 depicts a side view of the unexpanded stent of FIGS. 1 and 38 showing the bending range used to determine trackability;

FIGS. 55–59 depict side views of the present stent (FIG. 55) and Prior Art stents showing curvability;

FIGS. 60–64 depict side views of the present stent subjected to a tent-on-tube bending and re-straightening test;

FIGS. 65–67 depict an enlarged side view of the free end of Prior Art stents (FIGS. 65 and 66) and the present stent (FIG. 67) after bending and re-straightening;

FIG. 68 depicts an enlarged side view of the present stent during the loop lift away analysis;

FIGS. 69–74 depict end views showing the expanded lumen shapes of the present stent (FIG. 69) and Prior Art stents (FIGS. 70 to 74);

FIGS. 75–79 depict Goodman diagrams for rotating tube fatigue of the present stent (FIG. 76) and Prior Art stents (FIGS. 75 and 77 to 79); and FIG. 80 depicts a Goodman diagram for pulsatile fatigue loading of the present stent.

DETAILED DESCRIPTION

FIG. 1 depicts a pictorial view of a preferred illustrative embodiment of an unmounted, radially expandable, laterally flexible stent 10 in an unexpanded state. The stent, which is comprised of an elongated member 11 with a passage 12 extending longitudinally therethrough, is formed from a tube of malleable, biocompatible material such as stainless steel. Preferably, the stent is fabricated from a commercially available, series 316L stainless steel cannula with a wall thickness of in the range of 0.002–0.007 in. and, most preferably, 0.005 in. for coronary use with peripheral stents possibly being slightly thicker. If finishing techniques such as electropolishing are used that remove surface material, the final wall thickness of the preferred coronary stent will be slightly less, usually in the range of 0.004–0.0042 in. By annealing the 316L stainless steel, the metal is soft and plastically deformable to allow the stent to be readily radially expanded using a commercially available balloon catheter. Properties of the preferred stent material include a tensile strength of 80–90 ksi with an elongation of 40–50%. With sufficiently malleable materials, the illustrative stent pattern has no resistive moment of inertia or stiffness to overcome such that would cause the stent to suddenly "pop open" as it is initially expanded. This is advantageous in that the thickness of the various struts within the stent is not dictated by the need to reduce the moment of inertia for optimal deployment. Besides stainless steel, other materials can be used for the stent including titanium, tantalum, or nitinol, which is a commercially available nickel-titanium alloy material that has shape memory and is superelastic.

The preferred stent embodiment includes a repeating series of first and second alternating segment types. The first segment type is a longitudinal segment 14 having a plurality of laterally interconnected closed cells 13. The second segment type is a flexible interconnection segment 21 that interconnects adjacent longitudinal segments via at least one short interconnection strut, member, or tab 36. The longitudinal segments, when expanded, provide the stent with the radial strength required to maintain patency of a lumen or vessel such as an vein, artery, or duct. The interconnection segments provide the stent with lateral flexibility necessary for placement through or into tortuous vessels or sites such as the coronary arteries that are subject to many bending cycles over a large range of angles. To form the alternating longitudinal segments from a metal tube or sheet, material must be removed in some manner, such as by a commercially available computer-controlled laser, leaving a framework of integrated support members that has a small surface area relative to the initial surface area of the tube or sheet. Other methods of manufacture include chemical etching using photoresistive masking techniques, machining, electrode discharge machining (EDM), or cutting with a water jet.

The preferred illustrated embodiment includes at least one radiopaque marker 48 at each of the distal and proximal ends of longitudinal struts 15 of the distal and proximal longitudinal segments.

FIG. 2 depicts a closed cell 13 of the stent of FIG. 1 in an unexpanded state. Each closed cell includes a pair of longitudinal struts 15, 16 which maintain longitudinal orientation during and after expansion of the stent. The longitudinal struts are typically shared with the two laterally adjacent cells 29, 29', which are interconnected with additional closed cells to form a longitudinal segment 14. Also, it is contemplated that open cells or a combination of open and closed cells can be used. In an embodiment for coronary use, the longitudinal struts have a final width after polishing of 0.008 in. to 0.01 in. It should be noted that polishing the stent after it is cut from the cannula removes approximately 0.001 in. of width from the struts, members or bars that make up the stent. The first and second longitudinal struts 15, 16 are interconnected at both ends 17, 18 by respective circumferentially adjustable members 19, 20, which deform or unfold as the stent 10 is subjected to circumferential and radial expansion forces. These adjustable members can be "V"- or "U"-shaped and can also include a relief portion that is, for example, key-hole shaped. One preferred final width of these adjustable members is 0.004 to 0.005 in. In a preferred embodiment, folded arms 51, 52 of the circumferentially adjustable members are parallel prior to expansion. As shown in the illustrated embodiment, the bending region 59 of the circumferentially adjustable members can be flared outward about the pivot point 60, resulting in a keyhole-shaped bend. This design reduces bending stresses and allows for a slightly greater expanded diameter than in a simple "U"- or "V"-shaped bend as shown in FIG. 4. To spatially accommodate the expanded bending regions, the central portion 61 of the longitudinal strut is narrowed to a width of approximately 0.005 in. after polishing.

FIG. 3 depicts an enlarged, side view of closed cell 13 of the stent of FIG. 1 in an expanded state. At full expansion of the stent, the angle 53 between folded arms 51 and 52 of the circumferentially adjustable members 19, 20 approaches 180°. Although radial strength is increased as the angle between the arms of the circumferentially adjustable members increases, additional stresses placed at the points of their attachment to the longitudinal struts 15, 16 make the preferable final angle closer to 90°. The closed cells allow a single nominally-sized stent to be deployed at different diameters within a given range. The expanded diameters preferred for use in the coronary arteries range from 2.5 to 5.5 mm, while diameters used in peripheral and non-coronary applications such the aorta, iliac, femoral, popliteal, renal, subclavian, and carotid arteries or vein graft and other venous lesions, generally range from 4.0 to 14.0 mm. The preferred length of the stent for coronary use would be 15 to 20 mm; however, 7 to 60 mm length stents would have clinical use, with even longer stents possible.

FIG. 4 depicts an enlarged, side view of an alternative preferred embodiment regarding closed cell 65 of FIG. 2, whereby the longitudinal struts 66, 67 of adjacent cells 29, 29' are not fused or shared, but rather are separate and interconnected by at least one short strut 62, 62'. In this embodiment, the interconnected longitudinal struts 16 and 67, 15 and 66 do not remain parallel during expansion unless of sufficient thickness to resist deformation. Rather, the ends 17,18 of the respective longitudinal struts, being pulled by forces due to expanding circumferentially adjustable members 19,20, bow outward from the interconnection strut 62 such that the longitudinal struts takes on a shallow "V" shape. The interconnection 62,62' between two longitudinal struts 16 and 67, 15 and 66 gives this alternate longitudinal segment some lateral flexibility, unlike that of the preferred embodiment. Another difference from the preferred embodiment is that longitudinal segment 14 depicted in FIG. 4 shortens somewhat during expansion.

While a longitudinal segment 14 can itself serve as a stent, the addition of an interconnection segment 21, as depicted in FIG. 1, permits combining multiple longitudinal segments to produce a longer stent. The primary function of these interconnection segments, however, is adding lateral flexibility.

FIG. 5 depicts a top view of the stent of FIG. 1 as cut longitudinally and unrolled into a single plane, showing how the interconnection segments 21 join adjacent longitudinal segments 14. In the preferred embodiment, the interconnection segment is formed as a series of undulating bends 75 comprised of interconnected curvilinear struts 22, 23. The linear or center portions 41 of the curvilinear struts 22,23 can either be aligned with the stent's longitudinal axis 42, as depicted in FIG. 6, or angled with respect to the longitudinal axis 42 as depicted in the FIG. 5. In the embodiment of FIG. 5, half of the curvilinear struts are angled from the stent's longitudinal axis while the alternating curvilinear struts are oppositely angled with respect to the longitudinal axis, both by equal angles. It would also be possible to have the curvilinear struts all angled in the same orientation with respect to the longitudinal axis of the stent so that they are of a parallel configuration.

Angling of the curvilinear struts can provide a benefit when the delivery catheter bearing the stent is being maneuvered to the target site. The ability of the mounted stent to flex laterally or move with the catheter is called trackability. Curvilinear struts longitudinally aligned with a relatively stiff catheter are more likely to pop out and plastically deform when the catheter is bent. Angled curvilinear struts can torque with the bending of the catheter, thus retaining their shape. The design of the longitudinal segments also contributes to the superior trackability of the present invention.

The shape, width, and thickness of the curvilinear struts can be variable, depending on the application of the stent. In a preferred embodiment, the curvilinear struts are 0.003 in. wide after polishing with a serpentine configuration resembling a letter "S" or "Z". The bends permit circumferential and radial expansion and do not limit the ability of the longitudinal segments to expand to the desired diameter. Additional bends can be added to reduce metal fatigue and permit even greater expansion if spacial limitations within a design permit an additional strut.

In the preferred embodiment depicted in FIG. 2, the curvilinear struts 22, 23 are angled with respect to longitudinal axis 42 of stent 10. By changing the angle of these curvilinear struts, the dynamics affecting the change in the length of the stent during radial expansion thereof are altered. In the illustrative example, the stent will initially lengthen as the bend 37 formed by the curvilinear struts 22, 23 opens during radial stent expansion. Lengthening continues until the curvilinear struts 22, 23 are substantially aligned with the longitudinal axis 42 of the stent. At this point, the stent is slightly longer than in the unexpanded state (FIG. 2). Continued expansion, as shown in FIG. 3, causes the bend 37 to open further, which then begins to shorten the interconnection segment 21, thereby shortening the stent. Depending on the expansion ratio and beginning angle 40 of the curvilinear struts, the change in length of the stent upon expansion can be partially offset or eliminated. In the preferred embodiment, the stent shortens after normal expansion by about 5–6%.

Another embodiment of the interconnection segment 21 is depicted in FIG. 7, whereby the fillets 45 of bends 37 are expanded ("keyhole shaped") similar to the circumferentially adjustable members of the preferred embodiment. As previously discussed, the expanded fillets reduce stresses in the region about the bend and the curvilinear struts have greater expansion potential over those having straight bends as in the preferred illustrated embodiment. Larger fillets also result in additional metal which increases coverage to the vessel in the stent's expanded state.

The interconnection segment of the present invention is designed to distribute bending forces over multiple bends to increase flexibility and fatigue life of the stent. A typical balloon expandable metallic stent is designed to plastically deform at points of stress. In stents known in the art, lateral flexibility is made possible because of a flexible portion having articulation points that deform with lateral bending stresses. With distribution of the lateral bending forces over the curvilinear struts of the present invention, the interconnection struts do not deform, and true elasticity, rather than mere flexibility, is achieved. This is of particular benefit in a vessel that undergoes repeated flexure such as a coronary artery. The interconnection struts serve as attachment points between the two segment types and are less subject to high stress load of a strut designed to flex with lateral bending forces.

The number of interconnection struts joining the longitudinal and interconnection segments can be varied according to the amount of flexibility required in the stent and the method of manufacture used. Two examples are shown in FIGS. 5 and 8. FIG. 5 depicts a first attachment pattern, whereby each alternate longitudinal strut 15 of a first longitudinal segment 14 is attached to a curvilinear strut of the interconnection segment 21 via an interconnection strut 36, member, or tab. Conversely, the longitudinal struts 32 that are longitudinally aligned with the unattached longitudinal struts 16 of the first longitudinal segment 14, are attached to the interconnection segment 21 by interconnection struts such that all of the longitudinal struts of the second longitudinal segment 25 (and any internal segment) are attached to the interconnection segment 21 at the first end 84 and free of attachments or struts on the second or opposite end 90. Obviously, the longitudinal segments 14, 69 comprising the distal 63 and proximal 63' ends of the stent are only attached to an interconnection segment 21, 39 on the inward segment ends 64, 64' thereof.

Another preferred embodiment depicted in FIG. 8 has a single interconnection strut, tab, or member 36 connecting a longitudinal segment 14 and an interconnection segment 21. A second interconnection strut 68 on the first interconnection segment 21 attaches to another adjacent longitudinal segment 25 at a second longitudinal strut 32 that is longitudinally offset by 180° (three cells) from the first longitudinal strut 36 of the first longitudinal segment 14. Offsetting the attachment points on an interconnection segment, whether one or more interconnection struts are used, is important in reducing bending stresses that contribute to metal fatigue and in maximizing elasticity of the stent. In the embodiment shown in FIG. 8, the pair of interconnection struts 36', 68' of second interconnection segment 39 are circumferentially offset 120° (two cells) with respect to the corresponding pair of interconnection struts 36, 68 of first interconnection segment 21. While maintaining alignment of the interconnection strut pairs across the length of the stent is permitted, staggering the interconnections improves overall stent flexibility and reduces bending stress. For a six-cell stent, a rotation pattern of 120° is preferred, whereby every fourth pair of interconnection struts would be aligned. The two-cell stagger is the best compromise between maximally offsetting adjacent interconnection pairs and having the longest distance possible between aligned pairs.

A single interconnection point between the longitudinal and interconnection segments represents the most flexible embodiment of the present invention. The increased flexibility, while potentially advantageous clinically, can present problems during the manufacturing process. As the material is cut away by the laser, there can be a tendency of the stent to sag or bend under its own weight because of the lack of support between the longitudinal and interconnection segments. One way to solve this problem is to shorten the length of the interconnection segment relative to that of the longitudinal segment. The interconnection segment 21 can also include linear struts that form a zig-zag or sawtooth configuration.

FIGS. 23–24 depict another preferred embodiment of the present invention, similar to that of FIG. 8, to solve the sagging problem. Here, the interconnection segment 21 is reduced in length to facilitate manufacture of a single point connection stent. To determine the optimal length of the interconnection segment 21 relative to that of the longitudinal segment 14, a formula is used to calculate proper segment lengths for a given stent diameter. Optimal length is defined as a stent having maximal radial strength (angle as large as possible), leg length providing an angle resulting in sufficiently low stress and good fatigue properties, and an interconnection segment that will not allow the stent to bow during laser cutting. Segment A (FIG. 24) represents length 88, which is equal to one-half the length of the longitudinal segment 14. Segment B represents length 89 of the interconnection segment 21. The following formula can be used to calculated the segment lengths A and B for a six-cell stent. Segment A=10–11% of the expanded circumference of the stent. Segment B=7 to 8% of the circumference of expanded stent. For example, if the largest practical or "safe" expanded diameter of a stent is 3.5 mm, given a stent circumference of 11 mm or 0.433 in., the desired length of A (one half of the longitudinal segment) would be in the range of 0.043 to 0.048 in. to comprise 10–11% of the expanded circumference. Consequently, the length of B (the interconnection segment) would need to fall within a range from 0.030 to 0.035 in.

While understanding that the size and material used affects rigidity and other physical characteristics of the single interconnection stent embodiment, the preferred values of the corresponding A and B segments are 8–13% and 5–10% of expanded circumference for a stent with an expanded diameter of 3.5 mm. A more preferred range of A and B would be 9–12% and 6–9%, respectively, with the most preferred range being 10–11% for A and 7–8% for B.

Shortening the interconnection segment 21 reduces the potential benefit of angling the curvilinear struts 22, 23 relative to the longitudinal axis 42 of the stent; therefore, the curvilinear struts remain parallel in the embodiment of FIG. 23. Another difference with the embodiment of FIG. 8 is that the fillets 45 are expanded or keyhole shaped at points where an interconnection strut 36, 68 connects to the longitudinal segment, whereas the remaining bends 37 of the serpentine struts 81 do not have expanded fillets.

Another method of manufacturing a single attachment point stent would be to incorporate additional thin interconnection struts into the design of the stent that would be polished away or otherwise removed during the finishing process.

The connection pattern between longitudinal segments and interconnection segments are not limited to the two basic patterns depicted in FIGS. 5 and 8. For example, a six-cell stent, like the preferred embodiment, can have an interconnection strut attaching to every third longitudinal strut for a total of two interconnections per longitudinal segment-interconnection segment interface. An eight-cell stent might have four interconnection struts per interface resulting in an alternating connection pattern. It is also important to note that the number of bends or curvilinear struts of the interconnection segment is not equal to the number of closed cells in the corresponding longitudinal segment in the preferred embodiment. The additional bends add flexibility and vessel coverage, and are not limited to a particular number or arrangement. While there is an independent relationship between the number of cells per longitudinal segment and the bends of the interconnection segment, asymmetrical connection patterns can potentially interfere with uniform expansion of the stent that could result in struts or portions of the stent flipping out of the circumferential plane during expansion.

As discussed, the interconnection segment of the preferred stent embodiments is essentially isolated from adjacent longitudinal segments with respect to shared bending stresses due to the one or more short interconnection struts that provide only a limited physical connection. Although less rigid than the longitudinal segments, the interconnection segment does possess a degree of radial strength to support the vessel in addition to distributing the bending forces to give the stent lateral elasticity or flexibility.

FIG. 9 depicts an alternate embodiment in which selected curvilinear struts 22, 23 of the interconnection segment 21 are directly fused with a longitudinal strut 15 of the longitudinal segment 14 instead of being attached via an interconnection strut, member or tab. The first ends 26 of the adjoining curvilinear struts 22, 23 form a bend 37 whose apex 38 is broadly attached to the second end 18 of a longitudinal strut 15. The second ends 30 of curvilinear strut 22 and an oppositely adjacent curvilinear strut 49 are connected to form a free bend 37'. The other curvilinear strut 23 of the pair forming the attached bend 37, is joined to its oppositely adjacent curvilinear strut 58 at their second ends 30 to form a second free bend 37 ". The series of bends between attachment points comprise a serpentine strut 81, which in the embodiment depicted, consists of a series of three curvilinear struts and two free bends. As with the preferred embodiments, the interconnections 27, 31, 33 between a particular interconnection segment 21 and the adjacent longitudinal segments 14, 25, occur at non-aligned longitudinal struts 15, 32, 34.

The embodiment shown in FIG. 9 is similar to that of FIG. 5 in that alternate longitudinal struts (e.g., 32 and 34 ) are connected for a total of three connections between segments. In this embodiment, the “S”-shaped serpentine strut that includes curvilinear strut 22 is connected to longitudinal segment 14 at attachment region 27, and is also connected to longitudinal segment 25 at attachment region 31. The adjacent “Z”-shaped serpentine strut 81 that includes curvilinear strut 23 is also connected to longitudinal segment 14 at attachment region 27. It extends from that point as a mirror opposite of the adjacent serpentine strut connected to longitudinal segment 25 at attachment region 33. It is also possible to have as few as a single attachment, similar to FIG. 8, if one classifies two curvilinear struts 22, 23 connected to the attachment region 27 of a longitudinal strut 15 as a single broad attachment—a structural corollary to an interconnection strut. The broadly fused interconnection segment functions in the same manner as the other preferred embodiments to evenly distribute the bending forces over the bends of the interconnection segment, rather than concentrating them at an articulation point.

FIGS. 10–11 depict partially sectioned and unrolled views of alternative embodiments of the stent of FIG. 1. The stent pattern 56 in FIG. 10 differs in that the second interconnection segment 39 joining the second and third longitudinal segments 25, 69 is the mirror image of the first interconnection segment 21 that joins the first and second longitudinal segments 14, 25. The result of this configuration is that longitudinal struts 15, 16 of the second longitudinal segment (and all internal longitudinal segments) alternate between being connected, to the interconnection segment at both ends 72, 73 and being completely unattached. In comparison, the longitudinal struts 15, 16, 32 of the illustrated embodiment of FIGS. 1–5 are attached at one end and unattached at the opposite end. The configuration depicted in FIG. 10 is possible for both the broadly-fused method of attachment as shown, or attachment with interconnection struts as in one of the preferred embodiments depicted in FIGS. 5, 8, and 23.

In each of the interconnection segment embodiments heretofore depicted, the curvilinear struts are interconnected in a waveform pattern 75, i.e., the serpentine struts 81 appear as a series of interconnected “S's” and “Z's”. The embodiment of FIG. 11, shows an alternative configuration 57 in which the interconnection segment consists of series of discrete, identically oriented curvilinear struts 81 that form an all “Z”-shaped pattern. The serpentine struts of this alternative design distribute the bending forces over the entire interconnection segment 21; however, they do not plastically deform and unfold as the stent expands as with the other embodiments. Staggering the longitudinal segments 14, 25, 69 such that the longitudinal struts 15, 32, 71 of consecutive segments are not aligned, results in a configuration whereby the attached ends of the serpentine struts do not span an expandable closed cell 13. Therefore, the curvilinear struts merely move apart with respect to each other, leaving open areas between the struts. Because the serpentine struts do not change shape as the stent is expanded, stents made from the patterns depicted in FIG. 11 will not change length as they expand. If the longitudinal struts of the longitudinal segments are aligned, an “S”- shaped curvilinear strut must attach to non-aligned longitudinal struts which forces the curvilinear strut to deform and unfold as the stent is expanded. While different curvilinear strut designs other than an "S" or "Z" shape (e.g., an Ω shape), could attach aligned longitudinal struts, flexibility and fatigue life can be compromised. Consequently, it is preferable to offset the attachment points between consecutive longitudinal segments in the present invention.

As with the alternate embodiment shown in FIG. 10, the stent design 57 depicted in FIG. 11 can be altered such that second interconnection segment 39 is a mirror image of the first interconnection segment 21, i.e., "Z's" vs. "S's". While the second longitudinal segment 25 would be offset with respect to the first longitudinal segment 14, the third longitudinal segment 69 would be aligned with the first longitudinal segment 14, unlike the stent in FIG. 10 where the interconnection segments 21, 39 are of identical orientation and the longitudinal segments 14, 25, 69 are progressively staggered, resulting in non-alignment of the longitudinal struts over the length of the stent.

FIG. 12 is an end view of preferred stent 10 of FIG. 1 taken along line 12—12 depicting the shape of the stent before and after expansion. The preferred stent embodiment shown, having six closed cells 13 per longitudinal segment, is expanded from the initial circular configuration 43 to basically that of a rounded 12-sided shape when expanded to the nominal stent diameter 44. This represents an expansion ratio of approximately 3:1.

While a six-cell design is preferred for smaller diameter stents of one of the preferred embodiments, the stent can have fewer or additional cells. An odd number of cells is possible, although that would preclude many of the interconnection configurations that rely on regularly spaced interconnections. For example, longitudinal struts in a five-cell longitudinal segment occur at 72° intervals, making it impossible to have attachments that are 180° apart. Regularly spaced connections, which are depicted in the embodiments of FIGS. 1–10, provide a more even distribution of the bending stresses as the stent radially expands. An eight-cell design is appropriate for larger stents such as for peripheral use.

FIG. 13 depicts an enlarged, partial cross-sectional end view of one longitudinal strut 15 of FIG. 1, the attached curvilinear struts 22, 23, and first circumferentially adjustable members 19, 19' of laterally adjacent cells 13, 13', the latter being opened to approximately a 90° angle following expansion. While the circumferentially adjustable members 19, 19' deform about the apex of the bending zone 45 during expansion, creating essentially a 12-sided stent cross-sectionally, the curvilinear struts more closely conform to a true circular shape. The eight-cell embodiment has a more circular shape than the six-cell embodiment when expanded.

The preferred method of expanding stent 10 of FIG. 1 is by use of an angiographic balloon catheter 46, which is depicted in FIG. 14. A deflated balloon 47, which is bonded to the catheter 46, is positioned within the tubular-shaped stent 10 to radially expand the stent to a nominal diameter when positioned at the occlusion site. Preferably, the balloon 47 is approximately 2 mm longer than the stent 10. To aid in balloon expansion of the stent, the inner and outer surfaces 82 of the stent can be treated to lower its coefficient of friction. In one instance, the treatment comprises a coating of parylene on the surface of the sheet of material. Another coating material is polytetrafluoroethylene. Furthermore, the surface of the stent can be ion beam-bombarded to advantageously change the surface energy density and reduce the coefficient of friction.

Although any commercially available angiographic type balloon catheter can be used for expanding the stent, irradiated low density polyethylene seems to hold the stent better during introduction and is less susceptible to pinhole leak. Balloons of other materials such as polyethylene terephthalate (PET), ethylene or polyolefin copolymers, polyester, polyurethane, polyamides, polyimides, polyvinyl chloride, or nylon can also be used.

The stent is crimped onto the balloon catheter to help prevent it from slipping while it is being maneuvered to the target site. The high radial strength of the present stent helps it to retain its shape after crimping so that it doesn't recoil and lose compressive force on the balloon. Another benefit of the design is that the thick longitudinal struts resist deformation (i.e., flared edges) as the stent is laterally flexed while being introduced through the guiding catheter. Keeping the ends of the stent tight against the balloon is advantageous to help eliminate edges or projecting stent components that are likely to catch on tissue, calcifications, or other structure as the balloon catheter and stent enter the vessel. Eliminating the likelihood of flared edges means the stent is much less likely to slip from the balloon, and special means to prevent this from occurring are not required.

The robust design of the present stent also advantageously allows it to resist deformation patterns that can lead to "dog-boning" during balloon inflation. This is the phenomenon whereby the ends of the stent are expanded first as the balloon expands, and expansion subsequently progresses inward from both ends to the middle. Uniform expansion also results in a stent with struts and elements remaining in plane and not projecting into the vessel wall, where they can cause trauma, or extending into the lumen which impedes blood flow that can promote thrombus formation.

FIGS. 15–16 depict enlarged, side views (unrolled) of alternative embodiments of the stent of FIG. 1 whereby the circumferentially adjustable members 19, 20 project outward from the cell 13 rather than into the cell as previously depicted. Having outward circumferentially adjustable members permits a reduction in the height 74 of the closed cells, resulting in more cells for the same diameter stent or a lower profile stent in the unexpanded state. Some additional shortening of the stent can occur during expansion as the outwardly-projecting circumferentially expandable members located at the ends of the stent, unfold. Referring to FIG. 15, the longitudinal distance between the gold markers 48, 48' on the distal and proximal ends 63, 63' of the stent is not affected by shortening that occurs due to expansion of the outermost circumferentially adjustable members. With the circumferentially adjustable members projecting outward, there is not a clearly delineated interconnection segment as there is with the embodiments having inwardly facing members; however, the interconnection segment 21 essentially functions the same. The projections from the longitudinal segments 14, 25 into the interconnection segment force the struts and bends of the interconnection segment into a more restricted space in the unexpanded state. This limits design options for the waveform configuration of the curvilinear, serpentine struts 81. In FIG. 15, the longitudinal segment 14 is circumferentially offset with respect to adjacent longitudinal segment 25 by a distance equal to half the height 74 of one closed cell 13. Offsetting the longitudinal cells permits the interconnection segment to be narrower and provides a space that can better accommodate a regular waveform pattern 75 similar to that of the preferred embodiment. When the longitudinal struts 15, 32 are aligned as in FIG. 16, a different undulating or waveform pattern 108 such as the one illustrated can best utilize the available interconnection segment 21 space. The number of connections between the longitudinal and interconnection segments can be variable as with the preferred embodiments, but connections should consist of short to medium length interconnection struts 36, 68 rather than a broad connection such as that disclosed in FIG. 9.

FIG. 17 depicts an enlarged, side view of an alternate embodiment of the stent 10 of FIG. 1 with each closed cell 13 having both inwardly and outwardly projecting circumferentially adjustable members 76, 76', 77, 77'. In the illustrated embodiment, the closed cells 13 of the first longitudinal segment 14 have inwardly projecting circumferentially adjustable members 76, 76' with a radial expansion potential greater than that of the corresponding outward projections 77, 77'. Therefore, the inner members do not unfold to as great an angle as the outer members. While the inner members do not make the same contribution to radial hoop strength, they do add coverage and support to the vessel wall within the closed cells. The second longitudinal segment 25 is an example of where the inner 76, 76' and outer 77, 77' circumferentially adjustable members have equal potential for radial expansion. Either of these segments can have a higher hoop strength than the other disclosed embodiments in that there are two pairs of circumferentially adjustable members unfolding to provide maximal radial support to the segment. As with the embodiments of FIGS. 15 and 16, the cells can be longitudinally aligned, or offset as illustrated.

FIG. 18 depicts an enlarged, side view of an alternative embodiment of the stent of FIG. 1, whereby segments 14 with outwardly-projecting circumferentially adjustable members are alternated with those having inwardly-projecting members 25. An alternative embodiment of this basic design can include the outward member segments 14 being replaced by one of the combination segment types depicted in FIG. 17.

FIG. 19 depicts a side view of yet another alternative embodiment of the stent of FIG. 1 in which the chevron-shaped closed cells 13 have outwardly-projecting circumferentially adjustable members 77 at one end 18 and inwardly-projecting members 76 at the other end 17. In alternative stent designs in which the circumferentially adjustable members of a longitudinal segment 14 project outward, significant shortening occurs only in the endmost segments (e.g., segment 25). In this particular embodiment, shortening only occurs at one end segment 14. While the expansion of the interconnection segment 21 contributes a slight amount to overall stent shortening, it makes possible the incorporation of longitudinal segment designs such as those depicted in FIGS. 15–19 without the significant overall shortening that would occur if these segments were directly connected to each other without an interconnection segment, as well as providing lateral flexibility that would be otherwise lacking.

Still yet another longitudinal segment 14 configuration with variable circumferentially adjustable members 76, 76' 77, 77' is depicted in FIG. 20 wherein alternate closed cells 13 are of a different type or design. In this particular embodiment, closed cells 13 having inwardly-projecting circumferentially adjustable members 76, 76' alternate with closed cells 29 having outwardly-projecting members 77, 77'. The overall shortening of this particular stent would be similar to that of the stent designs depicted in FIGS. 15–17. This particular embodiment presents fewer options in how the interconnection segment 21 attaches to the longitudinal segments 14, 25. One solution, which is shown in the figure, is to have a serpentine shaped interconnection strut 80 to maintain proper spacing between the serpentine struts 81 of the interconnection segment and the outwardly-projecting circumferentially adjustable members 77,77'.

FIG. 21 depicts a side view of an alternative embodiment of the stent of FIG. 1 in which a longitudinal segment 14 is elongated by having multiple pairs of circumferentially adjustable members 19, 20, 85, 85', 86, 86' in each closed cell. This particular example has the normal pair of circumferentially adjustable members 19, 20 attached to the first and second longitudinal struts 15, 16. A second pair of circumferentially adjustable members 85, 85' are positioned inside the first pair 19, 20 along the same longitudinal struts 15, 16. A third pair of circumferentially adjustable members 86, 86' are positioned inside the second. The stent can also include two pairs of circumferentially adjustable members, or more than three. The multiple-pair longitudinal segments can stand alone as rigid stents or can be interconnected to other longitudinal segments. While lateral flexibility is obviously reduced in this stent embodiment, the additional circumferentially adjustable members offer increased radial strength.

FIG. 22 depicts a stent 10 having staggered closed cells whereby the basic closed cell 13 is laterally interconnected on each side by two offset closed cells 29, 29', 29", 29'". A longitudinal segment can include rows of alternating single 88 and double 89 closed cells. The longitudinal struts 15, 16 of the single closed cell are longitudinally contiguous with the adjacent longitudinal struts 70, 70', 70", 70'" of the interconnected closed cells 29, 29', 29", 29'". In rows having a single closed cell 88, an additional pair of interconnecting circumferentially adjustable members 87, 87' can be positioned, as illustrated, at the ends of the longitudinal segment to provide an additional interconnection between double closed cell rows 89. This pattern is not limited to alternating single and double closed cell rows. For example, rows of two closed cells can be interconnected to a row of three offset closed cells, and so forth. As with any of the embodiments depicted, a stent of this basic pattern could be made as a single longitudinal segment without the interconnection segments and additional longitudinal segments.

While this disclosure heretofore has concerned various stent embodiments that are expandable using an inflation balloon to plastically deform the stent from a first diameter (as manufactured) to a final diameter in the vessel, it is equally possible to produce a self-expanding version of a pattern substantially similar to any of the previously illustrated embodiments. The preferred material for a self-expanding stent of the present invention would be a superelastic material such as the Ni-Ti alloy known commercially as nitinol. Nitinol is comprised of nearly equal parts of nickel and titanium and can also include small amounts of other metals such as vanadium, chromium, or iron to affect the physical properties such as the transformation temperature of the alloy. The preferred nitinol formulation for this application has a martensitic to austenitic transformation temperature below body temperature, and most preferably, below normal room temperature. The remarkable ability of a superelastic alloy to return to its predetermined shape when subjected to stress, makes it an excellent material for this application. Although certain types of stainless steel and other non-superelastic materials can be used, they are less resilient.

Besides being of a different material, the self-expanding embodiment of the stent differs in that it is formed from the nitinol cannula in an expanded or deployed state, rather than the state of delivery, like the balloon expandable embodiment. The self-expanding stent is radially compressed and loaded into a sheath or catheter which maintains the stent in a deformed condition as depicted in FIG. 25. The constrained self-expanding stent differs slightly in appearance from the unexpanded embodiment of FIG. 1 in that there is evident, a slight distortion of the arms 91 of the circumferentially adjustable members 19, as well as the serpentine bends 81 of the interconnection segment 21. Because of the highly resilient nature of the nitinol, the stent will deploy and expand to its original shape without any plastic deformation having occurred.

FIG. 26 depicts a cross-sectional end view of both an unconstrained and constrained longitudinal segment of the stent of FIG. 25, taken along the line 26—26 of FIG. 25.

FIG. 27 depicts an enlarged partial cross-sectional end view of the stent of FIG. 26, showing how constraining the stent causes the distal bend 59 of the circumferentially adjustable members 19 to move slightly inward, while the arms 91 of the circumferentially adjustable members move slightly outward. The opposite phenomena are usually observed when a balloon expandable embodiment is deployed to its final diameter.

FIG. 28 depicts a stent of the present invention with a preferred arrangement of radiopaque markers 102, 103, 104, 102', 103', 104' at the distal and proximal ends 63, 63'. These markers aid in positioning the stent and determining its exact location under x-ray or fluoroscopy. The preferred method of adding radiopacity is to laser drill a single aperture in the outer portion of longitudinal struts 15 at each end of the stent. A small piece of gold, preferably a 0.010"diameter sphere, is then pressed into the eyelet aperture 96 while a rod (not shown) is placed within the lumen 12 to provide support. Other high density metals can be used for adding radiopacity including platinum, tungsten, iridium, barium, and other like materials. Alternatively, radiopaque markers are positioned in the eyelets by crimping or any other well-known fastening method.

In the embodiment of FIG. 28, there is an eyelet 96 for each of the six cells 13 with the three eyelets of alternate cells being filled with a radiopaque marker. This stent has the markers positioned every 120 along the circumference of the stent in both the unexpanded and expanded state. This is possible because of the tubular design of circumferentially interconnected cells and longitudinal struts that remain aligned with the longitudinal axis of the stent as it expands. The three markers 102, 103, 104 at the first end 63 and the three markers 102', 103', 104' of the second end 63' all lie within respective single planes 105, 106 transverse and, in particular, perpendicular, to the longitudinal axis 42 of the stent such that when the stent is viewed at an angle under fluoroscopy, the spatial orientation of the stent can be accurately determined. Perhaps more importantly, the three-marker arrangement has great benefit in viewing a stent that is lying in a plane perpendicular to the viewing angle (i.e., a side view) as depicted in FIG. 30. It is possible for a single-marker stent to be positioned such that marker 97 is viewed from the side which represents it narrowest profile. Typically, the resolution of the fluoroscopy unit makes it difficult to impossible to discern such a marker given its small size. If a second marker 94 is placed on the same end 63 of the stent in such a manner that it lies substantially perpendicular to the first marker 97, it will be readily visible due to its wide profile (i.e., a top view). Thus, a six-cell stent has an ideal arrangement of three markers to ensure maximum visibility under fluoroscopy. More than three markers would provide little, if any, increase in stent visibility while adding to the cost of manufacture. In an eight-cell stent embodiment 10 as depicted in FIG. 29, a four-marker 98, 99, 100, 101 arrangement can be used.

FIGS. 31–35 depict cross-sectional views of selected embodiments of eyelets which include various means for retaining a radiopaque marker in a stent body 24. FIG. 31 depicts a thread 149 that has been tapped into eyelet 96. The thread in this particular embodiment comprises approximately 1.3 turns. When the small sphere of gold or another radiopaque metal is pressed or melted into the eyelet, the material fills the grooves cut into the eyelet wall, making the radiopaque marker less likely to loosen and fall out. The thread for a 0.010" eyelet is tapped with 0.3 UNM tap, creating a thread diameter of 0.012". Tapping of the thread is done prior to annealing of the stent while the metal is hard and resistant to distortion. A piece of PTFE beading is placed into the lumen of the stent to provide support for the stent while the eyelets are being tapped.

FIG. 32 depicts an eyelet of another preferred stent embodiment having a countersink or chamfer 150 at both the internal 156 and external 155 faces for holding a radiopaque marker. Creating a chamfer 150 at both the outer face edge 163 of the eyelet and the inner face edge 164 of the eyelet by use of a countersinking tool, aids in the retention of the radiopaque marker. The marker material, when pressed into the eyelet, conforms to fill the chamfer, creating a "lip" that helps prevent the inserted marker from eventually sliding out the opposite side.

FIG. 33 depicts a cross-sectional view of an eyelet of a preferred embodiment having both an internal thread 149 and countersink or chamfer 150 for holding a radiopaque marker in place. This combination provides additional assurance that the marker insert will not loosen and fall out. In FIG. 35, a radiopaque marker 48 is shown inserted into the eyelet 96 of FIG. 33. While the inner surface 162 of the marker is flush with the internal surface 156 of the stent 10 where maximum smoothness is highly desirable, there is a protrusion of excess radiopaque material 165, on the outer surface 155 of the stent, formed when the radiopaque bead, which is of a higher volume, is pressed into the eyelet 96. The result is a larger diameter marker that is more visible under fluoroscopy. For example, an eyelet having a diameter of 0.010" can typically hold a gold marker having a diameter, following compression, of 0.018" and that extends approximately 0.001" beyond the outer surface 155 of the stent.

To support the stent as the radiopaque spheres are being pressed into the eyelets, a metallic rod, having an outside diameter nearly as large as the inside diameter of the stent, is placed within the stent lumen (in a process not shown). The close tolerance between the rod and the stent helps provide the flush interface between the inner surfaces of the radiopaque marker and stent as the two are compressed. To insert the radiopaque sphere into the stent eyelet, a standard hand press is used. The metallic rod is attached to the press anvil. The stent is slid over the rod and the sphere of the material is placed in the topmost eyelet. The lateral edge of the press hammer extends slightly beyond the lateral edge of the anvil such that only the extreme distal end of the stent mounted on the rod is compressed during the insertion procedure. The distal face of the hammer contains a stepped receiving portion equal to the diameter of the stent. The sphere is deformed into the eyelet by the face of the press hammer as it simultaneously contacts the stent and an anvil adjacent to the stent.

FIG. 34 depicts a cross-sectional view of an alternative embodiment of the eyelet in which surface irregularities 151, produced by a method such as grit blasting or acid etching, help provide a better interlock between the radiopaque marker and internal surface 157 of the eyelet 96.

FIG. 36 depicts a partially sectioned, pictorial view of an alternative embodiment of the stent of FIG. 1 in which one or more radiopaque markers 161, 161', 161", 161'" are placed to indicate the position of an open cell or region 160 within the stent. The purpose of the open cell is for alignment with the opening to a side branch 166 from the main vessel 168. In the illustrative embodiment, four radiopaque markers are positioned in two adjacent longitudinal struts 148, 148' surrounding the aperture 160, permitting the physician to more easily accomplish the desired alignment. Under fluoroscopy or x-ray, the markers correspond to the four corners defining the approximate boundaries of the aperture. While the side branch aperture comprises only a single cell in the illustrative example, it should be appreciated that more that one cell may be opened to create a larger aperture within the stent.

FIG. 37 depicts an alternate marker embodiment 167 of stent 10 that is "T" shaped, rather than circular. In the embodiment shown, the marker is formed in the longitudinal strut 15 of the stent 10. The descending or vertical leg 168 of the "T" is aligned with the longitudinal axis 42 of the stent, while the horizontal element 169 of the "T"-shaped marker is aligned with transverse or circumferential plane of the stent. Having markers at both ends of the stent is important for determining its longitudinal boundaries under fluoroscopy; however, the multiple component marker should indicate the spatial orientation of the stent without requiring additional markers to form a plane for providing the same function. In addition, an "L"-shaped marker can be used to accomplish the same goal, especially if one leg was made longer than the other. Other marker shapes are possible which include at least two components, each aligned in a single axis, preferably, the longitudinal axis and transverse plane thereto.

While the illustrated embodiments of the present invention widely vary in appearance, all possess basic common features. The multisegmented version of each stent is comprised of a series of rigid or substantially rigid longitudinal segments of high radial strength or stiffness, each comprised of a series of laterally interconnected closed cells. The longitudinal segments are interconnected by flexible interconnection segments comprised of a series of linear or curvilinear struts. The interconnection segments distribute the bending forces to permit lateral elastic deflection (lateral flexibility) of the stent and to allow for radial expansion of the stent with minimal shortening. The individual longitudinal segments have stable axial length during expansion as defined by the longitudinal strut length. During balloon expansion in which the circumferentially adjustable members that interconnect the longitudinal struts of each cell are plastically deformed, the longitudinal struts of a given longitudinal segment are pulled apart, but remain circumferentially aligned and within the original longitudinal plane. Shortening of longitudinal segments only occurs at the distal and/or proximal end of a stent having outwardly projecting circumferentially adjustable members. The stent length, as defined by the distance between proximal and distal radiopaque markers, is not changed.

Any of the longitudinal segment types disclosed herein can be combined in a given stent so long as the segments are interconnected at one or more longitudinal struts to or by an interconnection segment that can expand with the longitudinal segments and not interfere with lateral flexibility. These possibilities include designs having a varying number of closed cells across the longitudinal segments of a single stent for the purpose of creating a taper or narrowed zone within the stent when expanded. Another method of producing a taper or narrowed portion is to vary the length of the longitudinal struts and/or circumferentially adjustable members to produce longitudinal segments that expand to different diameters. A design employing more than one method of varying the expanded stent diameter can be used. Inflation of a variable diameter stent can be accomplished with a segmented or specially shaped balloon. Another method of creating such a stent with a conventional balloon can include varying the thickness or angle of the circumferentially adjustable struts so that the longitudinal segments require different inflation pressures to fully expand.

In addition to combining more than one type of longitudinal segment within a given stent, it is also possible to vary the design of the interconnection segments within a stent to produce local differences in flexibility. For example, a stent can be designed to be more or less flexible in the middle portion or at one end to correspond to the actual or desired shape of the target vessel. In addition, the interconnected curvilinear struts can be variable within a single interconnection segment to include bends of different sizes, angles, thicknesses, fillet shapes, etc., to meet spatial needs and produce the desired bending properties. It is to be understood that the above-described stents are merely illustrative embodiments of the principles of this invention and that other stents may be devised by those skilled in the art without departing from the spirit and scope of this invention.

The following describes the design of the new Supra$^3$ stent 10 depicted in FIGS. 1 and 38. The design covers both coronary and peripheral use.

The Supra$^3$ stent 10 is designed to exceed the performance of any stent currently on the market.

Briefly, the Supra$^3$ stent design is more flexible in bending, has less recoil, and is radially stiffer and stronger than other commercially available or known stents.

In addition to these features, the Supra$^3$ stent has many other design and performance features that minimize or eliminate problems in other stent designs.

Unlike previous designs, the Supra$^3$ stent design has been extensively analyzed using sophisticated computer simulation models based on finite element analysis (FEA). The simulation allowed numerous design iterations and what-if modeling to occur before physical prototypes were needed. The mechanical simulation also provided insight into how the design behaves and gave direction on how to improve the concept during the design phase. This intensive design effort could not have been accomplished using prototype testing alone.

This section contains a brief summary of the important design and performance features of the Supra$^3$ stent design. During stent delivery, these features allow the Supra$^3$ stent to easily and reliably reach the lesion site:

High bending flexibility (high trackability)

High free end stiffness to minimize end flare

High stent-to-balloon crimp force to minimize slippage

Greater crimp force retention when bent to minimize slippage

High pull-out stiffness of internal loops to minimize damage during handling and use Radio-opaque end markers to aid stent positioning During balloon expansion, these features allow the Supra$^3$ stent to be reliably and consistently expanded at the lesion site:

Stable expansion without popping open

Circumferentially uniform expansion

Repeatable expansion from stent to stent

Large expansion ratio

Built-in overexpansion capability

Minimal change in length during balloon expansion

Minimal dog-boning during expansion

The entire Supra$^3$ stent participates in the expansion unlike other stent designs Radio-opaque markers are distributed around the circumference providing the possibility of viewing and measuring the expanded stent diameter fluoroscopically After balloon withdrawal, these features provide the Supra$^3$ stent with excellent performance as an implanted device:

Very low elastic recoil

Circular, smooth lumen shape

Good scaffolding and distribution of metal within the expanded stent

Less gap opening between cells when bent

High radial stiffness

High radial strength

High bending fatigue life

High pulsatile fatigue life

The Supra$^3$ stent 10 has been intentionally designed to meet or exceed the performance of all of the major competitive stents currently available. The Supra$^3$ stent 10 comprised of a series of laterally connected cells 13 joined around the circumference. At the outermost ends of the stent are hoop cell segments 14. Adjacent to and interconnecting the hoop cell segments are flex cell interconnection segments 21. The hoop and flex cell segments alternate regularly along the stent.

The hoop cell segments 14 are comprised of a series of scissor-jack sections arranged circumferentially. FIG. 39 depicts a typical hoop cell segment 14 containing scissor-jacks and axial bars or struts 15.

The hoop cell segment 14 is composed of rows of axial bars 15 arranged circumferentially. Each axial bar spans the entire length of the hoop cell segment.

Connecting the axial bars 15 are the scissor-jacks 19 and 20 (circumferentially adjustable members) shown in FIG. 40, whereby U-shaped members double back to connect the adjacent ends of the axial bars. The bottom loops of the scissor-jacks have been intentionally enlarged relative to the spacing between each leg of the scissor-jack. The enlarged loop provides maximum flexibility and fatigue life. The axial bars are scalloped width-wise to provide the extra space for the enlarged scissor-jack loops.

Connecting the hoop cell segments 14 together are flex cell interconnection segments 21 shown in FIG. 40. The flex cell segments are comprised of "Z" or "S" shapes snaked around the stent circumference.

The hoop and flex cell segments are connected together by small tabs, struts, or members 36 at a single point between one of the bends in the flex cell segment and one of the axial bars in the hoop cell segment. This is illustrated in FIG. 40. The opposing connecting tab 36 (not visible in this view) at the other end of the flex cell segment is connected across a loop in the flex cell segment 180° opposed from the first tab. This type of hoop-to-flex cell connection is called the one-point design.

The hoop-to-flex cell segment connecting tabs are not articulations as used in other stents. An articulation in the Palmaz-Schatz stent (FIGS. 46 and 47), for example, provides bending flexibility between the two rigid Palmaz sections.

In the Supra$^3$ stent design, the hoop-to-flex cell connecting tabs do not provide significant bending flexibility to the design. Instead, the flex cell segment and the staggered nature of the connection between the hoop and flex cell segments. provide the very high bending flexibility of the Supra stent. The connecting tab 36 itself is simply a joining element with no additional structural function.

A variation in the hoop-to-flex cell connection is to add connecting tabs between other loops in the flex cell segment. For example, in FIG. 41, there are three connections 36 between each hoop and flex cell segment pair spaced equally around the circumference.

The one-point and multi-point designs have certain advantages and disadvantages compared to each other and to other stents. These will be highlighted, as needed. The primary advantage of the one-point design is very high bending flexibility. The primary advantage of the multi-point design is lower prolapse opening between hoop and flex cell segments when the stent is expanded in a curved artery.

For coronary applications, the Supra$^3$ stent can range from 2.5 to 5 mm diameter in lengths from 10 to 40 mm. For peripheral applications, the stent can range in size from 4 to 16 mm and in diameter in lengths from 20 to 60 mm.

The Supra$^3$ stent is balloon expandable. Like the Flexstent and GR II® stents, the Supra$^3$ stent will be crimped onto a balloon and will not incorporate a protective outer sheath.

A typical expanded stent 10 shape is depicted in FIG. 5.

In FIG. 42, the expanded shape of the Supra$^3$ stent shows very good tissue coverage and an even distribution of metal along the length and around the circumference of the stent. These features occur because each flex cell segment 21 expands along with its neighboring hoop cell segment 14 and its struts 81 fill in the gap between the open scissor-jacks 19, 20 as indicated.

The coronary Supra$^3$ stent is laser cut from annealed, thin walled 316 LVM stainless steel cannula with wall thickness of 0.005" and outer diameters of 0.054" to 0.070". The peripheral Supra$^3$ stent is laser cut from cannula with wall thickness of 0.006" and outer diameters of 0.083" to 0.123". At these thicknesses, the body of the stent itself is moderately opaque fluoroscopically.

The Supra$^3$ stent design does not use welding (unlike the GFX stent) to connect different parts of the stent. The entire stent is made from a single piece of cannula tubing.

Following laser cutting, the Supra$^3$ stent is electropolished to provide a smooth surface without sharp corners or edges.

The Supra$^3$ stent design concept is not restricted to stainless steel. Other materials can be used.

It is even possible that the Supra$^3$ stent design concept can form the basis of a self-expanding stent made from Nitinol as previously described.

The Supra$^3$ stent has three built-in radio-opaque markers at each free end to indicate the stent position by fluoroscopy. The markers are distributed around the circumference so that the expanded stent diameter is directly visible by fluoroscopy.

Since the Supra$^3$ stent is continually connected around the circumference (unlike the GR II® stent, for example), the stent can easily be overexpanded to larger diameters.

The capability for overexpansion has been designed into the Supra$^3$ stent to ensure good performance at both nominal and the overexpanded diameters seen in FIGS. 42 and 43. In particular, the bending fatigue estimates performed during the design were done on the overexpanded stent.

A major advantage of the Supra$^3$ stent design is that length and diameter are almost arbitrary and can be chosen to meet other design criteria. For example, to increase the stent length, add additional pairs of flex and hoop cell segments axially. To increase the stent diameter, additional scissor-jack cells are inserted around the circumference of the hoop cell segment. The circumferential length of the flex cell segment is also increased.

The only design constraint is that the rotating tube fatigue life of the stent is directly affected by the length and width of the scissor-jack and flex cell segment legs. Design modifications to these regions cannot be made without re-verifying fatigue life.

This scalability feature allows the Supra$^3$ stent design concept to be used for both coronary and peripheral uses.

This section briefly describes the competing stents. These stents have been analyzed in exactly the same way as the Supra$^3$ stent. In this way, the predicted performance of the Supra $^3$ stent design can be directly compared to existing stents.

The GR II® stent is a Cook Incorporated stent made from flat 0.003" thick stainless steel foil shown in FIGS. 44 and 45. The stent loops 110 unfold circumferentially. The axial spine 111 stabilizes the loops.

The Palmaz-Schatz stent shown in FIGS. 46 and 47 is manufactured by Johnson and Johnson (now Cordis). It is the original slotted tube design made from stainless steel cannula. The Palmaz-Schatz stent consists of two Palmaz sections 112 linked by an articulation 113 to provide bending flexibility.

The ACS Multilink stent is also a cannula stent design shown in FIGS. 48 and 49. It incorporates a series of circumferential "S"-shaped rings 114 alternately connected by thin axial bars 115.

The GFX stent shown in FIGS. 50 and 51 is another new generation stent. It is made from "S"-shaped rings 116 that are welded together axially. The welds 117 occur at only a single point from one ring to another.

A final cannula stent is the NIR stent shown in FIGS. 52 and 53.

The following details the performance of the Supra$^3$ stent. The performance of the Supra $^3$ stent is directly compared to the other stents.

Throughout this section, the same analysis procedures have been applied to the Supra$^3$ stent as to the competing stents.

For the Supra'stent, the geometry of the computer model was constructed from drawings of the stent plus optical measurements of the dimensions of the stent after electropolishing. The material properties were taken from prior work on the analysis of the GR II® stent. These properties are shown in Table 1.

TABLE 1

Representative 316L material properties used in all stent models

| Property | Value |
|---|---|
| Elastic Modulus | $30 \times 10^6$ psi |
| Poisson's Ratio | 0.29 |
| Yield stress | 44,634 psi |
| Ultimate stress | 93,702 psi |
| Strain at ultimate | 59.5% |
| Endurance limit | Same as yield |

For the competing stents, no engineering drawings were available so the stent models were created from visual measurements of the stents using a high powered microscope with optical measuring capabilities.

The material properties of the competing stents have also been assumed to be the same as for the Supra$^3$ stent. In this way, the results of the analysis of the competing stents provide direct relative comparison of the merits of the Supra$^3$ stent design compared to stents currently approved and on the market.

To reach the lesion site, the stent/balloon system must be moved through a guide catheter and out into the body passageway. During positioning, the stent/balloon is pushed and bent through a tortuous path. The following properties show that the Supra'stent should be able to be inserted up to and in position as well as or better than competing stents.

Many aspects of the stent/catheter system determine its trackability. The stent design itself impacts trackability in two ways: curvability and bending flexibility.

Both of these properties are measured by bending the undeformed stent models through a large angle 118 with a bending force 119 (moment) as shown in FIG. 54.

Curvability is the ability of the stent to conform to a curve when bent.

A stent that is highly curvable lies along the curve whereas a stent that is not curvable will not easily conform to a curve when bent.

To analyze relative curvability of two stents, compare the displaced shapes of the stents when bent around the same curve.

FIGS. 55–59 show the bent shapes of the Supra$^3$ stent and competing stents. The Palmaz-Schatz stent design is not curvable since its long segments do not conform to the curve.

On the other hand, the Supra$^3$ stent is highly curvable due to the fact that its hoop cell segments are short and there are many of them along the length of the stent. The Supra$^3$ stent easily conforms to the bent curve.

To measure bending flexibility, the stent models are bent through an angle. The forces (bending moments) needed to bend the stent are predicted during the analysis based on stent geometry and material response. The lower the forces required to bend the stent, the better the trackability. Since the lengths of the various stents are not equal, the results have been adjusted for comparison purposes to show the results for a nominal 15 mm long stent of each design.

From the bending analysis, several performance parameters can be measured: bending stiffness, bending strength, and elastic bending angle range.

The elastic bending stiffness of a stent is the initial elastic slope of the bending moment vs. deflection curve. A low bending stiffness is desired since bending stiffness is related to fatigue endurance (discussed later).

The results of the bending stiffness analysis are summarized in Table 2. The bending stiffness results have units of bending moment (in-lbf) per degree of total bend at the end of a nominal 15 mm long stent in the unexpanded shape. The third column lists the ratio of the elastic bending stiffness for each stent normalized by the stiffness value of the 0.002" thick Multilink. The lower the elastic bending stiffness, the more easily the stent can be bent through a small angle. The fourth column lists stiffness per unit length (mm) [lbs (force) per millimeter (length)].

TABLE 2

Summary of the elastic bending stiffness for the various stents

| Stent | Elastic Bending Stiffness | Ratio (of Multilink) | Unit Length Stiffness |
|---|---|---|---|
| Supra$^3$ | $0.1 \times 10^{-4}$ | 0.11 | $7.3 \times 10^{-7}$ |
| GFX | $0.5 \times 10^{-4}$ | 0.56 | $3.3 \times 10^{-6}$ |

TABLE 2-continued

Summary of the elastic bending stiffness for the various stents

| Stent | Elastic Bending Stiffness | Ratio (of Multilink) | Unit Length Stiffness |
|---|---|---|---|
| Multilink (t = 0.002") | $0.9 \times 10^{-4}$ | 1.00 | $6.0 \times 10^{-6}$ |
| Multilink (t = 0.004") | $2.1 \times 10^{-4}$ | 2.33 | $1.4 \times 10^{-5}$ |
| NIR | $8.0 \times 10^{-4}$ | 8.89 | $5.3 \times 10^{-5}$ |

The bending strength of a stent is the maximum value of the bending moment that the stent generates during bending. The bending strength is limited by stent design and material plasticity. A low bending strength is desirable since it enables a stent to be more easily tracked and pushed around a curve in a vessel.

The results of the bending strength analysis are summarized in Table 3. The bending strength values have units of total moment (in-lbf) applied to a nominal 15 mm long stent at the unexpanded diameter to bend the tip through a 30° angle. The lower the bending strength, the more easily the stent can be bent through a large angle.

TABLE 3

Summary of the bending strength of the various stents

| Stent | Bending Strength | Ratio (of Multilink) |
|---|---|---|
| Supra$^3$ | $0.3 \times 10^{-3}$ | 0.12 |
| GFX | $1.5 \times 10^{-3}$ | 0.60 |
| Multilink (t = 0.002") | $2.5 \times 10^{-3}$ | 1.00 |
| Multilink (t = 0.004") | $5.1 \times 10^{-3}$ | 2.04 |
| NIR | $8.2 \times 10^{-3}$ | 3.28 |

The elastic bending angle range is the amount of bending angle the stent can be bent through before plastic deformation in the stent occurs. For bending to larger angles than this value, the stent suffers permanent bending deformation much like a paper clip will be bent open permanently when it is opened to a large angle. The larger the elastic bending angle range, the more durable the stent over a lifetime of heartbeat cycles.

The elastic bending angle ranges are summarized in Table 4. The units are total tip rotation angle in an unexpanded nominal 15 mm long stent. The bending analysis was performed only to a 30° bend angle per 15 mm nominal length stent. The higher the elastic bending angle range, the lower the amount of plastic deformation induced in the stent for a given bend angle. For the Supra$^3$ and GFX stents, the elastic bending angle range was found to exceed 30°.

TABLE 4

Summary of the elastic bending angle ranges for the various stents

| Stent | Elastic Bending Angle Range | Ratio (of Multilink) |
|---|---|---|
| Supra$^3$ | >30° | >1.76 |
| GFX | >30° | >1.76 |
| Multilink (t = 0.002") | 18° | 1.00 |
| Multilink (t = 0.004") | 17° | 0.94 |
| NIR | 7° | 0.39 |

A protective sheath need not be used to cover the Supra$^3$ stent. Consequently, it is important that the stent be tightly crimped onto the folded balloon. The forces generated during crimping depend on the stent design, the compliance of the folded balloon, and the crimping process. However, the force remaining between the folded balloon and stent after crimping is completed depends mainly on the stent itself and its radial stiffness in the unexpanded position.

To assess the ability of the various stent models to generate and maintain crimp forces, the stent models were mounted on identical, slightly oversized balloon models of equal compliance. In response to the interference fit between the stent and balloon, the stent expands outward slightly and the balloon contracts inward. The force generated between the balloon and stent provides a relative indication of how tightly the stent can be crimped onto a balloon.

The results are summarized in Table 5. The higher the initial stent-to-balloon force, the more tightly the stent is able to be crimped onto the folded balloon and the less likely the stent is to slip or become dislodged from the straight balloon.

TABLE 5

Summary of Stent/Balloon Force on a Straight Balloon

| Stent | Initial Stent-to-Balloon Force | Ratio (of Multilink) |
|---|---|---|
| Supra$^3$ | 0.446 | 2.32 |
| GFX | 0.382 | 1.99 |
| Multilink (t = 0.002") | 0.192 | 1.00 |

The stent-to-balloon force analysis shows how tightly the entire stent grips the balloon after crimping. Also of importance is how tightly the free ends of the stent grip the balloon. The entire stent can grip the balloon tightly, but if the free end is easily pulled away from the balloon, the free ends can flare away from the balloon, and the stent can become jammed or otherwise damaged during insertion.

To assess the tendency of the Supra$^3$ stent to flare at its free ends, the unexpanded stent is mounted on the slightly oversized tube representing a folded balloon, then bent downward, re-straightened and bent upward, then re-straightened again as shown in FIGS. 60–64.

FIG. 67 shows that the free end of the Supra$^3$ stent remains flush with the balloon after bending and re-straightening. A stent design with a greater tendency to remain flush with the balloon after bending and re-straightening is less likely to slip or become dislodged from the balloon.

The behavior of the Supra$^3$ stent is directly related to its design. The axial bars in the hoop cells adjacent the free end help distribute the effects of the bending of the tube away from the free end. They help to push the scissor-jack ends down onto the balloon at the free end.

The Multilink stent as depicted in FIG. 66 does not have this desirable property. Its free ends tend to flare upward away from the balloon. This is due to the particular design of the Multilink stent. The circumferential loops at the free end of the Multilink stent are only connected by axial bars at the inboard end of the loops. These bars are ineffective in transferring the effects of bending into the stent away from the free ends. Consequently, the free ends bear the brunt of the bending forces and flare outward. The GFX stent ends are depicted in FIG. 65.

After being bent and restraightened, the stent-to-balloon contact force should remain high. Otherwise, the stent can stay securely on the balloon while the catheter is straight, but may loosen and slip off the balloon after it is bent.

Comparison of the force levels between the various stents after crimping and bending shows that the Supra$^3$ stent has both a higher stent/balloon force before bending and it retains a higher percentage of this force after bending. This comparison is shown in Table 6.

TABLE 6

Summary of stent/balloon force bending and re-straightening

| Stent | Stent-to-Balloon Force Retained after Bending | Ratio (of Multilink) | Percentage of Initial Force Retained after Bending |
|---|---|---|---|
| $Supra^3$ | 0.333 | 2.97 | 75% |
| GFX | 0.274 | 2.45 | 72% |
| Multilink (t = 0.002") | 0.112 | 1.00 | 58% |

Table 6 shows that the $Supra^3$ stent should be less likely than other stents to slip on the balloon after it is pushed through the sharp bends in the guide catheter.

Another important aspect of bending the unexpanded stent/balloon system is that the stent must not deform away from the balloon during bending. The scissor-jack and "Z"-shaped section loops all tend to bend upward away from the balloon during bending. It is important that these loops not get caught on surrounding tissue during stent motion through a curved passageway.

To estimate whether the $Supra^3$ stent is liable for this effect, the force needed to lift the loops up away from the balloon can be analyzed as shown in FIG. 68.

The results of the loop lift-away analysis are summarized in Table 7.

TABLE 7

Loop Pull-out Force Summary

| Stent | Force to lift loop end 0.004" (lbf) | Ratio (of Multilink) |
|---|---|---|
| GFX | 0.058 | 7.25 |
| $Supra^3$ scissor-jack loop | 0.050 | 6.25 |
| $Supra^3$ flex loop | 0.037 | 4.63 |
| Multilink (t = 0.004") | 0.034 | 4.25 |
| Multilink (t = 0.002") | 0.008 | 1.00 |

Compared to the 0.002" thick Multilink stent, the force required to lift the $Supra^3$ stent loops away from the stent is more than 4 times larger. The GFX stent has the largest loop pull-out force at more than 7 times the Multilink stent.

Once positioned at the lesion site, the balloon is inflated and the stent is expanded.

FIGS. 43, 45, 47, 49, 51, and 53 show side views of the expanded $Supra^3$ stent and its competition.

The GR II® stent of FIG. 45 opens circumferentially. Due to the space between the loops on the GR II® stent, the expanded shape looks scalloped fluoroscopically.

The Palmaz-Schatz stent of FIG. 47 suffers from an unstable expansion behavior that produces outwardly projecting edges and a non-uniform expansion around the circumference.

The GFX stent of FIG. 49 has relatively large diamond-shaped gaps that open further as the stent is expanded.

The $Supra^3$ stent expands in a way that minimizes gapping between the bars of the stent. This is due to the fact that the flex cells also expand and fill the diamond-shaped openings of adjacent scissor-jack sections.

The $Supra^3$ stent is stable during expansion. It does not pop open suddenly.

The stability of the stent expansion can be determined by measuring the balloon-to-stent forces that occur during expansion.

The results show that the GR II® and Palmaz-Schatz stents are not stable during expansion. Both of them pop open. The GR II® stent pops open due to the circumferential unfolding that accompanies the radial expansion of the device. The Palmaz-Schatz stent pops open due to the sudden twisting (lateral buckling) of the struts.

The $Supra^3$ stent design (along with the ACS, GFX, and NIR stents) is stable during expansion and does not pop open.

Due to the buckling instability during expansion of the Palmaz-Schatz stents, the stent expands unequally around the circumference. This means that some cells in the Palmaz-Schatz stent will be overexpanded and some will be underexpanded around the circumference.

This also means that no two Palmaz-Schatz stents are likely to expand in exactly the same way since the twisting instability will be slightly different in each sample: some will expand uniformly, some will expand mildly nonuniformly, and some will expand grossly nonuniformly.

The $Supra^3$ stent will expand more uniformly since it is stable during expansion: each $Supra^3$ stent should expand like any other $Supra^3$ stent in a more repeatable fashion.

The Multilink, GFX, and NIR stents also expand uniformly due to their cellular structure. These stents should expand repeatably.

The scissor-jack concept allows the $Supra^3$ stent to have a large expansion ratio and to be expanded significantly from a small initial diameter to a large final diameter.

The axial bars in the hoop cell segments of the $Supra^3$ stent minimize change in axial length during expansion. For example, the axial length of the expanded hoop cell segment is the same as the axial length of the unexpanded hoop cell segment. The only change in length occurs due to a change in angle of the legs in the flex cell segment section.

Length change results for the various stents are shown in Table 8.

TABLE 8

Foreshortening during expansion

| Stent | Percentage Length Decrease During Expansion |
|---|---|
| GFX | 1.4% |
| $Supra^3$ | 3.8% |
| Multilink (t = 0.002") | 5.1% |
| PS1530 | 5.2% |
| NIR | 5.5% |

The very low length change in the GFX is due to the fact that each of the straight bars in each sinusoidal section of the GFX are angled opposite its neighboring bar. When the stent expands, the bars will first be straight and the stent length will increase. Upon further expansion, the bars will begin to angle away from each other and the stent will shorten. The GFX design has balanced the lengthening and shortening in such a way that the total length change is minimized.

The hoop cell segments of the $Supra^3$ stent never change length during expansion due to the axial bars. The angles of the bars in the Z-section could be opposed in the unexpanded stent so that the length change is balanced during expansion.

Another benefit of the stiff axial bars in the hoop cell segments is that the $Supra^3$ stent will be much more resistant to dog boning during expansion than, for example, the GR II® stent. Dog-boning occurs when the free ends of the stent expand fully before the middle of the stent starts to expand. In the GR II® stent, it is due to the unstable expansion and the lack of support in the end loop from the adjacent loop.

The isolated loop at the free end is unable to resist the greater expansion pressure of the balloon shoulder.

In the Supra$^3$ stent, the axial bars transfer the expansion loads inward away from the free end. At the same time, the free end is stiffened by the greater support of the axial bars and is less able to lift away from the overall cylindrical profile of the stent.

An additional feature of the Supra$^3$ stent design is that both the hoop and flex cell segments participate in expansion due to the offset nature of the hoop-to-flex cell connection. This offset pulls the "Z"-shaped sections in the flex cell segment open circumferentially.

Compare this to the NIR stent in which the short U-shaped articulations between circumferential elements do not participate in the expansion.

After the stent is expanded, the balloon is deflated and withdrawn leaving the stent in position to prop open the lumen and support the surrounding tissue. Designed into the Supra$^3$ stent are features that provide significant performance enhancements during this phase compared to competing stents.

Recoil of a stent is a measure of how much the stent's diameter decreases between the point of full balloon inflation against the expanded stent and full balloon deflation.

There are two components to the total elastic recoil in a stent: the elastic recoil of the stent itself and the further reduction in diameter due to radially inward pressure from the surrounding tissue. To minimize the portion of the recoil due to tissue pressure, select a stent with high radial stiffness.

The second component of the total recoil, the elastic recoil of the stent itself, is related to the stent's design and will vary from stent to stent.

Elastic recoil due to the stent design only is summarized in Table 9.

TABLE 9

Summary of elastic recoil

| Stent | Recoil Percentage |
|---|---|
| Supra$^3$ | 1.5% |
| Multilink (t = 0.002") | 3.3% |
| Multilink (t = 0.004") | 3.5% |
| GFX | 4.4% |
| NIR | 4.3% |
| PS1530 | 4.7% |

The Supra$^3$ stent design has very low elastic recoil compared to competing stents. The elastic recoil is analyzed by simply taking the percentage difference between the stent diameter at maximum balloon inflation and the stent diameter after balloon deflation. These values do not include the effects of surrounding tissue on recoil.

Table 9 shows that the elastic recoil of the Supra$^3$ stent is nearly three times lower than the GFX stent and more than two times lower than the Multilink stent.

FIGS. 69–74 show end views of the expanded shapes of all of the stents analyzed in this report. The Palmaz-Schatz stent in FIG. 70 (PS 1350 ) shows the outwardly projecting edges due to twisting of the struts. The GR II® stent in FIG. 74 shows that the tips of the stent are not uncurled by expansion. The NIR stent (FIG. 73) shows the connecting U-shaped tabs remain down slightly into the lumen. The expansion forces against the NIR are not capable of changing the curvature of the U-shaped tabs.

The Supra$^3$ stent, however, shows (FIG. 69) a nearly circular cross section without any parts of the stent projecting into or out of the general shape of the expanded cylinder. This occurs because both the hoop and flex cell segments participate in the balloon expansion.

Both the hoop and flex cell segments participate in the expansion and are opened circumferentially and radially expanded. However, each cell opens independently due to the one point connection between neighboring cells. In this way, the expansion of the flex cell segments helps fill the diamond-shaped gap between the neighboring hoop cell segments.

When any stent composed of cells is expanded in a bent position, small gaps open between the cells. This effect is minimized by the short hoop cell length of the Supra$^3$ stent compared, for example, to the length of the cells in the Palmaz-Schatz stent. In the Palmaz-Schatz stent, the prolapse gap is a much larger percentage of the stent length. Refer back to FIG. 13. The gap in the Supra$^3$ stent is much less.

The ability of a stent to support the tissue surrounding it is related to its radial strength and stiffness.

A stent with high radial stiffness will change diameter less than a stent with lower radial stiffness when the same external force is applied. Therefore, to minimize the cyclic contraction in the stent due to blood pressure and tissue pressure, high radial stiffness devices are desired.

To analyze the radial stiffness of the various stent models, total radial force vs. diameter change was measured for the various devices at the end of balloon expansion. These results are listed in Table 10. The units for radial stiffness are total radial force (lbf) over a nominal 15 mm long stent per thousandth inch (0.001") diameter change. The higher the stiffness, the lower the diameter change for a given radial load. Stiffness in per unit length (mm) is also provided in column 4 of Table 10.

TABLE 10

Summary of radial stiffness

| Stent | Radial Stiffness (expanded) | Ratio (to Multilink) | Per Unit Length Radial Stiffness (expanded) |
|---|---|---|---|
| Supra$^3$ | 1.734 | 7.22 | $4.8 \times 10^{-1}$ |
| GFX | 0.521 | 2.17 | $3.47 \times 10^{-2}$ |
| Multilink (t = 0.002") | 0.240 | 1.00 | $1.6 \times 10^{-2}$ |
| NIR | 0.129 | 0.54 | $8.6 \times 10^{-3}$ |
| PS1530 | 0.073 | 0.31 | $4.87 \times 10^{-3}$ |

As stated previously, the ability of a stent to support the tissue surrounding it is related to its radial strength and stiffness.

A stent with high radial strength will hold a vessel open longer without crushing than a stent of lower radial strength when increasing external force is applied. High radial strength is desirable in a peripheral stent.

To compare the radial strength of the various stents, the total amount of force needed to fully expand each stent (adjusted for a nominal 15 mm long stent) was compared. In principle, the amount of force needed to expand an unexpanded stent will be equal to the amount of force needed to crush an expanded stent.

TABLE 11

Summary of radial strength

| Stent | Radial Strength | Ratio (to Multilink) |
|---|---|---|
| Supra$^3$ | 6.611 | 3.19 |
| GFX | 5.559 | 2.68 |
| Multilink (t = 0.002") | 2.071 | 1.00 |
| NIR | 1.436 | 0.68 |
| PS1530 | 0.991 | 0.48 |

The ACS Multilink Duet stent was not analyzed during this project. However, marketing literature from ACS claims that the Duet stent has about 3.1 times the radial strength of the original Multilink. The Multilink Duet stent has the same circumferential structure as the original Multilink stent with slightly modified axial structure. It is believed to be 0.004" thick.

The GR II® stent is known to have a high bending fatigue life based on testing of the stent in Cook Incorporated's rotating tube test machine. This experimental result can be verified by conducting a bending fatigue analysis on the expanded stent.

The FDA has used the bending fatigue analysis to help judge the safety of stents when only limited test data is available. Consequently, the fatigue analysis is very important in stent design. During the initial phase of the Supra$^3$ stent design, this was the only design criteria: the objective of the initial phases was to identify a design that would survive the rotating tube test.

Rotating tube fatigue analysis results are plotted on a Goodman diagram that shows how close the bent stent is to a fatigue boundary.

The Supra$^3$ stent design falls below the fatigue boundary showing that it is expected to survive the rotating tube test.

Since complete material stiffness and fatigue behavior was not available for the competing stents, the fatigue results are useful in comparison with the Supra$^3$ stent to judge the merits of the designs, but should not be used to claim that particular designs would or would not survive the bending fatigue test.

FIGS. 75–80 are Goodman diagrams. A Goodman diagram is used to predict whether a device will survive a particular fatigue test or whether it will break. During cyclic loading, the stress in the device is split into a constant portion and a cyclic portion. On the x-axis of a Goodman diagram is plotted the mean (constant) part of the stress. On the y-axis is plotted the alternating (cyclic) part of the stress. Each point in the stent is plotted as a square on the diagram depending on the values of the mean and alternating parts of the stress.

Also plotted in the diagram is the Goodman line that runs from the material's ultimate tensile stress on the x-axis to the material's endurance limit on the y-axis. The ultimate stress is that stress at which the material breaks due to a single slow pulling load. The endurance limit is that stress below which the material survives fully reversed cyclic loading. At stresses above the endurance limit, the material fails in fatigue under fully reversed loading.

The Goodman line divides the plot into two areas. If the stress points fall below the Goodman line, the stent will not suffer fatigue failures at that point. If the stress points fall above the Goodman line, the stent is predicted to fail in fatigue during cyclic loading.

FIG. 75 depicts the Goodman diagram for rotating tube fatigue of the GR II® stent.

FIG. 76 depicts the Goodman diagram for rotating tube fatigue of the Supra$^3$ stent.

FIG. 77 depicts the Goodman diagram for rotating tube fatigue of the Multilink stent.

FIG. 78 depicts the Goodman diagram for rotating tube fatigue of the GFX stent.

FIG. 79 depicts the Goodman diagram for rotating tube fatigue of the NIR stent.

These diagrams show that the GFX stent would be expected to have about the same bending fatigue endurance as the Supra$^3$ stent were the GFX stent to be made from the same material as the Supra$^3$ stent. On the other hand, the diagrams show that the Multilink and NIR stents would be less likely to survive bending fatigue loading than the Supra$^3$ stent.

For peripheral use, the bending fatigue is less important than pulsatile fatigue. Pulsatile fatigue is the fatigue resistance of the stent to pulsing radial loads, such as blood pressure loads. In practice, pulsatile fatigue is tested by expanding the stent into a flexible tube that is then filled with a fluid and pulsed rapidly to alter the diameter of the stent cyclically.

FIG. 80 shows a Goodman diagram for pulsatile fatigue loading on a Supra$^3$ stent. All of the points are well below the Goodman line leading to the conclusion that the Supra$^3$ stent would survive pulsatile loading through 10 years of heartbeat cycles. Comparison of this diagram with the bending fatigue diagram shown above for the Supra$^3$ stent further shows that of the two types of loading, bending fatigue is more severe (and is more of a design constraint) than pulsatile loading.

The Supra$^3$ stent has been intentionally designed to meet or exceed the mechanical performance of any other competitive stent. This was accomplished through use of sophisticated computerized modeling of the stent's behavior during the design cycle.

The conventional wisdom in stent design is that there is a trade-off between high radial stiffness and high bending flexibility. Present devices generally possess one or the other characteristic. The Supra$^3$ stent achieves both without need for a trade-off.

This is achieved by decoupling the radial (circumferential) behavior of the stent from the bending (axial) behavior. The radial performance is provided by the hoop cell segments containing scissor-jack sections joining axial bars. The bending performance is provided by the flex cell segment and its one-point offset connection between cells.

The final Supra$^3$ stent design provides very low elastic recoil and high radial strength and stiffness in a stent that also has very high bending flexibility. High radial stiffness also provides for high forces between the crimped stent and the balloon. Foreshortening during expansion is minimized by the axial bars, and the final lumen shape is nearly circular since both hoop and flex cell segments participate in the expansion.

What is claimed is:

1. A stent comprising a stent body having at least one radiopaque marker, said marker defined by a radiopaque member affixed through an eyelet extending through a portion of said stent body, said eyelet having an internal surface that is irregular, and said radiopaque member being mechanically interlocked with the irregular internal surface within said eyelet, and wherein said internal eyelet surface is threaded.

2. The stent of claim 1, wherein entrances to said eyelet are chamfered.

3. The stent of claim 1, wherein said radiopaque member protrudes slightly outwardly from an outer surface of said stent body.

4. The stent of claim 1, wherein said radiopaque member is selected from the group of tungsten, gold, platinum, iridium and barium.

5. The stent of claim 4, wherein said radiopaque member is gold.

6. The stent of claim 1, wherein said radiopaque member is force fit into said eyelet.

7. A stent comprising a stent body having at least one radiopaque marker, said marker defined by a radiopaque member affixed through an eyelet extending through a portion of said stent body, said eyelet having an internal surface that has been grit blasted, and said radiopaque member being mechanically interlocked with said internal surface of said eyelet.

8. The stent of claim 7, wherein said internal surface of said eyelet is threaded.

9. The stent of claim 8, wherein entrances to said eyelet are chamfered.

10. The stent of claim 7, wherein said radiopaque member protrudes slightly outwardly from an outer surface of said stent body.

11. The stent of claim 7, wherein said radiopaque member is selected from the group of tungsten, gold, platinum, iridium and barium.

12. The stent of claim 11, wherein said radiopaque member is gold.

13. The stent of claim 7, wherein said radiopaque member is force fit into said eyelet.

14. A stent comprising a stent body having at least one radiopaque marker, said marker defined by a radiopaque member affixed through an eyelet extending through a portion of said stent body, said eyelet having an internal surface that has been acid etched, and said radiopaque member being mechanically interlocked with said internal surface of said eyelet.

15. The stent of claim 14, wherein, said internal surface of said eyelet is threaded.

16. The stent of claim 15, wherein entrances to said eyelet are chamfered.

17. The stent of claim 14, wherein said radiopaque member protrudes slightly outwardly from an outer surface of said stent body.

18. The stent of claim 14, wherein said radiopaque member is selected from the group of tungsten, gold, platinum, iridium and barium.

19. The stent of claim 18, wherein said radiopaque member is gold.

20. The stent of claim 14, wherein said radiopaque member is force fit into said eyelet.

* * * * *